（12）United States Patent
Mounce et al.

(10) Patent No.: US 8,277,415 B2
(45) Date of Patent: Oct. 2, 2012

(54) INFUSION MEDIUM DELIVERY DEVICE AND METHOD WITH DRIVE DEVICE FOR DRIVING PLUNGER IN RESERVOIR

(75) Inventors: R. Paul Mounce, Burbank, CA (US); Melissa D. Norton, Valencia, CA (US); Robert M. Guezuraga, Westlake Village, CA (US); Bradley J. Enegren, Moorpark, CA (US); Paul F. Bente, IV, Los Angeles, CA (US); Ian B. Hanson, Northridge, CA (US); Julian D. Kavazov, Arcadia, CA (US); Christopher G. Griffin, Sylmar, CA (US); Sheldon B. Moberg, Thousand Oaks, CA (US); Mark D. Holt, Moorpark, CA (US); Susie E. Maule, Redondo Beach, CA (US); Paul H. Kovelman, Simi Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 603 days.

(21) Appl. No.: 11/604,172

(22) Filed: Nov. 22, 2006

(65) Prior Publication Data

US 2008/0051711 A1 Feb. 28, 2008

Related U.S. Application Data

(63) Continuation-in-part of application No. 11/588,832, filed on Oct. 27, 2006, now Pat. No. 7,905,868, which is a continuation-in-part of application No. 11/515,225, filed on Sep. 1, 2006.

(60) Provisional application No. 60/839,822, filed on Aug. 23, 2006.

(51) Int. Cl.
*A61M 37/00* (2006.01)
*A61M 5/178* (2006.01)

(52) U.S. Cl. .......... 604/150; 604/154; 604/216
(58) Field of Classification Search .......... 604/232–235, 604/150–152, 154, 155, 69, 216, 218
See application file for complete search history.

(56) References Cited

U.S. PATENT DOCUMENTS 2,570,625 A 10/1951 Zimmerman et al.
(Continued)

FOREIGN PATENT DOCUMENTS

DE 10 2004 055 870 A1 5/2006
(Continued)

OTHER PUBLICATIONS

International Search Report dated Feb. 29, 2008 for PCT application PCT/US2007/076474.

(Continued)

*Primary Examiner* — Kevin C Sirmons
*Assistant Examiner* — Andrew Gilbert
(74) *Attorney, Agent, or Firm* — Foley & Lardner LLP

(57) ABSTRACT

A delivery device includes a durable housing portion and a separable disposable portion that selectively engage and disengage from each other. The disposable housing portion secures to the patient-user and may be disposed of after it has been in use for a prescribed period. Components that normally come into contact with a patient-user or with infusion medium are supported by the disposable housing portion, while the durable housing portion supports other components such as electronics and a drive device. A reservoir is supported by the disposable housing portion and has a moveable plunger that operatively couples to the drive device, when the disposable and durable housing portions are engaged.

42 Claims, 18 Drawing Sheets

U.S. PATENT DOCUMENTS

| | | |
|---|---|---|
| 2,644,450 A | 7/1953 | Krewson |
| 3,623,474 A | 11/1971 | Heilman et al. |
| 3,662,753 A | 5/1972 | Tassell |
| 3,802,430 A * | 4/1974 | Schwebel et al. ............... 604/69 |
| 3,963,151 A | 6/1976 | North, Jr. |
| 4,064,879 A | 12/1977 | Leibinsohn |
| 4,089,624 A | 5/1978 | Nichols et al. |
| 4,117,841 A | 10/1978 | Perrotta et al. |
| 4,215,701 A | 8/1980 | Raitto |
| 4,373,535 A | 2/1983 | Martell |
| 4,448,206 A | 5/1984 | Martell |
| 4,493,704 A | 1/1985 | Beard et al. |
| 4,585,435 A | 4/1986 | Vaillancourt |
| 4,684,366 A | 8/1987 | Denny et al. |
| 4,838,857 A | 6/1989 | Strowe et al. |
| 4,883,101 A | 11/1989 | Strong |
| 4,913,703 A | 4/1990 | Pasqualucci et al. |
| 4,976,696 A | 12/1990 | Sanderson et al. |
| 4,986,820 A | 1/1991 | Fischer |
| 4,994,034 A | 2/1991 | Botich et al. |
| 5,002,527 A | 3/1991 | Reller et al. |
| 5,053,001 A | 10/1991 | Reller et al. |
| 5,062,834 A | 11/1991 | Gross et al. |
| 5,090,963 A | 2/1992 | Gross et al. |
| 5,156,591 A | 10/1992 | Gross et al. |
| 5,176,502 A | 1/1993 | Sanderson et al. |
| 5,186,805 A | 2/1993 | Gross et al. |
| 5,190,522 A | 3/1993 | Wojcicki et al. |
| 5,203,506 A | 4/1993 | Gross et al. |
| 5,232,449 A | 8/1993 | Stern et al. |
| 5,242,406 A | 9/1993 | Gross et al. |
| 5,242,408 A | 9/1993 | Jhuboo et al. |
| 5,246,147 A | 9/1993 | Gross et al. |
| 5,254,096 A | 10/1993 | Rondelet et al. |
| 5,259,732 A | 11/1993 | Stern |
| 5,261,884 A | 11/1993 | Stern et al. |
| 5,275,582 A | 1/1994 | Wimmer |
| 5,295,966 A | 3/1994 | Stern et al. |
| 5,295,967 A | 3/1994 | Rondelet et al. |
| 5,312,364 A | 5/1994 | Jacobs |
| 5,356,632 A | 10/1994 | Gross et al. |
| 5,367,891 A | 11/1994 | Furuyama |
| 5,385,559 A | 1/1995 | Mannix |
| 5,409,236 A | 4/1995 | Therrien |
| 5,425,706 A | 6/1995 | Gross et al. |
| 5,496,285 A | 3/1996 | Schumacher et al. |
| 5,527,288 A | 6/1996 | Gross et al. |
| 5,697,916 A | 12/1997 | Schraga |
| 5,704,520 A | 1/1998 | Gross |
| 5,800,420 A | 9/1998 | Gross et al. |
| 5,807,375 A | 9/1998 | Gross et al. |
| 5,820,622 A | 10/1998 | Gross et al. |
| 5,848,991 A | 12/1998 | Gross et al. |
| 5,851,549 A | 12/1998 | Svec |
| 5,858,001 A | 1/1999 | Tsals et al. |
| 5,865,803 A | 2/1999 | Major |
| 5,871,125 A | 2/1999 | Gross |
| 5,933,287 A | 8/1999 | Müuller |
| 5,951,523 A | 9/1999 | Osterlind et al. |
| 5,954,697 A | 9/1999 | Srisathapat et al. |
| 5,957,889 A | 9/1999 | Poulsen et al. |
| 5,984,894 A | 11/1999 | Poulsen et al. |
| 5,997,501 A | 12/1999 | Gross et al. |
| 6,003,736 A | 12/1999 | Ljunggren |
| 6,033,377 A | 3/2000 | Rasmussen et al. |
| 6,099,504 A | 8/2000 | Gross et al. |
| 6,126,643 A | 10/2000 | Vaillancouert |
| 6,186,982 B1 | 2/2001 | Gross et al. |
| 6,229,584 B1 | 5/2001 | Chuo et al. |
| 6,248,093 B1 | 6/2001 | Moberg |
| 6,261,272 B1 | 7/2001 | Gross et al. |
| 6,275,717 B1 | 8/2001 | Gross et al. |
| 6,277,095 B1 | 8/2001 | Kriesel et al. |
| 6,312,409 B1 | 11/2001 | Gross |
| 6,314,317 B1 | 11/2001 | Willis |
| 6,346,095 B1 | 2/2002 | Gross et al. |
| 6,364,865 B1 | 4/2002 | Lavi et al. |
| 6,406,455 B1 | 6/2002 | Willis et al. |
| 6,423,035 B1 | 7/2002 | Das et al. |
| 6,440,096 B1 | 8/2002 | Lastovich et al. |
| 6,461,329 B1 | 10/2002 | Van Antwerp et al. |
| 6,474,219 B2 | 11/2002 | Klitmose et al. |
| 6,478,771 B1 | 11/2002 | Lavi et al. |
| 6,485,461 B1 | 11/2002 | Mason et al. |
| 6,485,465 B2 | 11/2002 | Moberg et al. |
| 6,490,483 B2 | 12/2002 | Willis |
| 6,503,225 B1 | 1/2003 | Kirsch et al. |
| 6,508,788 B2 | 1/2003 | Preuthun |
| 6,537,251 B2 | 3/2003 | Klitmose |
| 6,585,707 B2 | 7/2003 | Cabiri et al. |
| 6,589,229 B1 | 7/2003 | Connelly et al. |
| 6,595,956 B1 | 7/2003 | Gross et al. |
| 6,607,509 B2 | 8/2003 | Bobroff et al. |
| 6,607,513 B1 | 8/2003 | Down et al. |
| 6,613,019 B2 | 9/2003 | Munk |
| 6,616,627 B2 | 9/2003 | Willis et al. |
| 6,626,874 B1 | 9/2003 | Duchamp |
| 6,641,565 B1 | 11/2003 | Lavi et al. |
| 6,641,566 B2 | 11/2003 | Douglas et al. |
| 6,645,181 B1 | 11/2003 | Lavi et al. |
| 6,656,147 B1 | 12/2003 | Gertsek et al. |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,689,100 B2 | 2/2004 | Connelly et al. |
| 6,692,457 B2 | 2/2004 | Flaherty |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,195 B2 | 4/2004 | Nolan, Jr. et al. |
| 6,723,068 B2 | 4/2004 | Lavi et al. |
| 6,723,072 B2 | 4/2004 | Flaherty et al. |
| 6,740,059 B2 | 5/2004 | Flaherty |
| 6,749,587 B2 * | 6/2004 | Flaherty ...................... 604/151 |
| 6,767,188 B2 | 7/2004 | Vrane et al. |
| 6,768,425 B2 | 7/2004 | Flaherty et al. |
| 6,786,246 B2 | 9/2004 | Ohms et al. |
| 6,808,506 B2 | 10/2004 | Lastovich et al. |
| 6,830,558 B2 | 12/2004 | Flaherty et al. |
| 6,830,560 B1 | 12/2004 | Gross et al. |
| 6,886,724 B2 | 5/2005 | Hung |
| 6,899,699 B2 | 5/2005 | Enggaard |
| 6,936,006 B2 | 8/2005 | Sabra |
| 6,939,324 B2 | 9/2005 | Gonnelli et al. |
| 6,948,918 B2 | 9/2005 | Hansen |
| 6,952,604 B2 | 10/2005 | DeNuzzio et al. |
| 6,960,184 B2 | 11/2005 | Willis et al. |
| 6,960,192 B1 | 11/2005 | Flaherty et al. |
| 6,997,911 B2 | 2/2006 | Klitmose |
| 7,008,399 B2 | 3/2006 | Larsen et al. |
| 7,018,360 B2 | 3/2006 | Flaherty et al. |
| 7,027,478 B2 | 4/2006 | Ackley |
| 7,029,455 B2 | 4/2006 | Flaherty |
| 7,083,592 B2 | 8/2006 | Lastovich et al. |
| 7,083,599 B2 | 8/2006 | Alchas et al. |
| 7,115,108 B2 | 10/2006 | Wilkinson et al. |
| 7,128,727 B2 | 10/2006 | Flaherty et al. |
| 7,133,329 B2 | 11/2006 | Skyggebjerg et al. |
| 7,137,964 B2 | 11/2006 | Flaherty |
| 7,144,384 B2 | 12/2006 | Gorman et al. |
| 7,150,409 B2 | 12/2006 | Gonnelli et al. |
| 7,156,838 B2 | 1/2007 | Gabel et al. |
| 7,187,969 B2 | 3/2007 | Willis |
| 7,220,889 B2 | 5/2007 | Sigurjonsson et al. |
| 7,318,816 B2 | 1/2008 | Bobroff et al. |
| 2001/0041869 A1 | 11/2001 | Causey et al. |
| 2002/0040208 A1 | 4/2002 | Flaherty et al. |
| 2002/0072733 A1 | 6/2002 | Flaherty |
| 2002/0123740 A1 | 9/2002 | Flaherty et al. |
| 2002/0126036 A1 | 9/2002 | Flaherty et al. |
| 2002/0169439 A1 | 11/2002 | Flaherty |
| 2003/0055380 A1 | 3/2003 | Flaherty |
| 2003/0073952 A1 | 4/2003 | Flaherty et al. |
| 2003/0097092 A1 | 5/2003 | Flaherty |
| 2003/0125672 A1 | 7/2003 | Adair et al. |
| 2003/0167035 A1 | 9/2003 | Flaherty et al. |
| 2003/0167036 A1 | 9/2003 | Flaherty |

| | | | |
|---|---|---|---|
| 2003/0199824 A1 | 10/2003 | Mahoney et al. | |
| 2003/0199825 A1 | 10/2003 | Flaherty | |
| 2003/0212364 A1 | 11/2003 | Mann et al. | |
| 2003/0229310 A1 | 12/2003 | Flaherty et al. | |
| 2003/0233069 A1 | 12/2003 | Gillespie, Jr. et al. | |
| 2004/0002682 A1 | 1/2004 | Kovelman et al. | |
| 2004/0010207 A1 | 1/2004 | Flaherty et al. | |
| 2004/0011866 A1 | 1/2004 | Saad | |
| 2004/0015131 A1 | 1/2004 | Flaherty et al. | |
| 2004/0064088 A1 | 4/2004 | Gorman et al. | |
| 2004/0064096 A1 | 4/2004 | Flaherty et al. | |
| 2004/0073095 A1 | 4/2004 | Causey et al. | |
| 2004/0078028 A1 | 4/2004 | Flaherty et al. | |
| 2004/0087894 A1 | 5/2004 | Flaherty | |
| 2004/0092865 A1 | 5/2004 | Flaherty et al. | |
| 2004/0116866 A1 | 6/2004 | Gorman et al. | |
| 2004/0158207 A1 | 8/2004 | Hunn et al. | |
| 2004/0199140 A1 | 10/2004 | Rue et al. | |
| 2004/0204673 A1 | 10/2004 | Flaherty | |
| 2004/0220551 A1 | 11/2004 | Flaherty et al. | |
| 2004/0235446 A1 | 11/2004 | Flaherty et al. | |
| 2004/0260233 A1 | 12/2004 | Garibotto et al. | |
| 2005/0022274 A1 | 1/2005 | Campbell et al. | |
| 2005/0065760 A1 | 3/2005 | Murtfeldt et al. | |
| 2005/0119618 A1* | 6/2005 | Gonnelli | 604/150 |
| 2005/0137530 A1* | 6/2005 | Campbell et al. | 604/150 |
| 2006/0184119 A1 | 8/2006 | Remde et al. | |
| 2006/0253085 A1 | 11/2006 | Geismar et al. | |
| 2006/0264835 A1 | 11/2006 | Nielsen et al. | |
| 2006/0264894 A1 | 11/2006 | Moberg et al. | |
| 2007/0073235 A1 | 3/2007 | Estes et al. | |
| 2007/0293826 A1 | 12/2007 | Wall et al. | |
| 2008/0051710 A1 | 2/2008 | Moberg et al. | |
| 2008/0051730 A1 | 2/2008 | Bikovsky | |
| 2008/0269682 A1 | 10/2008 | Kavazov et al. | |

FOREIGN PATENT DOCUMENTS

| | | |
|---|---|---|
| DE | 20 2007 006 363 U1 | 8/2007 |
| EP | 1 462 134 A1 | 9/2004 |
| EP | 1 527 792 A1 | 5/2005 |
| EP | 1 347 705 | 12/2005 |
| EP | 1 423 079 | 7/2006 |
| EP | 1 135 056 | 8/2006 |
| EP | 1 702 635 | 9/2006 |
| EP | 1 545 657 | 11/2006 |
| EP | 1 546 556 | 12/2006 |
| EP | 1 341 569 | 1/2007 |
| EP | 1 461 070 | 1/2007 |
| EP | 1 464 351 | 1/2007 |
| EP | 1 309 366 | 2/2007 |
| EP | 0 944 648 | 3/2007 |
| EP | 1 646 412 | 3/2007 |
| EP | 1 095 668 | 4/2007 |
| FR | 1496026 | 9/1967 |
| GB | 1 452 104 | 10/1976 |
| GB | 2 176 711 A | 1/1987 |
| GB | 2 207 652 A | 2/1989 |
| WO | WO-95/23015 | 11/1995 |
| WO | WO 95/32015 | 11/1995 |
| WO | WO 96/26702 | 9/1996 |
| WO | WO-97/44078 | 11/1997 |
| WO | WO-97/46203 | 12/1997 |
| WO | WO-99/48546 | 9/1999 |
| WO | WO 99/59665 | 11/1999 |
| WO | WO 00/47254 | 8/2000 |
| WO | WO-00/69488 | 11/2000 |
| WO | WO-01/70307 A1 | 9/2001 |
| WO | WO 01/76684 A1 | 10/2001 |
| WO | WO-02/02165 A2 | 1/2002 |
| WO | WO 02/20073 A2 | 3/2002 |
| WO | WO 02/28454 A2 | 4/2002 |
| WO | WO 02/40083 A2 | 5/2002 |
| WO | WO 02/49509 A2 | 6/2002 |
| WO | WO 02/068015 A2 | 9/2002 |
| WO | WO 03/006090 A1 | 1/2003 |
| WO | WO 03/024504 A2 | 3/2003 |
| WO | WO-03/026728 A1 | 4/2003 |
| WO | WO 03/033051 A1 | 4/2003 |
| WO | WO 03/059372 A2 | 7/2003 |
| WO | WO 03/059372 A3 | 7/2003 |
| WO | WO-03/072172 A2 | 9/2003 |
| WO | WO 03/074121 A1 | 9/2003 |
| WO | WO 03/090509 A2 | 11/2003 |
| WO | WO 03/090819 A2 | 11/2003 |
| WO | WO 03/090838 A1 | 11/2003 |
| WO | WO 03/103758 A1 | 12/2003 |
| WO | WO 03/103763 A1 | 12/2003 |
| WO | WO 2004/006981 A2 | 1/2004 |
| WO | WO 2004/006982 A2 | 1/2004 |
| WO | WO 2004/030716 A2 | 4/2004 |
| WO | WO 2004/030717 A2 | 4/2004 |
| WO | WO 2004/047641 A2 | 6/2004 |
| WO | WO 2004/060436 A2 | 7/2004 |
| WO | WO 2004/093648 A2 | 11/2004 |
| WO | WO 2004/098390 A2 | 11/2004 |
| WO | WO 2004/098454 A2 | 11/2004 |
| WO | WO-2004/098683 A1 | 11/2004 |
| WO | WO 2004/110526 A1 | 12/2004 |
| WO | WO-2005/000382 A2 | 1/2005 |
| WO | WO-2005/072795 A2 | 8/2005 |
| WO | WO 2005/094920 A1 | 10/2005 |
| WO | WO-2005/097237 A1 | 10/2005 |
| WO | WO 2006/015922 A1 | 2/2006 |
| WO | WO 2006/018425 A2 | 2/2006 |
| WO | WO 2006/018425 A3 | 2/2006 |
| WO | WO 2006/018447 A2 | 2/2006 |
| WO | WO 2006/018447 A3 | 2/2006 |
| WO | WO 2006/024671 A1 | 3/2006 |
| WO | WO 2006/024672 A1 | 3/2006 |
| WO | WO 2006/032692 A1 | 3/2006 |
| WO | WO 2006/042811 A2 | 4/2006 |
| WO | WO 2006/042811 A3 | 4/2006 |
| WO | WO-2006/058435 A2 | 6/2006 |
| WO | WO 2006/072416 A2 | 7/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/084464 A1 | 8/2006 |
| WO | WO 2006/086980 A1 | 8/2006 |
| WO | WO 2006/089547 A1 | 8/2006 |
| WO | WO 2006/089548 A1 | 8/2006 |
| WO | WO 2006/089965 A1 | 8/2006 |
| WO | WO 2006/096746 A1 | 9/2006 |
| WO | WO 2006/097453 A1 | 9/2006 |
| WO | WO 2006/104806 A2 | 10/2006 |
| WO | WO 2006/108775 A2 | 10/2006 |
| WO | WO 2006/108809 A1 | 10/2006 |
| WO | WO 2006/116997 A1 | 11/2006 |
| WO | WO 2006/120253 A2 | 11/2006 |
| WO | WO 2006/125692 A1 | 11/2006 |
| WO | WO 2007/000425 A2 | 1/2007 |
| WO | WO 2007/000426 A2 | 1/2007 |
| WO | WO 2007/000427 A1 | 1/2007 |
| WO | WO 2007/038091 A2 | 4/2007 |
| WO | WO 2007/062068 A2 | 5/2007 |
| WO | WO 2007/071255 A2 | 6/2007 |
| WO | WO-2007/076641 A1 | 7/2007 |
| WO | WO 2007/087808 A1 | 8/2007 |
| WO | WO 2007/130809 A2 | 11/2007 |
| WO | WO-2008/024614 A2 | 2/2008 |
| WO | WO 2008/093063 A2 | 8/2008 |
| WO | WO-2008/136845 | 11/2008 |
| WO | WO-2008/151241 A2 | 12/2008 |

OTHER PUBLICATIONS

Partial International Search Report dated Jan. 2, 2008 for PCT application PCT/US2007/076474.
Partial PCT Search Report dated Mar. 5, 2009 from related PCT application No. PCT/US2008/082187.
PCT Search Report dated Apr. 28, 2009 from related PCT application No. PCT/US2008/082186.
Office Action dated Nov. 24, 2008 from related U.S. Appl. No. 11/759,725.
Notice of Allowance dated Jan. 19, 2010 from related U.S. Appl. No. 11/759,725.
Notice of Allowance dated Jun. 23, 2009 from related U.S. Appl. No. 11/759,725.

Office Action Dated Apr. 10, 2009 from related U.S. Appl. No. 11/588,832.
Office Action dated Apr. 13, 2009 from related U.S. Appl. No. 11/604,171.
Office Action dated Apr. 9, 2009 from related U.S. Appl. No. 11/515,225.
Office Action dated Mar. 10, 2010 from related U.S. Appl. No. 11/515,225.
Office Action dated Mar. 2, 2010 from related U.S. Appl. No. 11/588,832.
Office Action dated Nov. 19, 2008 from related U.S. Appl. No. 11/515,225.
Office Action dated Nov. 21, 2008 from related U.S. Appl. No. 11/588,832.
Office Action dated Nov. 21, 2008 from related U.S. Appl. No. 11/604,171.
Office Action dated Oct. 19, 2009 from related U.S. Appl. No. 11/515,225.
Office Action dated Oct. 9, 2009 from related U.S. Appl. No. 11/604,171.
Search Report dated Jan. 11, 2010 from related European patent application No. 07841183.2.
US Notice of Allowance dated Jan. 26, 2011 from related U.S. Appl. No. 11/588,832.
Notice of Allowance dated Apr. 26, 2010 from related U.S. Appl. No. 11/604,171.
Notice of Allowance dated May 14, 2010 from related U.S. Appl. No. 11/759,725.
Office Action dated Mar. 17, 2010 from related U.S. Appl. No. 11/604,171.
Office Action dated Aug. 10, 2010 from related U.S. Appl. No. 11/588,832.

* cited by examiner

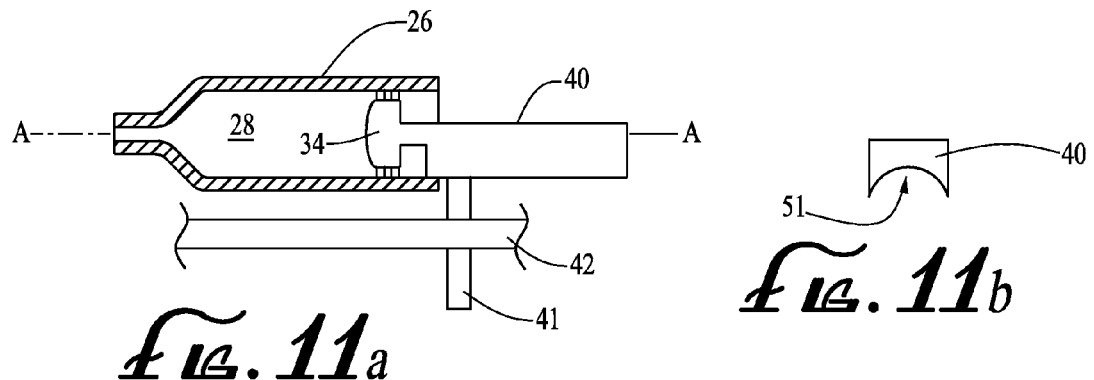
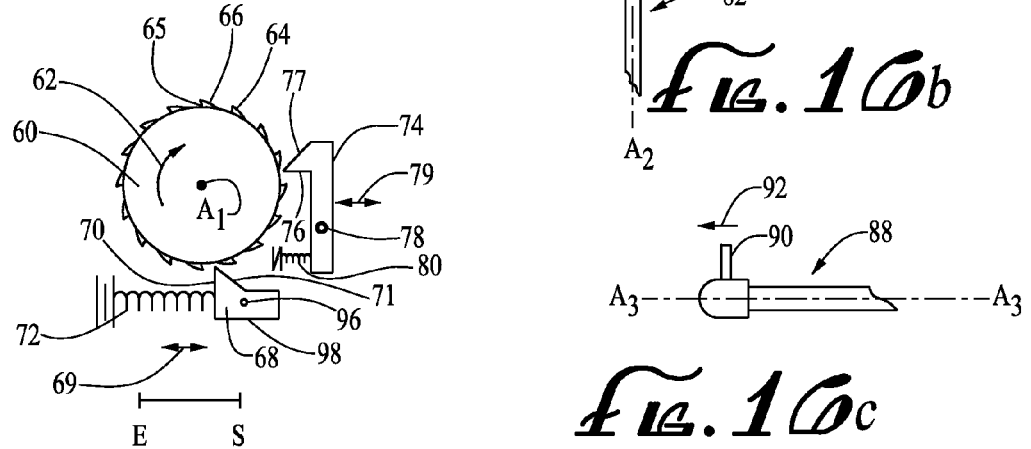
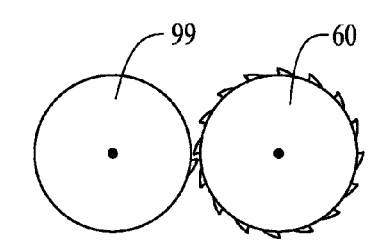

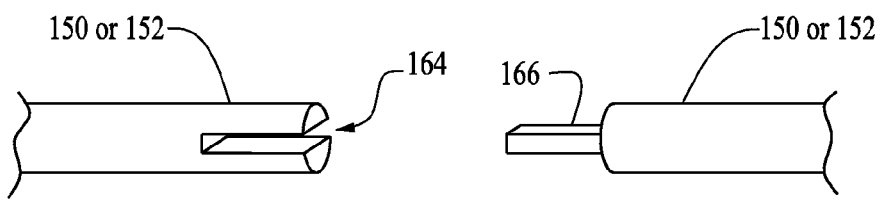
FIG. 22
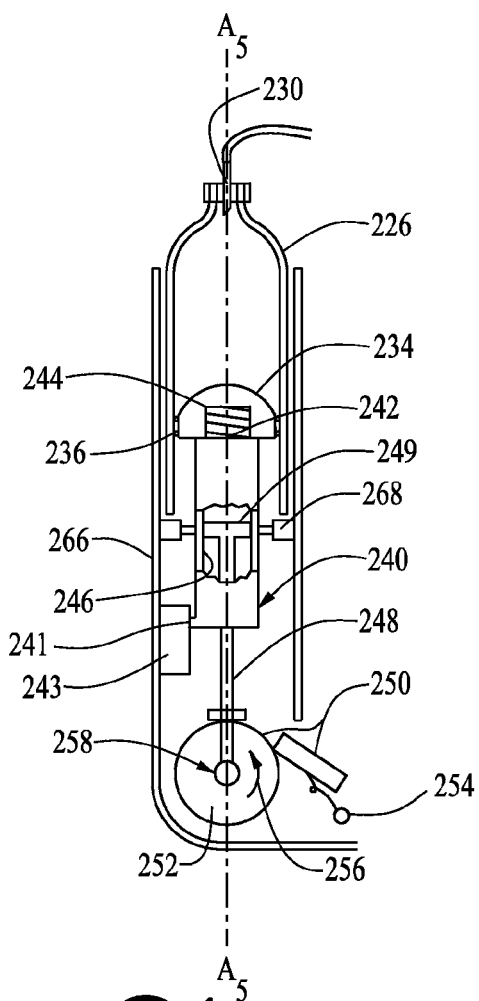
FIG. 23
FIG. 24

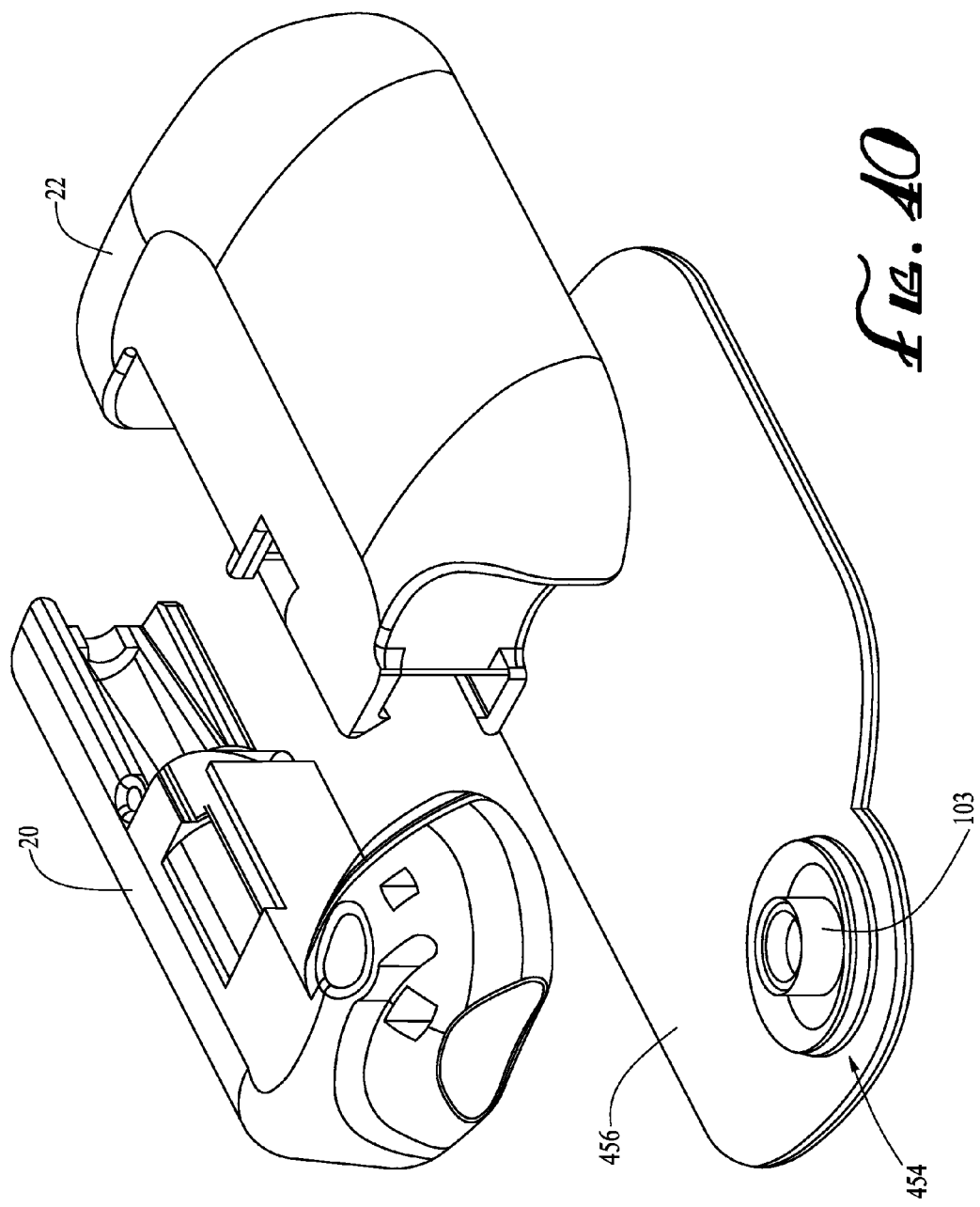

INFUSION MEDIUM DELIVERY DEVICE AND METHOD WITH DRIVE DEVICE FOR DRIVING PLUNGER IN RESERVOIR

CROSS-REFERENCE TO RELATED PATENT APPLICATIONS

The present application is a Continuation-In-Part of U.S. patent application Ser. No. 11/588,832, filed on Oct. 27, 2006, now U.S. Pat. No. 7,905,868, which is a Continuation-In-Part of U.S. patent application Ser. No. 11/515,225, filed on Sep. 1, 2006, which claims benefit of 60/839,822, filed Aug. 23, 2006, which are incorporated herein by reference in their entirety. This application claims priority from Provisional Application U.S. Application 60/839,822, filed Aug. 23, 2006, incorporated herein by reference in its entirety. The present invention also relates to U.S. Provisional Patent Application 60/678,290, filed May 6, 2005 and U.S. patent application Ser. No. 11/211,095, filed Aug. 23, 2005, each of which is incorporated herein by reference in its entirety. The present invention also relates to co-pending application No. 60/839,821, titled SYSTEMS AND METHODS ALLOWING FOR RESERVOIR FILLING AND INFUSION MEDIUM DELIVERY, filed Aug. 23, 2006; co-pending application No. 60/839,832, titled INFUSION MEDIUM DELIVERY DEVICE AND METHOD WITH COMPRESSIBLE OR CURVED RESERVOIR OR CONDUIT, filed Aug. 23, 2006; co-pending application No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006; and co-pending application No. 60/839,741, titled INFUSION PUMPS AND METHODS AND DELIVERY DEVICES AND METHODS WITH SAME, filed Aug. 23, 2006. Embodiments of the present invention also relate to: (i) U.S. patent application Ser. No. 11/588,875, filed Oct. 27, 2006, entitled "Systems And Methods Allowing For Reservoir Filling And Infusion Medium Delivery"; (ii) U.S. patent application Ser. No. 11/588,847, filed Oct. 27, 2006, entitled "Infusion Medium Delivery Device and Method with Compressible or Curved Reservoir or Conduit"; (iii) U.S. Provisional Patent Application Ser. No. 60/854,829, filed Oct. 27, 2006, entitled "Infusion Medium Delivery System, Device and Method with Needle Inserter and Needle Inserter Device and Method"; and (iv) U.S. patent application Ser. No. 11/589,323, filed Aug. 23, 2006, entitled "Infusion Pumps and Methods and Delivery Devices and Methods with Same", the contents of each of which are incorporated by reference herein, in their entirety.

FIELD OF THE INVENTION

Embodiments of the present invention relate to an infusion medium delivery device for delivering an infusion medium to a patient-user, where the delivery device includes a base portion and a durable portion connectable to the base portion, where the base portion is securable to a patient-user's skin and can be removed and disposed of after a specified number of uses.

BACKGROUND OF THE INVENTION

Certain chronic diseases may be treated, according to modern medical techniques, by delivering a medication or other substance to a patient's body, either in a continuous manner or at particular times or time intervals within an overall time period. For example, diabetes is a chronic disease that is commonly treated by delivering defined amounts of insulin to the patient at appropriate times. Some common modes of providing an insulin therapy to a patient include delivery of insulin through manually operated syringes and insulin pens. However, other modern systems employ programmable pumps to deliver controlled amounts of insulin to a patient.

Pump type delivery devices have been configured in external devices (that connect to a patient) or implantable devices (to be implanted inside of a patient's body). External pump type delivery devices include devices designed for use in a stationary location (for example, in a hospital or clinic), and further devices configured for ambulatory or portable use (to be carried by a patient). Examples of some external pump type delivery devices are described in Published PCT Application WO 01/70307 (PCT/US01/09139) titled "Exchangeable Electronic Cards For Infusion Devices" (which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump type delivery devices may be connected in fluid-flow communication to a patient-user, for example, through a suitable hollow tubing. The hollow tubing may be connected to a hollow needle designed to pierce the patient-user's skin and deliver an infusion medium there-through. Alternatively, the hollow tubing may be connected directly to the patient-user as or through a cannula or set of micro-needles.

In contexts in which the hollow tubing is connected to the patient-user through a hollow needle that pierces the patient-user's skin, a manual insertion of the needle into the patient-user can be somewhat traumatic to the patient-user. Accordingly, insertion tools have been made to assist the insertion of a needle into the patient-user, whereby a needle is forced by a spring to quickly move from a retracted position into an extended position. One example of such an insertion tool is described in U.S. Patent Application Publication No. 2002/0022855, titled "Insertion Device For An Insertion Set And Method Of Using The Same" (assigned to the assignee of the present invention), which is incorporated herein by reference in its entirety. As the needle is moved into the extended position, the needle is quickly forced through the patient-user's skin in a single, relatively abrupt motion that can be less traumatic to a patient-user as compared to a slower, manual insertion of a needle. However, in some contexts, a controlled, slow insertion speed can be less traumatic to some patients.

As compared to syringes and insulin pens, pump type delivery devices can be significantly more convenient to a patient-user, in that accurate doses of insulin may be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump type delivery devices have become an important aspect of modern medical treatments of various types of medical conditions, such as diabetes. As pump technologies improve and doctors and patient-users become more familiar with such devices, the popularity of external medical infusion pump treatment increases and is expected to increase substantially over the next decade.

SUMMARY OF THE DISCLOSURE

Embodiments of the present invention relate to an infusion medium delivery device for delivering an infusion medium to a patient-user, wherein the delivery device includes a first (or durable) housing portion and a second (or disposable) housing portion that selectively, engage and disengage from each other, for example, by manual force. One or both of the first and second housing portions secures to the patient-user. The disposable housing portion may be disposed of after it has been in use for a prescribed period. Components that normally come into contact with a patient-user and/or with infusion media may be supported by the disposable housing portion for disposal after the prescribed use, while the durable housing portion supports other components such as electronics for controlling the delivery of infusion media.

According to embodiments of the invention, a delivery device includes first and second housing portions as described above and a reservoir located in the first housing portion. The reservoir has an interior for containing a fluidic medium and a plunger is moveable within the interior of the reservoir along an axial direction of the reservoir. A rotatable shaft is disposed at least partially within the reservoir interior, along the axial direction of the reservoir.

In an example embodiment, the rotatable shaft extends through a threaded channel in the plunger and has a threaded portion that is operatively engaged with the threaded channel of the plunger. Rotation of the rotatable shaft causes the plunger to move along the length of the threaded portion of the rotatable shaft to vary the interior volume of the reservoir. A drive device is supported by the durable housing portion in a position to operatively connect to the rotatable shaft, to selectively rotate the rotatable shaft, when the disposable and durable housing portions are engaged.

A delivery device according to the above-described embodiment may also include at least one seal arranged between the rotatable shaft and the plunger, to inhibit the passage of the fluidic medium through the central channel of the plunger. The seal may comprise at least one layer of sealing material disposed over the rotatable shaft. In another embodiment, the seal comprises a plurality of o-ring seals disposed around the rotatable shaft.

A delivery device for delivering an infusion medium to a patient-user according to a further example embodiment also includes first and second housing portions and a reservoir as described above. In this further example, embodiment, a plunger moveable within the reservoir and a slide member having an end for engaging the plunger is supported by the durable housing portion. The slide member has a threaded, at least partially generally cylindrical surface. A rotatable shaft is supported by the durable housing portion and extends along the threaded surface of the slide member and has a threaded portion operatively engaged with the threaded surface of the slide member to move the slide member in the axial direction of the reservoir by rotation of the rotatable shaft relative to the slide member. A drive device is supported by the durable housing portion and is operatively coupled to the rotatable shaft to selectively rotate the rotatable shaft. In such an embodiment, movement of the slide member by the rotation of the rotatable shaft is transferred to movement of the plunger in the axial direction of the reservoir, when the slide member is engaged with the plunger.

A delivery device according to the above-described further example embodiment may also include an anti-rotation structure for inhibiting rotation of the slide member around the axial direction. Also, the slide member may extend through an aperture in the durable housing portion and at least one seal member may be provided around the aperture. The slide member may include a tube structure that has a hollow, generally cylindrical interior, wherein the threaded surface of the slide member is at least a portion of an interior surface of the tube structure. Alternatively, the slide member may include a partial tube structure having a hollow, semi-cylindrical interior, wherein the threaded surface of the slide member is at least a portion of a semi-cylindrical interior surface of the partial tube structure.

A delivery device according to the above-described further example embodiment may include a second reservoir supported by the disposable housing portion and having an interior for containing a fluidic medium, and a second plunger moveable within the interior of the second reservoir along an axial direction of the second reservoir. In such an embodiment, a second slide member is supported by the durable housing portion and has an end for engaging the second plunger when the disposable housing portion and durable housing portion are engaged. The second slide member also has a threaded, at least partially generally cylindrical surface. A second rotatable shaft is supported by the durable housing portion and extends along the threaded surface of the second slide member. The second rotatable shaft has a threaded portion operatively engaged with the threaded surface of the second slide member to move the second slide member in the axial direction of the second reservoir by rotation of the second rotatable shaft relative to the second slide member. In such an embodiment, the drive device is also operatively coupled to the second rotatable shaft to selectively rotate the second rotatable shaft. Movement of the second slide member by the rotation of the second rotatable shaft is transferred to movement of the second plunger in the axial direction of the second reservoir, when the second slide member is engaged with the second plunger.

A delivery device for delivering an infusion medium to a patient-user according to a further example embodiment also includes first and second housing portions, a reservoir and a plunger moveable within the reservoir as described above. In addition, this further embodiment includes a slide member supported by the durable housing portion, where the slide member has an end for engaging the plunger when the disposable housing portion and durable housing portion are engaged, and the slide member also has an engagement surface for engaging a drive surface of a piezoelectric stack drive device. In this further embodiment, a shaft is supported by the durable housing portion and extends along the engagement surface of the slide member. A piezoelectric stack drive device is supported by the shaft and is arranged to operatively engage the slide member to selectively move the slide member in the axial direction of the reservoir. Movement of the slide member by operation of the piezoelectric stack drive device is transferred to movement of the plunger in the axial direction of the reservoir, when the slide member is engaged with the plunger.

A delivery device according to the above-described further example embodiment also may also include at least one seal arranged between the rotatable shaft and the plunger, to inhibit the passage of the fluidic medium through the central channel of the plunger. The seal may comprise at least one layer of sealing material disposed over the rotatable shaft. In another embodiment, the seal comprises a plurality of o-ring seals disposed around the rotatable shaft. Also, in the above-described further example embodiment, the slide member may include a tube structure that has a hollow, generally cylindrical interior and the engagement surface of the slide member may include at least a portion of an interior surface of the tube structure.

A delivery device for delivering an infusion medium to a patient-user according to yet a further example embodiment also includes first and second housing portions, a reservoir and a plunger moveable within the reservoir as described above. In addition, this further embodiment includes an expandable structure that has an interior volume and an end for engaging the plunger and moving the plunger as the expandable structure is expanded, when the disposable housing portion and the durable housing portion are engaged. The expandable structure may include a bellows structure. This further embodiment also includes a second reservoir supported by the durable housing portion, for containing a second fluid medium for expanding the expandable structure and a conduit for coupling the second reservoir to an interior volume of the expandable structure. In addition, a drive device is supported by the durable housing portion, for selectively conveying the second fluidic medium through the conduit, from the second reservoir to the interior volume of the expandable structure, to selectively expand the expandable structure, when the first housing portion and the second housing portion are engaged.

In the above-described further example embodiment, the drive device may include a peristaltic drive device or other type of fluid pump. In such an embodiment, the peristaltic drive device may include a rotatable rotor that has a plurality of contact rollers or pads arranged to contact a first length of the conduit as the rotor is rotated, and a support surface may be provided on the durable housing portion for supporting at least the first length of the conduit. The support surface may include a curved surface. The drive device may include a motor operatively coupled to rotate the rotatable rotor. A linkage structure may be coupled to the motor and to the rotatable rotor, to transfer drive force from the motor to the rotatable rotor.

Alternatively, in the above-described further example embodiment, the drive device may include a rotatable rotor having a plurality of contact rollers or pads arranged to contact a first length of the conduit as the rotor is rotated along a radius of curvature. In such embodiment, a curved surface is provided on the durable housing portion for supporting at least the first length of the conduit, where the curved surface having a radius of curvature approximating the radius of curvature of the rotor rollers or pads. A motor may be operatively coupled to rotate the rotatable rotor.

In any of the above-described embodiments, the durable housing portion may have an enclosed interior volume that contains the drive device, and the drive device may be operatively connected to a connection end of the rotatable shaft through a drive linkage that extends through an aperture in the durable housing portion. In such an embodiment, a connection end of the drive linkage and the connection end of the rotatable shaft have mating shapes that mate together and allow transfer of rotational motion from the drive linkage to the rotatable shaft, when the disposable and durable housing portions are engaged. Also, in such an embodiment, a seal may be provided adjacent the aperture in the durable housing portion, to seal the aperture through which the drive linkage extends.

A delivery device according to any of the above-described embodiments may include electrical control circuitry contained in the durable housing portion. The electrical control circuitry controls the delivery of infusion medium from the reservoir to the patient-user when the durable housing portion and the disposable housing portion are engaged.

In any of the above-described embodiments, the disposable housing portion may include a base portion having a bottom surface and an adhesive material on the bottom surface for securing the disposable housing portion to the skin of the patient-user. Also, in any of the above-described embodiments, the reservoir may include a septum that may be pierced by a hollow needle for providing a fluid flow path from the interior of the reservoir to the hollow needle.

Also, any of the above-described embodiments may further include an anti-rotation structure to inhibit the plunger from rotating within the reservoir. In such embodiments, the anti-rotation structure may include at least one projection extending from one of the plunger and the interior surface of the reservoir and at least one channel provided in the other one of the plunger and the interior surface of the reservoir. Each projection is configured to extend at least partially into a channel.

Also, in any of the above-described embodiments, at least one seal may be arranged around the outer peripheral surface of the plunger, for inhibiting the passage of infusion medium between the outer peripheral surface of the plunger and an interior surface of the reservoir.

In any of the above-described embodiments, a linkage structure may be provided for operatively coupling the drive device to the rotatable shaft. Also, in any of the above-described embodiments, the drive device may include a rotary motor operatively connected to rotate the rotatable shaft. Alternatively, or in addition, the drive device may include an escapement wheel that is supported for rotation and is operatively connected to rotate the rotatable shaft and/or drive linkage with rotation of the escapement wheel. In such embodiments, an actuator is operatively connected to the escapement wheel for selectively rotating the escapement wheel. For example, a drive pawl may be supported for linear movement between a start position and an end position and may have a drive surface arranged to engage a tooth of the escapement wheel and rotate the escapement wheel in a first direction as the drive pawl moves between the start and end positions. An actuator may be operatively connected to the drive pawl, for selectively moving the drive pawl from the start position to the end position.

Further embodiments of the present invention relate to methods of making a delivery device for delivering an infusion medium to a patient-user. Such methods include providing a first housing portion adapted to be secured to a patient-user and providing a second housing portion configured to be selectively engaged with and disengaged from the first housing portion to allow disposal of the first housing portion without disposing of the second housing portion. Such methods further include supporting a reservoir on the first housing portion, the reservoir having an interior for containing a fluidic medium and arranging a plunger within the interior of the reservoir and moveable relative to the reservoir along an axial direction of the reservoir. Such methods further include arranging a rotatable shaft at least partially within the reservoir interior, along the axial direction of the reservoir, extending the rotatable shaft through the threaded channel of the plunger, and operatively engaging a threaded portion of the rotatable shaft with the threaded channel of the plunger. In such embodiments, rotation of the rotatable shaft relative to the plunger causes the plunger to move along the length of the threaded portion of the rotatable shaft to vary the interior volume of the reservoir. Such embodiments further include supporting a drive device on the second housing portion in a position to operatively connect to the rotatable shaft, to selectively rotate the rotatable shaft, when the first and second housing portions are engaged.

Further method embodiments include arranging at least one seal between the rotatable shaft and the plunger, to inhibit the passage of the fluidic medium through the central channel of the plunger. In one example, arranging at least one seal includes providing at least one layer of sealing material over the rotatable shaft. In another example, arranging at least one seal includes providing a plurality of o-ring seals disposed around the rotatable shaft.

A method for making a delivery device for delivering an infusion medium to a patient-user according to a further example embodiment also includes providing first and second housing portions and supporting a reservoir as described above. In this further example, embodiment, a method includes arranging a plunger within the interior of the reservoir and movable along an axial direction of the reservoir. A method according to this further example also includes supporting a slide member on the second housing portion, with an end of the slide member arranged to engage the plunger when the first housing portion and the second housing portion are engaged. In addition this method includes supporting a rotatable shaft on the second housing portion, extending the rotatable shaft along the threaded surface of the slide member and operatively engaging a threaded portion of the rotatable shaft with the threaded surface of the slide member to move the slide member in the axial direction of the reservoir by rotation of the rotatable shaft relative to the slide member. This method also includes operatively coupling a drive device to the rotatable shaft to selectively rotate the rotatable shaft, such that movement of the slide member by the rotation of the rotatable shaft is transferred to movement of the plunger in the axial direction of the reservoir, when the slide member is engaged with the plunger.

A method according to the above further example embodiment may further include providing an anti-rotation structure for inhibiting rotation of the slide member relative to the reservoir. A method according to the above further example embodiment also may include extending the slide member through an aperture in the second housing portion and providing at least one seal member around the aperture. In a method according to the above further example embodiment, supporting a slide member may include supporting a tube structure on the second housing portion, where the tube structure has a hollow, generally cylindrical interior and the threaded surface of the slide member includes at least a portion of a generally cylindrical interior surface of the tube structure. Alternatively, supporting a slide member may include supporting a partial tube structure on the second housing portion, where the partial tube structure has a hollow, semi-cylindrical interior and the threaded surface of the slide member includes at least a portion of a semi-cylindrical interior surface of the partial tube structure.

A method according to the above-described further example embodiment may further include supporting a second reservoir on the first housing portion, where the second reservoir has an interior for containing a fluidic medium. This further method also includes arranging a second plunger within the interior of the second reservoir and moveable along an axial direction of the second reservoir and supporting a second slide member on the second housing portion in a position at which an end of the second slide member engages the second plunger when the first housing portion and the second housing portion are engaged, the second slide member further having a threaded, at least partially generally cylindrical surface. This further method also includes supporting a second rotatable shaft on the second housing portion and extending a threaded portion of the second rotatable shaft along the threaded surface of the second slide member to operatively engage with the threaded surface of the second slide member and to move the second slide member in the axial direction of the second reservoir by rotation of the second rotatable shaft relative to the second slide member when the first housing portion and the second housing portion are engaged. In this further method embodiment, the drive device is also operatively coupled to the second rotatable shaft to selectively rotate the second rotatable shaft and movement of the second slide member by the rotation of the second rotatable shaft is transferred to movement of the second plunger in the axial direction of the second reservoir, when the second slide member is engaged with the second plunger.

A method for making a delivery device for delivering an infusion medium to a patient-user according to a further example embodiment also includes providing first and second housing portions, supporting a reservoir and arranging a plunger within the interior of the reservoir and movable along an axial direction of the reservoir, as described above. A method according to this further example also includes supporting arranging an end of an expandable structure for engaging the plunger and moving the plunger as the expandable structure is expanded, when the first housing portion and the second housing portion are engaged. Such a method embodiment further includes supporting a second reservoir on the second housing portion, for containing a second fluid medium for expanding the expandable structure. In addition, such a method embodiment includes coupling a conduit in fluid flow communication with the second reservoir and an interior volume of the expandable structure and operatively coupling a drive device for selectively conveying the second fluidic medium through the conduit, from the second reservoir to the interior volume of the expandable structure, to selectively expand the expandable structure, when the first housing portion and the second housing portion are engaged.

In a method according to the above-described further example embodiment, operatively coupling a drive device may include operatively coupling a peristaltic drive device to the conduit. Alternatively or in addition, operatively coupling a drive device may include supporting a rotatable rotor for rotation and arranging the rotatable rotor having a plurality of contact rollers or pads to contact a first length of the conduit as the rotor is rotated when the first and second housing portions are engaged. Such an embodiment may further include providing a support surface for supporting the first length of conduit. The support surface may be curved. Supporting a first length of the conduit may include arranging a curved surface to support the first length of the conduit, where the curved surface has a radius of curvature approximating the radius of curvature of the rotor rollers or pads. Such an embodiment also may include peratively coupling a motor to rotate the rotatable rotor. Operatively coupling a motor may include coupling a linkage structure to the motor and to the rotatable rotor, to transfer drive force from the motor to the rotatable rotor.

In any of the above-described method embodiments, the method may further include extending a drive linkage through an aperture in the second housing portion to a position to operatively connect to a connection end of the rotatable shaft when the first and second housing portions are engaged, and coupling drive linkage with the drive device, for transmitting drive force from the drive device to the rotatable drive shaft when the first and second housing portions are engaged. A seal may be arranged adjacent the aperture in the durable housing portion, to seal the aperture through which the drive linkage extends. Such method embodiments may further include providing the drive linkage with a connection end for connecting to the connection end of the rotatable shaft, and providing the connection end of the drive linkage and the connection end of the rotatable shaft with mating shapes that mate together and allow transfer of rotational motion from the drive linkage to the rotatable shaft, when the first and second housing portions are engaged.

Any of the above-described method embodiments may further include supporting electrical control circuitry on the second housing portion, where the electrical control circuitry controls the delivery of infusion medium from the reservoir to the patient-user when the first housing portion and the second housing portion are engaged. Also, in any of the above-described method embodiments, providing a first housing portion may include providing a base portion having a bottom surface and an adhesive material on the bottom surface for securing the base to the skin of the patient-user. Also, any of the above-described method embodiments may further include supporting a septum that may be pierced by a hollow needle for providing a fluid flow path from the interior of the reservoir to the hollow needle.

Also, any of the above-described method embodiments may further include providing an anti-rotation structure to inhibit the plunger from rotating within the reservoir. In such embodiments, providing an anti-rotation structure may include providing at least one projection extending from one of the plunger and the interior surface of the reservoir and providing at least one channel in the other one of the plunger and the interior surface of the reservoir, where the at least one projection is configured to extend at least partially into the at least one channel.

Any of the above-described method embodiments may further include arranging at least one seal around an outer peripheral surface of the plunger, for inhibiting the passage of infusion medium between the outer peripheral surface of the plunger and an interior surface of the reservoir.

In any of the above-described method embodiments, operatively coupling a drive device may include coupling a linkage structure to the drive device and to the rotatable shaft. Also in any of the above-described embodiments, operatively coupling a drive device may include operatively coupling a rotary motor to rotate the rotatable shaft. Alternatively, or in addition, operatively coupling a drive device may include supporting an escapement wheel for rotation, operatively connecting the escapement wheel to the rotatable shaft to rotate the rotatable shaft with rotation of the escapement wheel and operatively connecting an actuator to the escapement wheel for selectively rotating the escapement wheel.

In any of the above-described method embodiments, supporting a drive device may include supporting an escapement wheel for rotation, where the escapement wheel is operatively connected to rotate the drive linkage with rotation of the escapement wheel. Such method embodiments further include supporting a drive pawl for linear movement between a start position and an end position, where the drive pawl has a drive surface arranged to engage a tooth of the escapement wheel and rotate the escapement wheel in a first direction as the drive pawl moves between the start and end positions. Such method embodiments further include operatively connecting an actuator to the drive pawl, for selectively moving the drive pawl from the start position to the end position.

BRIEF DESCRIPTION OF THE DRAWINGS

FIG. 11a is a schematic, cross-sectional view of a portion of a reservoir and a portion of a lead shaft according to another embodiment of the invention.

FIG. 11b is a further view of the piston shaft of FIG. 11, along the longitudinal axis of the piston shaft.

FIGS. 16a-d show schematic views of escapement wheel arrangements and components thereof, for providing a controlled rotational motion.

FIG. 22 shows a perspective view of an embodiment of connection ends of the drive linkage and the rotatable shaft of FIGS. 17 and 18.

FIGS. 23 and 24 show partial cross-sectional views of reservoirs and drive devices for a delivery device according to further embodiments of the present invention.

FIGS. 37-40 each show a perspective view of yet another connection arrangement for a disposable housing portion and an injection site module.

DETAILED DESCRIPTION

The present invention relates, generally, to delivery devices, systems and methods for delivering an infusion medium, such as a drug, to a recipient, such as a medical patient-user. In particular embodiments, a delivery device includes a disposable portion that secures to the recipient and that may be readily disposed of after it has been in use for a period of time. Such embodiments may be configured to provide a reliable, user-friendly mechanism to secure the delivery device to a patient-user for delivery of a fluidic infusion medium to the patient-user.

While embodiments of the present invention are described herein with reference to an insulin delivery example for treating diabetes, other embodiments of the invention may be employed for delivering other infusion media to a patient-user for other purposes. For example, further embodiments of the invention may be employed for delivering other types of drugs to treat diseases or medical conditions other than diabetes, including, but not limited to drugs for treating pain or certain types of cancers, pulmonary disorders or HIV. Further embodiments may be employed for delivering media other than drugs, including, but not limited to, nutritional media including nutritional supplements, dyes or other tracing media, saline or other hydration media, or the like. Also, while embodiments of the present invention are described herein for delivering or infusing an infusion medium to a patient-user, other embodiments may be configured to draw a medium from a patient-user.

Figure 1:
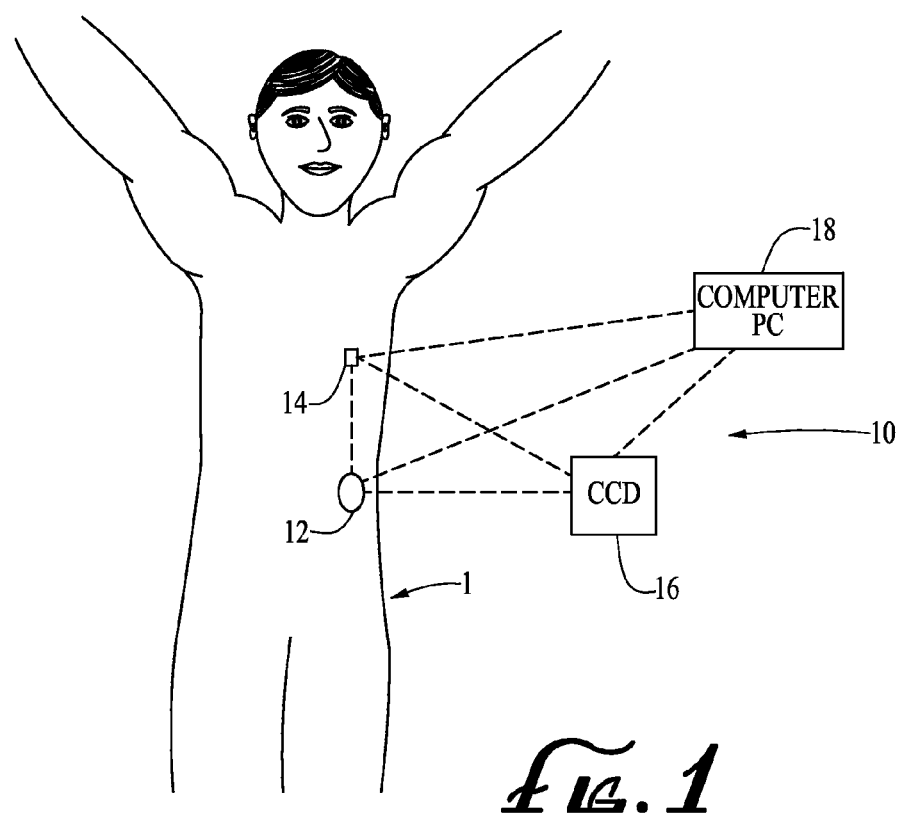
FIG. 1 is a generalized diagram of a delivery system in relation to a human patient-user.

A generalized representation of an infusion medium delivery system 10 is shown in FIG. 1, wherein the system includes a delivery device 12 configured according to an embodiment of the invention described herein. The system 10 may also include other components coupled for communication with the delivery device 12, including, but not limited to, a sensor or monitor 14, a command control device (CCD) 16 and a computer 18. Each of the CCD 16, the computer 18, the sensor or monitor 14 and the delivery device 12 may include receiver or transceiver electronics that allow communication with other components of the system. The delivery device 12 may include electronics and software for analyzing sensor data and for delivering an infusion medium according to sensed data and/or pre-programmed delivery routines. Some of the processing, delivery routine storage and control functions may be carried out by the CCD 16 and/or the computer 18, to allow the delivery device 12 to be made with more simplified electronics. However, in other embodiments, the system 10 may include delivery device 12 that operates without any one or more of the other components of the system 10 shown in FIG. 1. Examples of the types of communications and/or control capabilities, as well as device feature sets and/or program options may be found in U.S. patent application Ser. No. 10/445,477 filed May 27, 2003, and entitled "External Infusion Device with Remote Programming, Bolus Estimator and/or Vibration Alarm Capabilities," and U.S. patent application Ser. No. 10/429,385 filed May 5, 2003, and entitled "Handheld Personal Data Assistant (PDA) with a Medical Device and Method of Using the Same," U.S. patent application Ser. No. 09/813,660 filed Mar. 21, 2001, and entitled "Control Tabs For Infusion Devices And Methods Of Using The Same," all of which are incorporated herein by reference in their entirety.

In the generalized system diagram of FIG. 1, the delivery device 12 and sensor or monitor 14 are secured to a patient-user 1. The locations at which those components are secured to the patient-user 1 in FIG. 1 are provided only as a representative, non-limiting example. The delivery device 12 and sensor or monitor 14 may be secured at other locations on the patient-user 1, and such locations may depend upon the type of treatment to be administered by the system 10. Such other locations may include, but are not limited to, other locations on the patient-user's body, locations on the patient-user's clothing, belt, suspenders, straps, purse, tote or other structure that may be carried by the patient-user. Thus, while embodiments are described herein with reference to a patch-like device that secures to the patient-user's skin, other embodiments may be configured as portable devices that may be carried by the user, for example, by securing the device to an article of the user's clothing or providing additional securing structure, such as straps, tie strings, or the like, to secure to the patient-user or the patient-user's clothing or the like.

As described in further detail below, the delivery device 12 contains a reservoir of an infusion medium and delivers the infusion medium into the patient-user's body in a controlled manner. Control instructions and/or data may be communicated between the delivery device 12, the sensor or monitor 14, the CCD 16 and the computer 18. The delivery device 12 may be configured to secure to the skin of a patient-user 1, in the manner of a patch, at a desired location on the patient-user. In such embodiments, it is desirable that the delivery device 12 have relatively small dimensions for comfort and ability to conceal, for example, under a garment.

Examples of patch-like delivery devices are described in U.S. patent application Ser. No. 11/211,095, filed Aug. 23, 2005, which is incorporated herein, in its entirety. A further example of a patch-like delivery device 12 is shown in FIGS. 2-5 herein. The delivery device 12 in FIGS. 2 and 3 includes a first housing portion 20 that, in some embodiments, may be disposable after one or a number of specified uses, and a second housing portion 22 that, in some embodiments, may be a durable housing portion capable of multiple usages. The disposable housing portion 20 may support structural elements that ordinarily contact the patient-user's skin or the infusion medium, during operation of the delivery device 12.

On the other hand, the durable housing portion 22 may support elements (including electronics, motor components, linkage components, and the like) that do not ordinarily contact the patient-user or the infusion medium during operation of the delivery device 12. Thus, elements in the durable portion 22 of the delivery device 12 are typically not contaminated from contact with the patient-user or the infusion medium during normal operation of the delivery device 12.

In the illustrated embodiment, the disposable portion 20 of the delivery device 12 includes a base 21 that includes or otherwise supports a reservoir retaining portion 24 that houses a reservoir. The durable portion 22 may include a housing that secures onto the base 21 adjacent the reservoir retaining portion 24. The durable portion 22 may house a suitable drive device, such as an electrically operated motor (not shown in FIGS. 2 and 3), and drive linkage components (not shown in FIG. 2) for driving fluid out of the reservoir. The durable portion 22 also may house suitable control electronics (not shown in FIGS. 2 and 3) for controlling the operation of the drive device to drive fluid from the reservoir in a controlled manner. Further embodiments may include communication electronics (not shown in FIGS. 2 and 3) within the durable portion 22, for communicating with the sensor or monitor 14, the CCD 16, the computer 18 and/or other components of the system 10 shown in FIG. 1.

The base 21 of the disposable housing portion 20 has a bottom surface (facing downward and into the page in FIGS. 2 and 3) that is configured to secure to a patient-user's skin at a desired location on the patient-user. A suitable adhesive may be employed at the interface between the bottom surface of the base 21 and the patient-user's skin, to adhere the base 21 to the patient-user's skin. The adhesive may be provided on the bottom surface of the base portion 21, with a peelable cover layer 23 covering the adhesive material. In this manner, a patient-user may peel off the cover layer 23 to expose the adhesive material and then place the adhesive side of the base 21 against the patient-user's skin.

The disposable portion 20 may include a button or other operator 25 for operating a needle inserter device located within the reservoir retaining portion 24. Alternatively, or in addition, reference number 25 may represent an opening, through which an external needle inserter device may operate. Alternatively, or in addition to an operator or opening 25, the needle inserter device may be activated, through a wireless link, from an external controller, such as the CCD 16, sensor or monitor 14 or computer 18. For such embodiments, the CCD 16, sensor or monitor 14 or computer 18 includes a wireless signal transmitter, while the delivery device includes a receiver for receiving a wireless actuation signal and an electronic actuator that is controlled to actuate the needle inserter device, upon receipt of an actuation signal from the CCD 16, sensor or monitor 14 or computer 18. Examples of suitable needle inserter device are described in U.S. patent application Ser. No. 11/211,095, filed Aug. 23, 2005, and U.S. Patent Application No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006, each of which is incorporated herein by reference in its entirety. Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety. Alternatively, the reservoir retaining portion may include a suitable opening or port for connecting one end of a hollow tube to the reservoir, while the other end of the hollow tube is connected to a hollow needle for piercing the patient-user's skin and conveying the infusion medium from the reservoir into the patient-user, for example, as described with reference to FIG. 2 of U.S. patent application Ser. No. 11/211, 095, filed Aug. 23, 2005 and/or as described herein with reference to FIG. 29.

The durable portion 22 of the delivery device 12 includes a housing shell configured to mate with and secure to the disposable portion 20. The durable portion 22 and disposable portion 20 may be provided with correspondingly shaped grooves, notches, tabs or other suitable features that allow the two parts to easily snap together, by manually pressing the two portions together in a manner well known in the mechanical arts. In a similar manner, the durable portion 22 and disposable portion 20 may be separated from each other by manually applying sufficient force to unsnap the two parts from each other. In further embodiments, a suitable seal, such as an o-ring seal, may be placed along the peripheral edge of the disposable portion 20 and/or the durable portion 22, so as to provide a seal against water between the disposable portion 20 and the durable portion 22.

The durable portion 22 and disposable portion 20 may be made of suitably rigid materials that maintain their shape, yet provide sufficient flexibility and resilience to effectively snap together and apart, as described above. The base 21 material may be selected for suitable compatibility with the patient-user's skin. For example, the disposable portion 20 and the durable portion 22 of the delivery device 12 may be made of any suitable plastic, metal, composite material or the like. The disposable portion 20 may be made of the same type of material or a different material relative to the durable portion 22. The disposable portion and durable portions may be manufactured by injection molding or other molding processes, machining processes or combinations thereof.

The base 21 of the disposable housing portion 20 may be made of a relatively flexible material, such as a flexible silicone, plastic, rubber, synthetic rubber or the like. By forming the base 21 of a material capable of flexing with the patient-user's skin, a greater level of patient-user comfort may be achieved when the base is secured to the patient-user's skin. Also, a flexible base 21 can result in an increase in the site options on the patient-user's body at which the base 21 may be secured.

The disposable portion 20 and/or the durable portion 22 may include an internal sensor (not shown in FIGS. 2 and 3) for connection to a patient-user, for example, through a needle (not shown in FIGS. 2 and 3) or a set of micro-needles for piercing a patient-user's skin when the disposable portion 20 is secured to a patient-user's skin. In such embodiments, a suitable aperture (not shown in FIGS. 2 and 3) may be formed in the base 21, to allow the passage of the sensor needle or micro-needles, when the sensor needle is extended to pierce a patient-user's skin. Alternatively, or in addition, micro-needles may be arranged on or through the adhesive material on the base 21, to pass through the patient-user's skin, when the base 21 is adhered to the patient-user's skin. Alternatively, the durable portion 22 of the delivery device 12 may be connected to an external sensor 14, through a sensor lead, as described in U.S. patent application Ser. No. 11/211,095, filed Aug. 23, 2005. The sensor may include any suitable biological sensing device, depending upon the nature of the treatment to be administered by the delivery device 12. For example, in the context of delivering insulin to a diabetes patient-user, the sensor 14 may include a blood glucose sensor. Alternatively, or in addition, one or more environmental sensing devices may be included in or on the delivery device 12, for sensing one or more environmental conditions. In further alternatives, the sensor may be included with as a part or along side the infusion cannula and/or needle, such as for example as shown in U.S. patent Ser. No. 11/149,119 filed Jun. 8, 2005, and entitled "Dual Insertion Set," which is incorporated herein by reference in its entirety.

As described above, by separating disposable elements of the delivery device 12 from durable elements, the disposable elements may be arranged on the disposable portion 20, while durable elements may be arranged within a separable durable portion 22. In this regard, after one (or a prescribed number) of uses of the delivery device 12, the disposable portion 20 may be separated from the durable portion 22, so that the disposable portion 20 may be disposed of in a proper manner. The durable portion 22 may, then, be mated with a new (un-used, user-filled, pre-filled, refurbished, refilled or re-manufactured) disposable portion 20 for further delivery operation with a patient-user.

A reservoir 26 may be supported by the reservoir retaining portion 24 of the disposable portion 20 in any suitable manner. The reservoir 26 may be a hollow internal volume of the reservoir retaining portion 24, such as, but not limited to, a cylindrical-shaped volume as shown in broken lines in FIG. 3. Alternatively, the reservoir 26 may be a cartridge or generally cylindrical canister having a shape and size to be received within a hollow internal volume of the reservoir retaining portion. The reservoir 26 is configured for containing a fluidic infusion medium.

Figure 2:
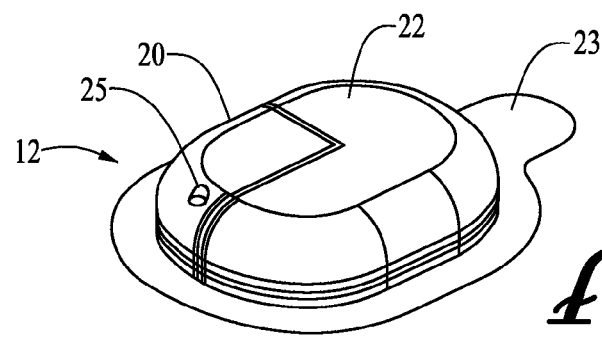
FIG. 2 is a perspective view of a delivery device according to an embodiment of the invention.

The reservoir 26 has a port and a septum. The septum is located in a position at which a hollow needle or cannula may pass through the septum and into a patient-user's skin, when the disposable housing portion 20 is secured to a patient-user's skin, as described below. In other embodiments, the port and septum of the reservoir 26 may be connectable to a patient-user, through an external needle or cannula, through a connector and external tubing, as shown in FIG. 2 of U.S. patent application Ser. No. 11/211,095, filed Aug. 23, 2005, for providing a fluid flow path between the reservoir 26 and the patient-user, when the disposable housing portion 20 is secured to a patient-user's skin. In further embodiments, the port or septum may be used (alternatively or in addition to an outlet port) for filling or re-filling the reservoir 26, for example, but not limited to, inserting a syringe through the septum and passing fluid from the syringe into the reservoir. Examples of needle/septum connectors can be found in U.S. patent application Ser. No. 10/328,393 filed Dec. 22, 2003, and entitled "Reservoir Connector," which is incorporated herein by reference in its entirety. In other alternatives, non-septum connectors such as Luer locks, or the like may be used.

The durable portion 22 of the delivery device 12 may include a motor or other force-applying mechanism, for applying a force to the infusion medium within the reservoir 26 to force the fluidic infusion medium out of the reservoir 26 and into the hollow needle or cannula (not shown in FIGS. 2 and 3), for delivery to the patient-user. For example, an electrically driven motor may be mounted within the durable portion 22 with appropriate linkage for causing the motor to operably connect to (through the linkage) a piston plunger within the reservoir and drive the piston plunger in a direction to force the fluidic infusion medium out of the reservoir port and into the patient-user. The motor may be arranged within the durable portion 22 and the reservoir 26 may be correspondingly arranged on the disposable portion 20, such that the operable connection of the motor with the reservoir piston (e.g., through appropriate linkage) occurs automatically upon the patient-user snap fitting the durable portion 22 onto the disposable portion 20 of the delivery device 12.

Figure 4:
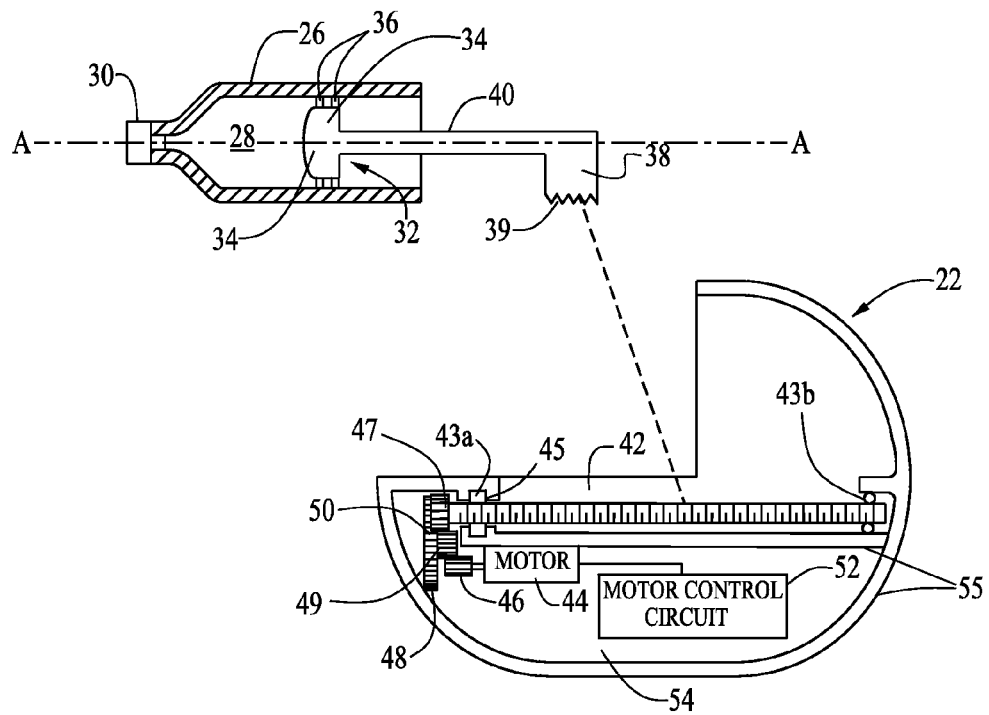
FIG. 4 is a schematic, cross-sectional view of the interior of a reservoir and a durable housing portion of a delivery device according to an embodiment of the invention.

One example of a motor and reservoir configuration is shown in FIG. 4. In the embodiment of FIG. 4, the reservoir 26 (shown in cross-section) is a canister, for example, made of a suitable metal, plastic, ceramic, glass, composite material or the like, and having a hollow interior 28 for containing a fluidic infusion medium. For example, the canister may be formed of a plastic material referred to as TOPAS (trademark of Ticona, a subsidiary of Celanese Corporation), such as described in U.S. patent application Ser. No. 11/100,188, filed Apr. 5, 2005 (Publication No. 2005/0197626), the contents of which is incorporated herein in its entirety.

Figure 3:
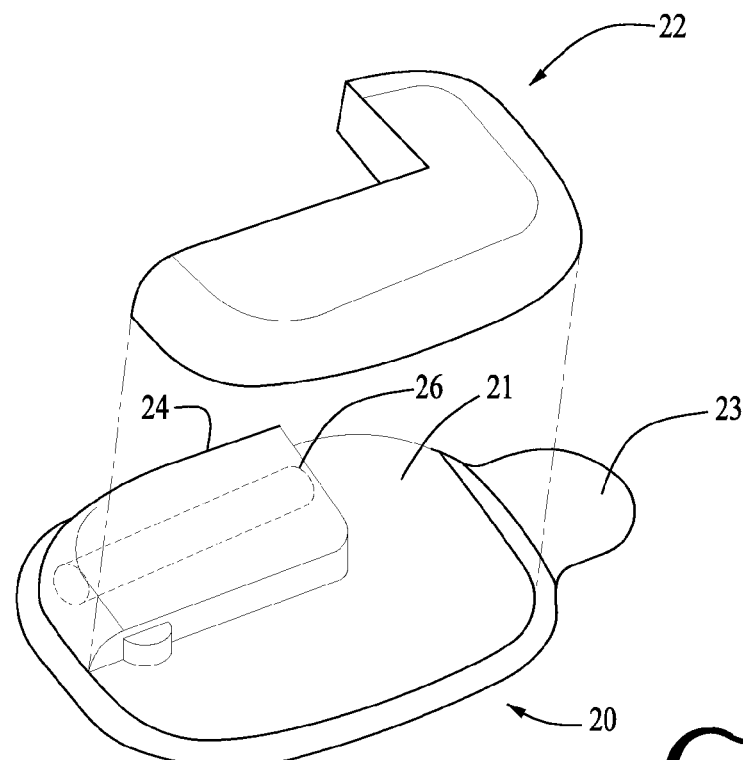
FIG. 3 is a perspective view of a durable portion and a disposable portion of the delivery device of FIG. 2, with the durable portion separated from the disposable portion.

The canister reservoir 26 in FIG. 4 may be configured to fit within and be removable from a correspondingly-shaped opening and volume in the reservoir retaining portion 24 shown in FIG. 3. In such embodiments, the canister reservoir 26 and reservoir retaining portion 24 may include one or more mating protrusions, grooves, indentations and/or non-circular cross-section that restrain the canister reservoir 26 from rotating about the axis A relative to the reservoir retaining portion 24, once the canister reservoir 26 is fitted within the reservoir retaining portion 24. In further embodiments, a canister reservoir 26 may be permanently fixed within the interior volume of the reservoir retaining portion 24.

By supporting a canister reservoir 26 in a manner that allows the reservoir 26 (and piston plunger 32) to be removed and replaced relative to the remainder of the disposable portion 20, a user may replace a spent canister reservoir 26 with a new (un-used, user-filled, pre-filled, refurbished, refilled or re-manufactured) canister reservoir 26 (and piston plunger 32), while the disposable portion remains secured to the patient-user's skin (or otherwise secured to or carried by the patient-user, in contexts in which the housing portions do not adhere to the patient-user's skin). In this manner, the same disposable portion 20 may be used for multiple new reservoirs 26 and, then, disposed of after a prescribed number of unused new, re-filled, user-filled, pre-filled, refurbished or re-manufactured reservoirs have been used on the disposable portion 20, while the same durable portion 22 may be used for multiple disposable portion 20 replacements. This also provides the user with the option to change medication delivery, by changing out and replacing reservoirs 26 with different ones containing either different medications, such as Amilyn, GLP-1, Byetta, Peptide C, insulin sensitizers, combinations of medications (with or without insulin) or the like. Alternatively, the user my change out different types of insulin (e.g., long acting, fast acting, or the like) or utilize different concentrations (U50, U100, U200, U400 or the like).

As described above, in yet further embodiments, the reservoir 26 may be formed unitarily with the reservoir retaining portion 24, for example, as a shaped, hollow interior of the reservoir retaining portion 24. In such embodiments, the hollow interior of the reservoir retaining portion 24 may be coated or otherwise lined with a suitable metal, plastic, plastic, TOPAS (trademark of Ticona, a subsidiary of Celanese Corporation), ceramic, glass, composite material or the like. Alternatively, or in addition, the retaining portion 24, itself, may be made of a suitable metal, plastic, plastic, TOPAS (trademark of Ticona, a subsidiary of Celanese Corporation), ceramic, glass, composite material or the like.

The reservoir 26 includes a septum 30 that can be pierced by a hollow needle or cannula to provide a hollow flow path from the interior 28 of the reservoir 26 to the patient-user. Examples of mechanisms that may be used for moving a hollow needle through a septum of a reservoir are described in U.S. patent application Ser. No. 11/211,095, filed Aug. 23, 2005, and U.S. Patent Application No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006. Alternatively, or in addition, the septum 30 may include a surface that is exposed through a wall of the reservoir retaining portion, for refilling the reservoir 26 or withdrawing infusion medium from the reservoir 26, for example, by piercing the exposed surface of the septum with a syringe, hollow needle or cannula. The septum 30 may be formed of a suitable material, such as, but not limited to, rubber, silicone rubber, polyurethane or other materials that may be pierced by a needle and form a seal around the needle. Examples of needle/septum connectors can be found in U.S. patent application Ser. No. 10/328,393 filed Dec. 22, 2003, and entitled "Reservoir Connector," which is incorporated herein by reference in its entirety. In other alternatives, non-septum connectors such as Luer locks, or the like may be used.

Figure 5:
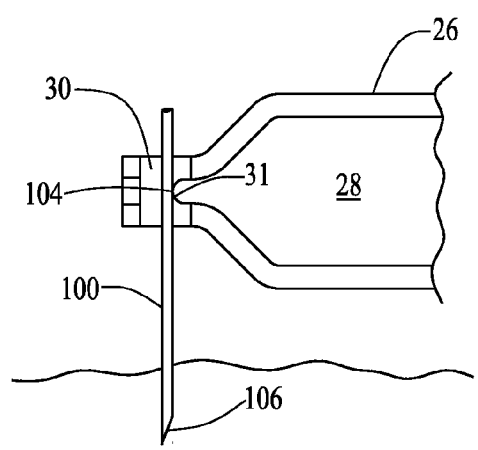
FIG. 5 is a schematic, cross-sectional view of a portion of a reservoir, showing an arrangement of a hollow needle or cannula piercing the reservoir septum and a patient-user's skin.

With reference to FIG. 5, the septum 30 may be configured such that a hollow needle or cannula 100 may be passed through the septum to create a fluid flow path between the interior 28 of the reservoir 26 and a patient-user 1. In particular, when the hollow needle or cannula 100 is passed through the septum 30, a side opening 104 in the hollow needle or cannula 100 may be aligned with a channel or indentation 31 in the septum 30 to form a fluid flow path between the hollow interior of the needle and the interior 28 of the reservoir 26. The hollow needle or cannula 100 includes a patient-end opening 106, to form a fluid flow path between the hollow interior of the needle or cannula 100 and a patient-user 1, upon the sharp end of the needle or an open end of the cannula being inserted in a patient-user's skin. Alternatively, an injection site for inserting a hollow needle or cannula into a patient-user and coupling the needle or cannula in fluid flow communication with the reservoir, as described below with reference to the injection site 132 in FIG. 15, may be employed in the embodiment of FIGS. 1-5. In further embodiments, the injection site may comprise a set of hollow micro-needles arranged to pierce a patient-user's skin, when the disposable housing portion 20 is secured to the patient-user's skin, wherein the micro-needles are connected in fluid-flow communication (for example, through a manifold structure) to the reservoir 26.

Referring again to FIG. 4, a piston plunger 32 is moveable within the interior of the reservoir, for changing the volume of the fluid-containing portion of the interior 28 of the reservoir 26. When a hollow needle or cannula is passed through the septum 30 (or a set of micro-needles are arranged in fluid flow communication with the reservoir) to form a fluid flow path from the reservoir to a patient-user, as described herein, infusion medium inside of the reservoir 26 may be expelled from the reservoir, into the patient-user, in response to a force applied by the piston plunger 32.

The piston plunger 32 extends partially into the interior of the reservoir 26 from the opposite side of the canister relative to the septum 30. The piston plunger 32 may be made of a suitably rigid material, such as but not limited to metal, plastic, ceramic, glass or composite material, and has a head 34 that has an outside diameter of slightly less than the inside diameter of the interior 28 of the reservoir 26. Alternatively, the piston plunger 32 may be made of a compressible material (such as, but not limited to, an elastically compressible plastic, rubber, silicone, or the like) and may be slightly larger in diameter than the inside diameter of the interior 28 of the reservoir 26, so as to be compressed sufficiently to fit within the interior 28 of the reservoir 26. One or more seals, such as but not limited to o-ring type seals 36, may be arranged within annular grooves provided on the piston plunger head 34. The o-ring seals 36 may be made of any suitable material, including, but not limited to rubber, plastic, metal, composite material or the like, where such o-rings provide a sealing function for inhibiting the leakage of infusion medium from the piston-plunger end of the reservoir 26. The materials from which the canister portion of the reservoir 26, piston plunger 32 and seal(s) 36 are made are preferably selected for suitable strength and durability characteristics, as well as compatibility with the infusion medium. Examples of potential piston plunger configurations may be found in U.S. Pat. No. 6,817,990 issued Nov. 16, 2004, and entitled "Improved Fluid Reservoir Piston," which is incorporated herein by reference in its entirety.

Figure 19:
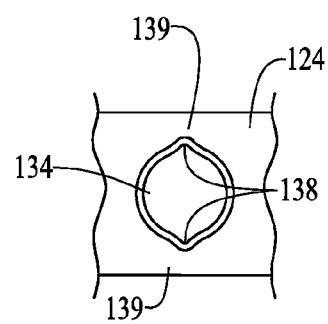
FIG. 19 shows a cross-sectional view taken along line 10-10 of FIG. 18.

The piston plunger 32 and the interior surface of the reservoir 26 may include an anti-structure, such as, but not limited to, one or more mating protrusions, grooves, indentations similar to those described below with respect to FIG. 19 and/or non-circular cross-section that restrain the piston plunger 32 from rotating about the axis A relative to the reservoir 26. Alternatively, the anti-rotation feature may include one or more seals, such as the seal(s) 36, provided that such seal(s) have sufficient frictional resistance with the interior surface of the reservoir 26 to inhibit rotation of the piston plunger 32 about the axis A, relative to the reservoir 26. For embodiments in which one or more protrusions and mating grooves are provided on the piston plunger 32 and interior surface of the reservoir 26, the protrusions and grooves may be formed with sufficiently slowly arched or curved surfaces (instead of abrupt angles or corners), to allow a seal to be readily placed over the surfaces and seal against the piston plunger 32 and interior surface of the reservoir 26. In yet further embodiments, an anti-rotation structure may be provided on the piston shaft 40 and may include any suitable structure for engaging a surface of the durable housing portion 22 or disposable housing portion 20 (or other suitable surface structure supported by the durable housing portion 22 or the disposable housing portion 20) and inhibiting rotation of the piston shaft 40 about the axis A.

The piston plunger 32 in FIG. 4 includes an engagement portion 38, located external to the interior 28 of the reservoir 26 and connected by a plunger shaft 40 to the plunger head 34. The piston plunger 32 is configured to be moveable in the axial direction A of the reservoir 26. The fluid-containing portion of the interior volume 28 of the reservoir 26 varies, with movement of the piston plunger 32 in the axial direction A of the reservoir 26. The engagement portion 38 is provided with keys, key slots or threads 39 (hereinafter referred to as threads) that are configured to operatively engage corresponding key slots, keys or threads (hereinafter, referred to as threads) on a lead shaft 42. As described in more detail below, when the engagement portion 38 is operatively engaged with the lead shaft 42 and a drive motor 44 rotates the lead shaft 42, the piston plunger 32 will move axially within the reservoir 26.

The anti-rotation structure described above inhibits the piston plunger 32 from rotating about the axis A. Accordingly, the piston plunger 32 may be arranged in, and inhibited from rotating away from, a position in which the threaded surface 39 of the engagement portion 38 faces a direction that allows the surface 39 to automatically align with and readily come into operable engagement with the lead shaft 42 when the durable portion 22 and the disposable portion 20 are arranged together for coupling.

The lead shaft 42 may be supported for rotation on the durable portion 22 of the delivery device 12. For example, one or more bearings or other suitable structure may be fixed in the durable portion for supporting the lead shaft 42 for rotation about its longitudinal axis. In the embodiment of FIG. 4, the lead shaft 42 is supported at two locations by two rotary bearings 43a and 43b. In other embodiments, the lead shaft 42 may be supported in more than two locations by more than two bearings or may be supported in a cantilevered fashion at one location by a single bearing 43a or 43b. A portion of the length of the lead shaft 42 may be exposed for engagement with the engagement portion 38 of the piston plunger 32. The lead shaft 42 extends through an opening in the durable portion 22 such that a further portion of the lead shaft 42 is located within the enclosed interior 54 of the durable portion 22, for engagement with drive linkage, as described below. One or more seals 45 may be located around the lead shaft 42, between the exposed portion of the lead shaft and the further portion of the lead shaft located in the durable portion 22. In this manner, the seal(s) 45 may inhibit fluid from entering the opening in the durable portion 22 through which the lead shaft 42 extends. The seal(s) 45 may be made of any suitable seal material, including, but not limited to silicone or other flexible plastic, metal, ceramic, composite material or the like. In further embodiments, the seal(s) 45 may comprise a material and/or seal configuration that provides a liquid-tight seal, but allows the passage of air to allow equalization of pressure between the interior 54 of the durable housing portion 22 and the environment exterior of the durable housing portion 22. In yet other embodiments, a pressure equalization port opening may be provided in any suitable location of the durable housing portion, to provide air-flow communication between the interior 54 and exterior of the durable housing portion. In such embodiments, the air-flow communication port may be covered with a material that allows the passage of air, but inhibits the passage of water or other liquids. Examples of structures that permit air-flow, but that inhibit fluids can be found in U.S. patent application Ser. No. 10/328,393 filed Dec. 22, 2003, and entitled "Reservoir Connector," and U.S. patent application Ser. No. 10/699,429 filed Oct. 31, 2003, and entitled "External Infusion Device with a Vented Housing," both of which are incorporated herein by reference in their entirety.

A drive motor 44 is mechanically coupled to the lead shaft 42, to drive the lead shaft in a rotary motion about its longitudinal axis, in a controlled manner. The motor 44 may be coupled to the lead shaft 42 through one or more suitable gears, belts, chains, drive shafts or other linkage structure. The linkage structure may be configured to provide a torque conversion, for example, to increase torque and decrease rotational speed at the lead shaft, relative to the torque and speed output of the motor 44. Accordingly, the motor 44 may produce relatively high-speed rotational motion, which may be converted through the linkage structure to a lower speed of rotation, but higher torque applied to the lead shaft.

In the embodiment illustrated in FIG. 4, the motor 44 includes a drive gear 46, while the shaft 42 is provided with an engagement gear 47. A linking gear 48 is arranged between the drive gear 46 and the engagement gear 47, to convey rotary drive force from the motor 44 to the shaft 42. The linking gear 48 in FIG. 4 includes hub portion 49 for engaging the drive gear 46, and a main portion 50 for engaging the engagement gear 47. The hub portion 49 is fixed to the main portion 50 and has a smaller diameter than the main portion 50.

In other embodiments, a linking gear 48 may be arranged such that a smaller diameter hub portion engages the engagement gear 47, while a larger diameter main portion engages the drive gear 46. In yet further embodiments, additional gears may be interposed between some or each of the gears 46, 47 and 48, to convey rotational motion from the motor 44 to rotational motion of the lead shaft 42. In yet further embodiments, the linking gear 48 may be eliminated and the drive gear 46 may be arranged to directly engage the engagement gear 47. In yet further embodiments, other linkage structure may be employed to operatively link the motor 44 to the lead shaft 42. Further examples of linkage and control structures may be found in U.S. patent application Ser. No. 09/813,660 filed Mar. 21, 2001, and entitled "Control Tabs For Infusion Devices And Methods Of Using The Same," which is incorporated herein by reference in its entirety.

Figure 6:
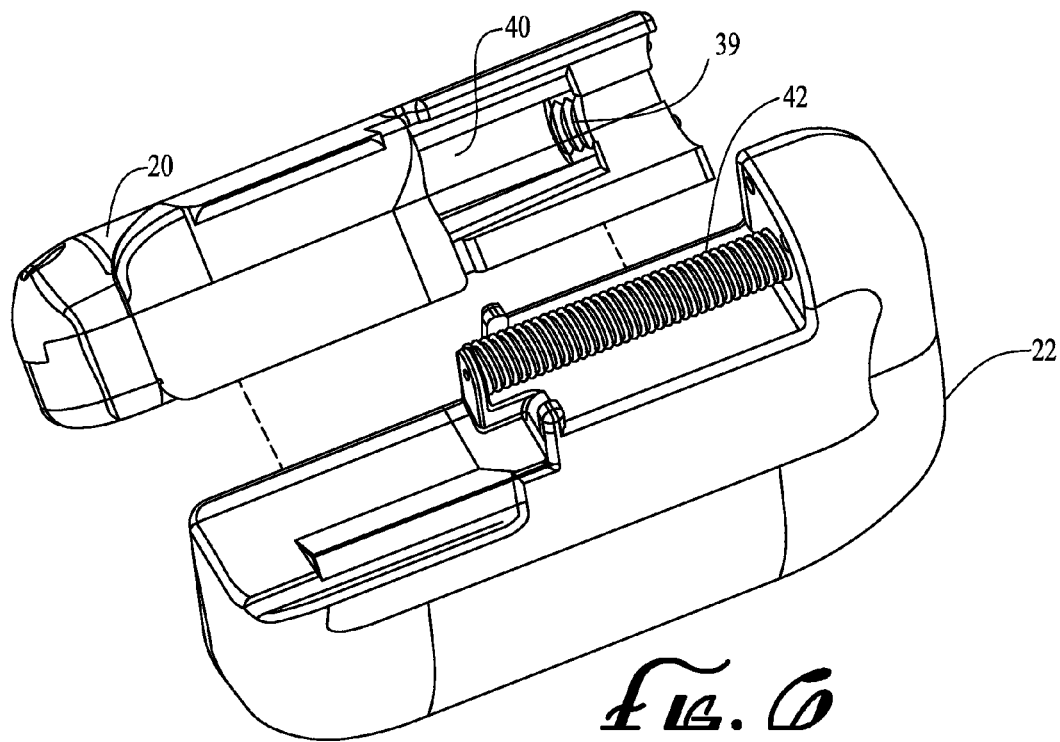
FIG. 6 is a perspective view of a durable portion separated from a disposable portion of a delivery device having a reservoir, piston plunger and lead shaft configuration that engage in a manner similar to that of FIG. 4.
Figure 7:
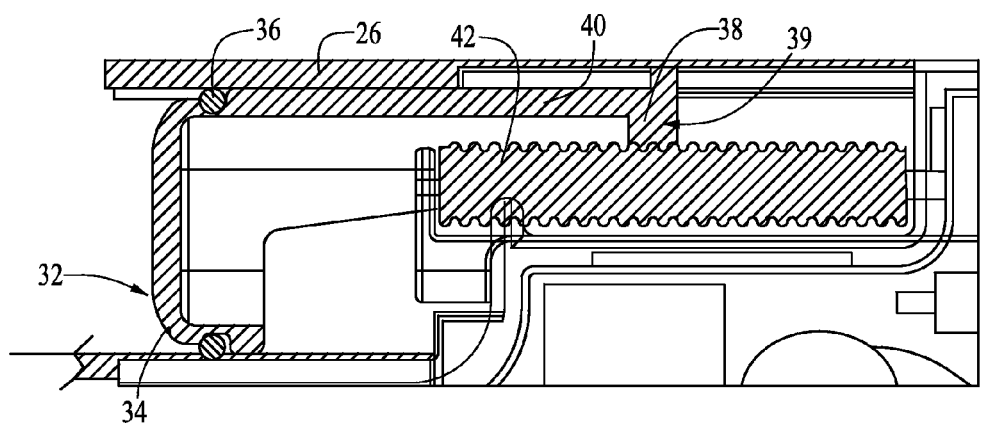
FIG. 7 is a schematic, cross-section view of the piston plunger and lead shaft of FIG. 6, in an engaged state.

FIGS. 6 and 7 shows a further example embodiment of delivery device having a piston plunger 32, lead shaft 42 and reservoir 26, similar to piston plunger, lead shaft and reservoir described above with respect to FIG. 4. Referring to FIGS. 6 and 7, the reservoir 26 may be arranged in a first or disposable housing portion 20 (similar to the disposable housing portion described above), while the lead shaft 42 may be supported by the second or durable housing portion 22 (similar to the durable housing portion described above). In the embodiment in FIGS. 6 and 7, the piston plunger 32 has a piston head 34 located within the reservoir 26 and a piston shaft 40 that extends from the peripheral edge of the piston head 34 to a location outside of the reservoir 26. One or more seals 36 (for example, similar to seals 36 described above) may be included around the outer peripheral surface of the piston head 34, for sealing against the interior surface of the reservoir 26. A partial-nut engagement portion 38 is provided with threads 39 on a arched surface. The arched surface of the engagement portion 38 curves around the longitudinal axis of the lead shaft 42 to allow the threads 39 to readily operatively engage with threads on the lead shaft 42 as a partial nut (threading partially, but not fully around the shaft), when the disposable housing portion 20 and the durable housing portion 22 are engaged. The arched or curved surface of the threads 39 on the engagement portion 38 allow the engagement portion 38 to easily fit over a portion of the lead shaft 42 and operatively engage the threads on the lead shaft 42 by simply bringing the disposable housing portion 20 and the durable housing portion 22 together in operative engagement.

In FIG. 6, the disposable housing portion 20 and the disposable housing portion 22 are shown as being separated (for example, just before the disposable housing portion 20 and the durable housing portion 22 are brought together for operative engagement). In FIG. 7, the disposable housing portion 20 and the durable housing portion 22 are engaged, such that the threads on the engagement portion 38 on the piston plunger 32 is operatively engaged with the threads on the lead shaft 42. The piston plunger 32, including the piston head 34, the piston shaft 40 and the engagement portion 38 may be configured as a single, unitary member, for example, by molding, machining, or other suitable manufacturing technique, for example, for cost-efficiency. Alternatively, the piston plunger 32 may be configured as a multi-piece member that is assembled to form a piston plunger 32.

Figure 8:
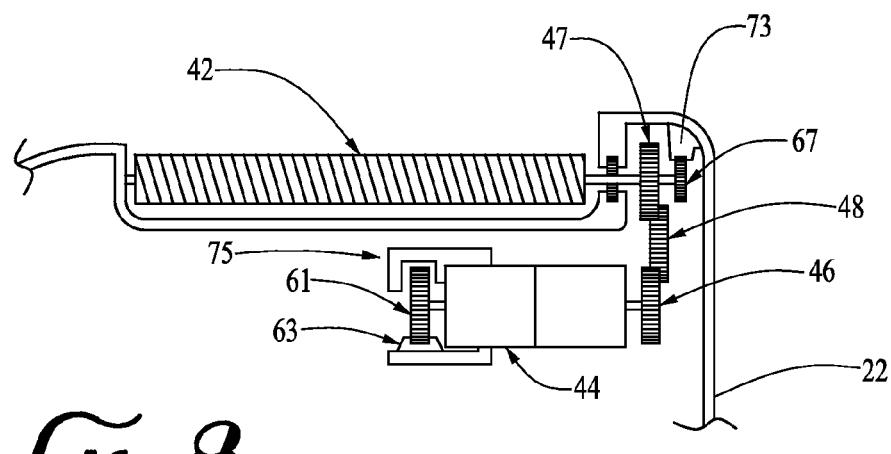
FIG. 8 is a schematic, side view of a motor and linkage structure that may be employed with the embodiments of FIGS. 4, 6 and 7.
Figure 9:
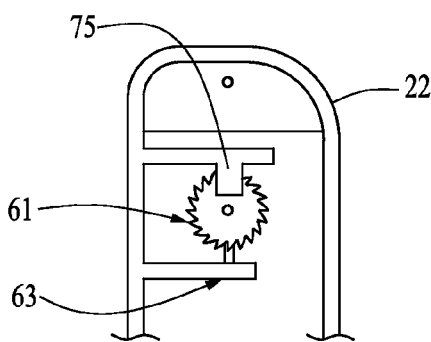
FIG. 9 is a side view of the motor and linkage structure of FIG. 8, as viewed from the left side of FIG. 8.
Figure 10:
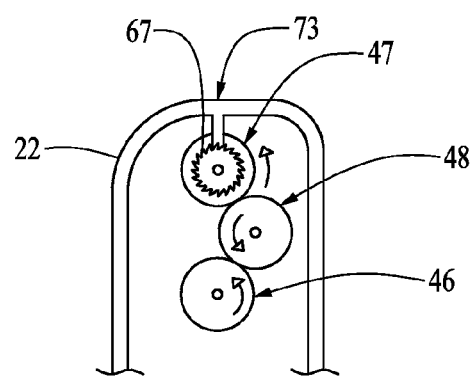
FIG. 10 is a side view of the motor and linkage structure of FIG. 8, as viewed from the right side of FIG. 8.

An example embodiment of a motor 44 and linkage structure for operatively coupling the motor 44 to the lead shaft 42 is shown in FIGS. 8, 9 and 10, where FIG. 9 is a view of the structure of FIG. 8, as viewed from the left side of FIG. 8. Similarly, FIG. 10 is a view of the structure of FIG. 8, as viewed from the right side of FIG. 8. (The orientation of the linkage gears and motor relative to the lead shaft in FIG. 8 is shown as an opposite or a mirror-image of the orientation shown in FIG. 4, but otherwise is structurally similar to the arrangement in FIG. 4.) In the embodiment of FIGS. 8, 9 and 10, one or more of the motor and the linkage structure may be provided with an anti-reverse rotation structure, to inhibit rotation of the lead screw in a direction opposite to the normal drive direction (e.g., opposite to the direction at which the piston plunger is moved to force fluid out of the reservoir). Such anti-reverse rotation structure may include a ratchet wheel and stop surface arrangement.

For example, in the embodiment of FIGS. 8, 9 and 10, the motor 44 is provided with a motor escapement wheel 61 on a common motor drive shaft as the drive gear 46 of the motor. The escapement wheel 61 may include ratchet teeth arranged to ride over a stop surface 63 when the escapement wheel is rotated in the normal drive direction, but that abut the stop surface and inhibit rotation of the motor drive shaft in a direction opposite to the normal drive direction. In a further embodiment, an escapement wheel may be provided in the linkage structure, such as on a common rotary shaft as one of the gears in the linkage structure. In the embodiment in FIGS. 8, 9 and 10, a second escapement wheel 67 is provided on the same rotary shaft of the lead shaft gear 47. A stop surface 73 is arranged relative to the escapement wheel 67 to allow the ratchet teeth on the escapement wheel 67 to ride over the stop surface 73, when the lead shaft 42 is rotated in a normal drive direction, but inhibit rotation of the escapement wheel in a direction opposite to the normal drive direction.

The anti-reverse rotation structure may be provided to inhibit un-intended reverse movement of the piston plunger within the reservoir, for example, due to an improperly aligned motor poles, improper handling of the lead shaft, or the like. A rotation sensor may be associated with either one or both of the escapement wheels 61 and 67. In the embodiment of FIGS. 8, 9 and 10, a rotation sensor in the form of a sensor 75 is arranged adjacent the escapement wheel 61 to sense rotation of the escapement wheel 61. The sensor 75 may be any suitable rotation sensor including, but not limited to an optical sensor for sensing optical elements (reflecting or non-reflecting surface features) on the escapement wheel 61, as the wheel 61 is rotated.

In FIGS. 4 and 6-10, the drive gear 46, the linking gear 47 and engagement gear 48 form a gear train for transferring motor drive force from the motor 44 to the lead shaft 42. In this manner, as the motor rotatably drives the motor drive shaft, the gear train transfers the motor drive force to rotate the lead shaft 42. When the piston plunger 32 is engaged with the lead shaft 42, rotation of the lead shaft 42 causes the engagement portion 38 of the piston plunger 32 to ride along a portion of the threaded length of the lead shaft 42. In this manner, the rotation of the lead shaft 42 is transferred to an axial movement of the piston plunger 32, when the piston plunger is engaged with the lead shaft 42. The available length of travel of piston plunger 32 is dependant upon the length of the threaded portion of the lead shaft 42, the length of the piston plunger shaft 40 and the starting location of the engagement portion 38 of the piston plunger along the threaded length of the lead shaft 42.

The lead shaft 42 may be provided with threads along most or all of the length of the exposed portion of the shaft, to allow operable engagement of the threads on the engagement portion 38 to the corresponding threads on the lead shaft 42 at any location along the length of the exposed portion of the lead shaft 42. As described above, to further assist the operable engagement of the threads on the engagement portion 38 to the corresponding threads on the lead shaft 42, the engagement portion 38 may be provided with an arcuate surface on which the threads are arranged. The threaded arcuate surface of the engagement portion 38 may extend around one half or less (180 degrees or less) of the circumference of the lead shaft 42, when the engagement portion 38 is engaged with the lead shaft 42, i.e., when the durable housing portion and disposable housing portion are engaged as shown in FIG. 2. In further embodiments, the threaded arcuate surface of the engagement portion 38 may extend around a little more than one half (more than 180 degrees) of the circumference of the lead shaft 42 and may be composed of sufficiently resilient, flexible material to provide a snap-fit with the lead shaft, when the engagement portion 38 is engaged with the lead shaft 42, i.e., when the durable housing portion and disposable housing portion are engaged as shown in FIG. 2. Other types of drive engagement structures that may be used are shown in U.S. patent application Ser. No. 10/379,627 filed Mar. 5, 2003, and entitled "Leadscrew Driven Syringe With Integral Plunger Nut," and U.S. Pat. No. 5,954,697 issued Sep. 19, 1999, and entitled "Threaded Nut Syringe Plunger For Use With A Medication Infusion Pump," both of which are incorporated herein by reference in their entirety.

In other embodiments as represented in FIG. 11a, the piston plunger shaft 40 may be provided with teeth (or threads) along its length and the lead shaft 42 may have a disk-shaped threaded head portion 41 that may be relatively short in length in the axial direction A. The threaded head portion 41 has threads on its outer peripheral surface to engage the teeth (or threads) of the piston plunger shaft 40, for example, in a rack and pinion type of an arrangement, wherein the piston plunger shaft 40 may include a toothed rack and the threaded head portion 41 may function as a pinion gear. In embodiments as shown in FIG. 11b, the piston plunger shaft 40 may be provided with an arcuate surface 51 on which the teeth (or threads) are located. The arcuate surface 51 extends along the longitudinal dimension of the piston plunger shaft 40, outside of the interior portion of the reservoir and arcs partially around the axis of the lead shaft 42, to engage the head portion 41, when the durable housing portion and the disposable housing portion are engaged as shown in FIG. 2. The radius of the arcuate surface 51 may approximate the radius of the disk-shaped head 41, to allow the head 41 to readily, operatively engage the piston plunger shaft and to increase the surface area of engagement between those components, when the durable housing portion and disposable housing portion are engaged as shown in FIG. 2.

Similar to the arcuate surface of the engagement portion 38 in FIG. 4 described above, the arcuate surface 51 of the piston plunger shaft 40 in FIGS. 11a and 11b may extend around one half or less (180 degrees or less) of the circumference of the lead shaft 42, when the piston plunger shaft 40 is engaged with the lead shaft 42, i.e., when the durable housing portion and disposable housing portion are engaged as shown in FIG. 2. In further embodiments, the arcuate surface 51 of the piston plunger shaft 40 may extend around more than one half (more than 180 degrees) of the circumference of the lead shaft 42 and may be composed of sufficiently resilient, flexible material to provide a snap-fit with the lead shaft, when the piston plunger shaft 40 is engaged with the lead shaft 42, i.e., when the durable housing portion and disposable housing portion are engaged as shown in FIG. 2.

In the embodiments of FIGS. 4, 6, 7 and 11a and 11b, one of the lead shaft 42 or the piston plunger shaft 40 includes a threaded portion extending a length along the direction of axis A, beyond the length in the direction of axis A of the fluid containing portion 28 of the reservoir 26. The piston plunger shaft 40 may be provided with threads along most or all of the length of the exposed portion of the shaft, to allow operable engagement with the lead shaft 42 or threaded head portion 41, at any location along the length of the exposed portion of the piston plunger shaft 40.

A motor 44, lead shaft 42 and any linkage between the motor and lead shaft may be supported by the durable portion 22 of the delivery device in a location at which the threaded portion of the shaft 42 engages the threaded portion of the piston plunger 32, as shown in FIGS. 4, 7, 8 or 11a. In this manner, when the durable portion 22 is arranged to be secured (such as by snap fitting, friction fitting or other suitable engagement configuration) onto the disposable portion 20, the threaded portion of the shaft 42 operatively engages the threaded portion of the piston plunger 32 without requiring further user manipulation of the elements. In other embodiments, additional manipulation of the housing portions and/or a manual operator may be required to operatively engage the threaded portion of the shaft 42 with the threaded portion of the piston plunger 32, while or after the durable portion 22 is arranged to be secured (such as by snap fitting, friction fitting or other suitable engagement configuration) onto the disposable portion 20.

While not shown in FIGS. 4 and 6, the motor 44 may be provided with electrical terminals for connection to a motor control circuit (e.g., motor control circuit 52 shown in FIG. 4 or a similar motor control circuit, not shown, in the durable housing portion 22 of FIG. 6. The motor control circuit 52 may be mounted within the durable portion 22 of the delivery device, for controlling the operation of the motor according to a desired infusion delivery program or profile. A delivery program or profile may be stored within a suitable electronic storage medium (not shown) located within the durable portion 22 and/or may be communicated to the delivery device 12 from other sources, such as a CCD 16 or a computer 18 (as shown in FIG. 1). In such embodiments, the delivery program or profile may be employed by the motor control circuit 52 to control the operation of the motor 44 in accordance with the delivery program or profile. Alternatively or in addition, the motor control circuit 52 may control the motor 44 to deliver one or more discrete volumes of infusion medium in response to delivery demand control signals generated within the device 12 or communicated to the device 12 from other sources, such as a CCD 16, sensor or monitor 14 or a computer 18 (as shown in FIG. 1).

The durable portion 22 may contain additional electronic circuitry (not shown) for communication with external devices such as the CCD 16 or computer 18, for storage of sensor data or other data, for processing and control functions, or for other functions. The durable portion 22 may have a user interface (not shown) including one or more buttons, electronic display (including, but not limited to, an LED display, an LCD display or other suitable electronic display), or the like, to allow a user to access data and/or input data or instructions to control electronic circuitry within the durable portion 22. Examples of the types of communications and/or control capabilities, as well as device feature sets and/or program options may be found in U.S. patent application Ser. No. 10/445,477 filed May 27, 2003, and entitled "External Infusion Device with Remote Programming, Bolus Estimator and/or Vibration Alarm Capabilities," and U.S. patent application Ser. No. 10/429,385 filed May 5, 2003, and entitled "Handheld Personal Data Assistant (PDA) with a Medical Device and Method of Using the Same," both of which are incorporated herein by reference in their entirety.

In some embodiments, the durable portion 22 may contain a battery, high energy capacitor or other electronic power source (not shown) for providing electrical power to the motor 44, motor control circuit 52 and other electronic circuitry contained in the durable portion 22. In such embodiments, the battery, high energy capacitor or other electronic power source may be rechargeable through a recharge connector (not shown) provided on the durable portion 22. In other embodiments, a battery, capacitor or other electronic power source (not shown) may be supported on the disposable portion 20 and connectable to the motor 44, motor control circuit 52 and other electronic circuitry in the durable housing portion, through electrical connectors that make an electrical connection upon the durable portion 22 being coupled to the disposable portion 20, without additional manual manipulation. Such electrical connectors may include one or more pairs of conductive pads, where each pair of pads is connected to opposite poles of the power source and located on any suitable surface of the disposable portion 20 that engages a corresponding surface on the durable portion 22, when the durable portion 22 is coupled in engagement with the disposable portion 20. In such embodiments, the corresponding surface of the durable portion 22 includes one or more corresponding pairs of conductive pads that are electrically connected to the motor 44, motor control circuit 52 and other electronic circuitry in the durable housing portion and are arranged to engage the conductive pads on the disposable portion, when the durable portion 22 is engaged with the disposable portion 20. In other embodiments, further manual manipulation of the housings and/or a manual operator may be required to complete the electrical connection, once the durable portion 22 and the disposable portion 20 are engaged.

The durable portion 22 includes an interior volume 54 that contains the motor 44, gears 46-48, motor control circuit 52, other electronic circuitry and, in some embodiments described above, a power source. To protect those electrical and mechanical components from certain environmental conditions (such as, but not limited to, moisture, air, biological or medical fluids), the interior volume 54 of the durable portion 22 may be suitably sealed from the external environment by the housing structure 55 that forms the durable portion 22 and the seal(s) 45 for the opening through which the lead shaft 42 extends. Accordingly, the housing structure of the durable portion 22 and the seal(s) 45 may form a suitable moisture-tight seal, air-tight seal and/or hermetic seal, to protect the electronic components located in the interior volume 54 and/or separate those components from environmental, medical or biological materials to which the disposable portion 20 is exposed during normal operation. The gear train composed of gears 46, 47 and 48, may be included in the sealed interior volume 54, to protect and/or separate those mechanical components from environmental or biological materials, as well.

As discussed above, in the arrangement illustrated in FIGS. 2, 3, 4, 6, 7 and 11, the durable portion 22 may be attached (for example, snap fitted, friction fitted, or the like) onto the disposable portion 20, where the threaded portion of the lead shaft 42 automatically engages the threaded portion of the piston plunger 32 without requiring further user manipulation of the elements. In further embodiments, further user manipulation may be required for the lead shaft 42 to engage the threaded portion of the piston plunger 32. In the embodiment of FIGS. 4, 6 and 7, the threaded surface 39 of an engagement portion 38 of the piston plunger 32 may have an arcuate surface that curves around a portion of the longitudinal axis of the lead shaft 42. By providing the surface of the engagement portion 38 of the piston plunger 32 with an arcuate shape that curves around a portion of the longitudinal axis of the lead shaft 42, the surface area of the surface 39 that engages the lead shaft 42 may be increased. In addition, the curvature of the surface 39 of the engagement portion 38 around a portion of the longitudinal axis of the lead shaft 42 can help to inhibit inadvertent separation of the engagement portion 38 and the lead shaft 42, once the engagement portion 38 is engaged with the lead shaft 42. The curvature of the surface 39 also may allow the engagement portion 38 to easily align with and operably engage the lead shaft 42, by bringing the lead shaft 42 into contact with the engagement portion 38 as a consequence of the manual operation of coupling the durable portion 22 to the disposable portion 20.

Figure 12:
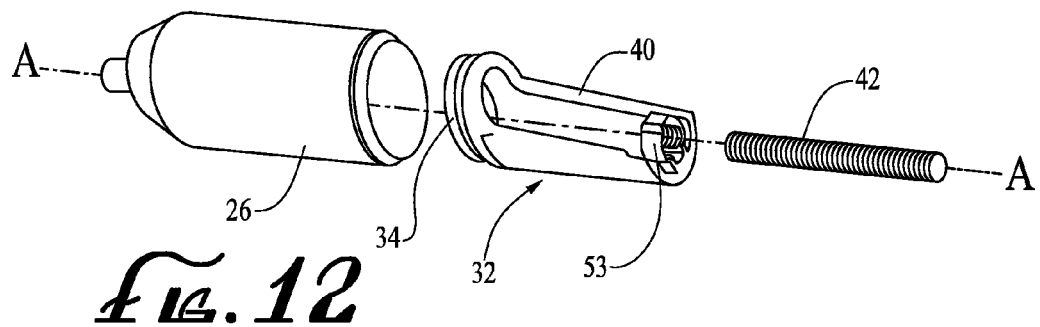
FIG. 12 is a perspective view of an embodiment of a reservoir, piston plunger and lead shaft suitable for the delivery device embodiments of FIGS. 4, 6 and 7.
Figure 13:
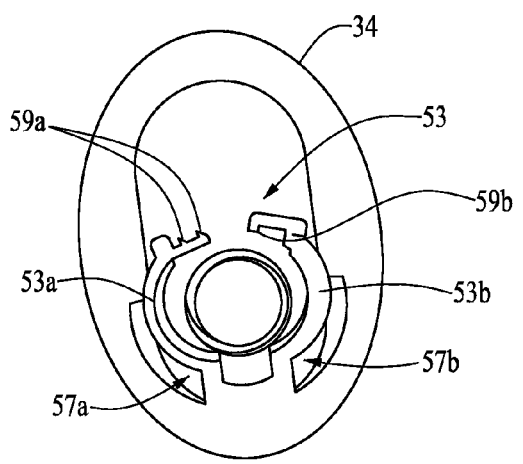
FIG. 13 is an axial view of the piston plunger of FIG. 12, with the clip open.
Figure 14:
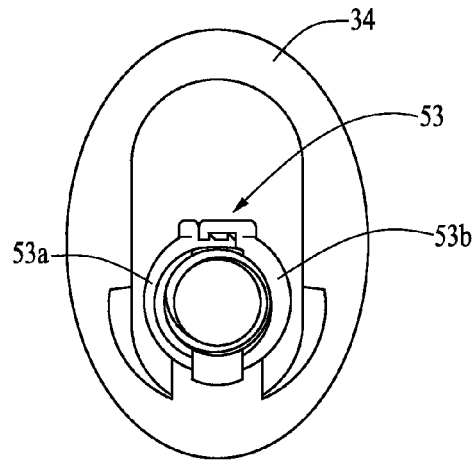
FIG. 14 is an axial view of the piston plunger of FIG. 12, with the clip closed.
Figure 15:
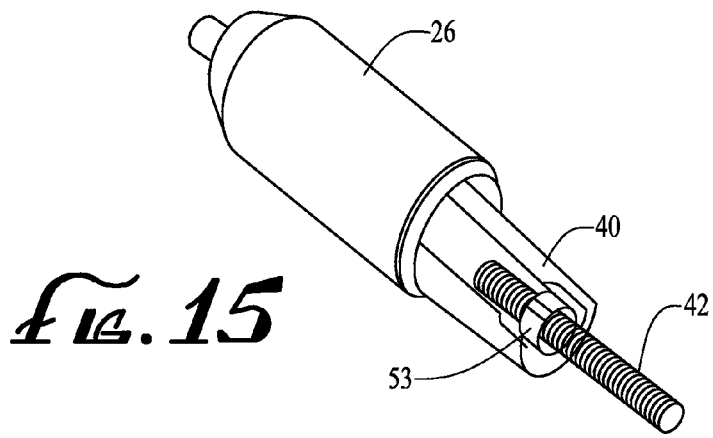
FIG. 15 is a perspective view of the piston plunger of FIG. 12 assembled with the reservoir of FIG. 12, and with the lead shaft of FIG. 12 in operable engagement with the piston plunger.

FIGS. 12-15 show a further example embodiment of a piston plunger 32 and lead shaft 42 configured for operable engagement, upon engagement of the disposable housing portion 20 and the durable housing portion 22. FIG. 12 is a perspective view of an embodiment of a reservoir, piston plunger and lead shaft suitable for the delivery device embodiment of FIG. 4. FIG. 13 is an axial view of the piston plunger of FIG. 12, with the clip open, while FIG. 14 is an axial view of the piston plunger of FIG. 12, with the clip closed. FIG. 15 is a perspective view of the piston plunger of FIG. 12 assembled with the reservoir of FIG. 12, and with the lead shaft of FIG. 12 in operable engagement with the piston plunger.

In the embodiment of FIGS. 12-15, the piston plunger 32 includes an oval-shaped piston head 34, having a shape and size for fitting within the correspondingly-shaped interior of the reservoir 26. The oval shape of the piston head 34 and the interior of the reservoir 26 inhibit rotation of the piston head 34 relative to the reservoir 26, when the piston head 34 is fitted within the interior of the reservoir 26.

The piston plunger 32 in the embodiment of FIGS. 12-15 includes a piston shaft 40 that has concave surface extending along the axial dimension A, that forms a trough shaped curvature, curving partially around the axis A. The trough-shaped curvature of the piston shaft 40 provides a receptacle for receiving the lead shaft 42, when the disposable housing portion 20 and the durable housing portion 22 are engaged. The piston shaft 40 includes at least one clip 53, for operatively engaging the lead shaft 42, when the disposable housing portion 20 and the durable housing portion 22 are engaged. While the embodiment of FIGS. 12-15 is shown with one clip 53, other embodiments may include two or more clips along the axial length A of the piston shaft 40.

The clip 53 includes a pair of clip arms 53a and 53b, each of which are flexible and/or pivotal between an open state (shown in FIG. 13) and a closed state (shown in FIG. 14). In the embodiment of FIGS. 12-15, the clip arms 53a and 53b each have a pivot point or flexible hinge portion 57a and 57b, respectively, to allow the arms 53a and 53b to pivot about an axis that is substantially parallel to the axis A, between the open and closed states. One or both of the clip arms includes threads that are of a suitable size and pitch to operatively engage with the threads on the lead shaft 42. When in an open state, each clip arm 53a and 53b has a free end that is spaced apart from the free end of the other clip arm. When in the closed state (FIG. 14), the free ends of the clip arms 53a and 53b engage and may partially overlap.

The free ends of the clip arms 53a and 53b may include locking structure for allowing the clip arms to lock together, when the free ends of the clip arms 53a and 53b are brought together, by flexing or pivoting the clip arms 53a and 53b about the pivot point or flexible hinge portion 57a and 57b, respectively. Such locking structure may include one or more protrusions 59a and 59b adjacent the free end of each clip arm 53a and 53b, respectively, where the protrusions 59a and 59b provide stop surfaces that abut each other when the free ends of the clip arms 53a and 53b are brought together, with one clip arm (e.g., clip arm 53b) partially overlapping the other clip arm (e.g., clip arm 53a).

In one embodiment, the clip arms 53a and 53b are biased (for example by a spring or a natural spring force of the material from which the clip arms are made) toward the closed position, but are held in an open position (as shown in FIG. 13) by a releasable lock mechanism. The lock mechanism may be released, for example, by the action of the lead shaft 42 engaging the flexible hinge portion 57a and 57b of one or both clip arms 53a and 53b. In other embodiments, the lock mechanism may be released by a manual operator (not shown), operable from outside of the disposable housing portion 20 and the durable housing portion 22, when those housing portions are engaged. In yet other embodiments, the clip arms 53a and 53b may be configured to be in an open position (as shown in FIG. 13) by the natural spring force of the material that forms the clip arms (or by a further bias member, such as a separate spring), and may be closed by the manual operation of engaging the disposable housing portion 20 with the durable housing portion 22, for example by squeezing the arms 53a and 53b together by sliding the arms in engagement with a diverging pair of walls or other structure in the durable housing portion 22 after the engagement portion 38 of the piston plunger 32 is manually aligned to engage with the lead shaft 42. In yet other embodiments, the clip arms 53a and 53b may be biased toward a closed position (by the natural spring force of the arms or by a separate bias member, such as a spring), while a stop member maintains the arms 53a and 53b in an open position (as shown in FIG. 13) prior to assembly of the disposable housing portion 20 with the durable housing portion 22. In such an embodiment, a stop release mechanism may be employed to release the arms 53a and 53b from the stop member and allow the arms 53a and 53b to close around the lead shaft 42, after the engagement portion 38 of the piston plunger 32 is manually aligned to engage with the lead shaft 42. In such an embodiment, the stop release mechanism may comprise an automatic structure that moves the stop member (or moves the arms 53a and 53b relative to the stop member) to automatically release the arms 53a and 53b by the manual action of engaging the disposable housing portion 20 with the durable housing portion 22. Alternatively, the stop release mechanism may comprise a further manual operator that requires a further manual operation (pushing a button, moving a lever or the like) to release the stop member and allow the arms 53a and 53b to move to their closed position.

In operation, as the durable housing portion 22 is manually brought into engagement with the disposable housing portion 20, the lead shaft 42 on the durable housing portion is aligned with the axial dimension A of the piston shaft 40 and is brought into a position between the open clip arms 53a and 53b. Either by automatic operation or by manual operation of the clip arms 53a and 53b, the clip arms 53a and 53b are flexed or pivoted from the open state to the closed state, to operatively engage the threads on the clip arms with the threads on the lead shaft 42, as shown in FIG. 15. Once engaged, rotation of the lead shaft 42 causes the piston plunger 32 to move in the axial dimension A, within the interior of the reservoir 26.

As described above, when the durable portion 22 and the disposable portion 20 are fitted together with the lead shaft 42 engaging the engagement portion 38 of the piston plunger 32, the motor 44 may be controlled to rotatably drive the lead shaft 42 and, thus, move the piston plunger 32 in the axial direction A of the reservoir 26. When the interior volume of the reservoir 26 is filled with an infusion medium and a hollow needle or cannula is positioned in a septum of the reservoir (for example, similar to septum 30 discussed above) to form a fluid flow path between the reservoir 26 and a patient-user, the piston plunger 32 may be controlled to move in the axial direction A, toward the septum 30 end of the reservoir 26, to force infusion medium from the reservoir volume 28, through the hollow needle or cannula and into the patient-user.

Once the reservoir 26 has been sufficiently emptied or otherwise requires replacement, the patient-user may simply unsnap and remove the durable portion 22 from the disposable portion 20 of the delivery device 12 and replace the disposable portion 20 (including the reservoir) with a new disposable portion having an unused new, user-filled, prefilled, refurbished, remanufactured or re-filled reservoir 26. The durable portion 22 may be engaged to the new disposable portion and the delivery device (including the new disposable portion) may be secured to (or otherwise carried by) the patient-user, as described above.

In further embodiments in which the reservoir 26 includes a reservoir canister that fits within a hollow interior of the reservoir retaining portion 24, the canister may be removed from the retaining portion 24 and replaced with an unused new, user-filled, prefilled, refurbished, remanufactured or re-filled canister, to allow the disposable portion 22 to remain in place on a patient-user for more than one reservoir depletion period. In such embodiments, the reservoir canister may be replaced one or more times during the operable life of the disposable portion 20 and the disposable portion 20 may be removed from the patient-user and replaced with a new or remanufactured disposable portion 20, for example, after a predefined number of reservoir canister replacement operations.

The drive motor 44 in FIG. 4 (or any of the embodiments described herein) may include any suitable rotary drive device that converts electrical power to mechanical, rotary motion. Examples of a suitable rotary drive motor 44 include, but are not limited to, a DC motor, flat or pancake DC motor, servo motor, stepper motor, electronically commutated motor, rotary piezo-electrically actuated motor, and the like. In further embodiments, the drive motor 44 may include a bender or linear actuator in combination with an escapement wheel arrangement, to rotatably drive the lead shaft 42. For example, a drive device for rotatably driving the lead shaft 42 may include a piezo-electrically actuated bender and escapement wheel arrangement, a thermally actuated bender and escapement wheel arrangement, a shape memory alloy wire and escapement wheel arrangement, an electronically actuated solenoid and escapement wheel arrangement, or the like. Examples of shape memory alloy wire drive systems may be found in U.S. Pat. No. 6,375,638 issued Apr. 23, 2002, and entitled "Incremental Motion Pump Mechanisms Driven by Shape Memory Alloy Wire or the Like," and U.S. patent application Ser. No. 11/230,142 filed Sep. 19, 2005, and entitled "SMA Wire Driven Positive Displacement Micro-Pump With Pulsatile Output," both of which are incorporated herein by reference in their entirety.

Escapement wheel arrangements operable with bender or linear actuators in accordance with example embodiments of the present invention are described with reference to FIGS. 16a-16c. As shown in FIG. 16a, an escapement wheel 60 is supported for rotation around an axis $A_1$ (extending into the page), in the direction of arrow 62. The escapement wheel 60 has an outer peripheral edge provided with serrations or teeth 64. Each tooth 64 includes a sloped surface 66 arranged at an obtuse angle relative to an axial direction of the wheel 60 and a catch surface 65 in a substantially axial direction of the wheel. A drive pawl 68 is located adjacent to the escapement wheel 60 and at least partially between two of the teeth on the escapement wheel. The drive pawl 68 is supported for movement in a generally linear direction, as represented by the double arrow 69, between a start position S and an end position E.

The drive pawl 68 has a drive surface 70 for engaging the catch surface 65 of an adjacent tooth 64 on the escapement wheel 60, when the drive pawl 68 is moved in a direction from the start position S to the end position E. The drive pawl 68 has a further surface 71 facing away from the drive surface 70 and configured for riding over the sloping surface 66 of a tooth 64 on the escapement wheel 60, when the drive pawl is moved in a return direction from the end position E to the start position S. The further surface 71 of the drive pawl 68 may be sloped at an angle relative to the radial direction of drive wheel, to assist the drive pawl 68 in riding over the sloping surface 66 of a tooth 64 of the escapement wheel.

As described in more detail below, the drive pawl 68 is coupled to a bender or linear motion actuator to selectively drive the drive pawl 68 from the start position S to the end position E. With each motion of the drive pawl 68 from the start position S to the end position E, the surface 70 engages the catch surface 65 of a tooth 64 on the escapement wheel and rotates the escapement wheel 60 a small distance. A bias member 72 is operably coupled to the drive pawl 68, to bias the drive pawl 68 in a return direction, to return the drive pawl 68 to the start position. The bias member 72 may include a spring as shown in FIG. 14a or other suitable mechanism for providing a bias force to return the drive pawl 68 to the start position, including, but not limited to a permanent magnet, electro-magnet, electronic or thermal linear actuator, shape memory alloy actuator, or the like. In the illustrated embodiment, the bias member 72 is a coil spring having one end coupled to the drive pawl 68 and another end coupled to a fixed surface, for example, a fixed surface of a wall or other fixed structure of or within the durable portion 22 of the drive mechanism 12 described above.

A further pawl 74 may be provided to inhibit back rotation of the escapement wheel 60 in the direction opposite to the direction of arrow 62. For example, the further pawl 74 may be located adjacent the escapement wheel 60 and at least partially between two of the teeth on the escapement wheel. The further pawl 74 has a surface 76 for engaging the catch surface 65 of an adjacent tooth 64 on the escapement wheel 60, to inhibit rotary motion of the escapement wheel 60 in the direction opposite to the direction of arrow 62.

The pawl 74 has a further surface 77 facing opposite to the surface 76, configured for riding over the sloping surface 66 of a tooth 64 on the escapement wheel 60, when the escapement wheel is driven in the rotary direction of arrow 62 by action of the drive pawl 68. The surface 77 of the pawl 74 may be angled relative to the radial direction of the drive wheel, to assist the pawl 74 in riding over the sloping surface 66 of a tooth 64 of the escapement wheel. The pawl 74 may be supported for pivotal motion about a pivot point 78 in the direction of double arrow 79, to allow the surface 77 of the pawl 74 to pivot in a direction away from the escapement wheel, to further assist the pawl 74 in riding over the sloping surface 66 of a tooth 64 of the escapement wheel.

A bias member 80 may be arranged to bias the surface 76 of the pawl 74 toward the escapement wheel, to return the pawl 74 to a position in which the surface 76 engages the catch surface 65 of a tooth 64, after the pawl 74 has ridden over the sloping surface 66 of an adjacent tooth 64 of the escapement wheel. The bias member 80 may include a spring as shown in FIG. 16a or other suitable mechanism for providing a bias force to return the pawl 74 to the position in which the pawl surface 76 engages the catch surface 65 of a tooth 64, including, but not limited to a permanent magnet, electro-magnet, electronic or thermal linear actuator, shape memory alloy actuator, or the like. In the illustrated embodiment, the bias member 80 includes a coil spring having one end coupled to the pawl 74 and another end coupled to a fixed surface, for example, a fixed surface of a wall or other fixed structure of or within the durable portion 22 of the drive mechanism 12 described above. In further embodiments, a leaf spring or other suitable spring structure may be employed, instead of a coil spring. For example, a spring may be located around or within the pivot point 78 of the pawl 74 for effecting the bias force described above.

As described above, the drive pawl 68 is coupled to a bender or linear motion actuator to selectively drive the drive pawl 68 and cause the escapement wheel to rotate a small distance with each motion of the drive pawl 68 from the start position S to the end position E. A bender or linear actuator may include a piezoelectric bender or piezoelectric actuator, a thermally actuated bender, a shape memory alloy wire, an electronically actuated solenoid, or the like. Such actuators for providing small, generally linear movements in response to the application of an electrical power signal are known. Examples of alternative shape memory alloy wire drive systems may be found in U.S. Pat. No. 6,375,638 issued Apr. 23, 2002, and entitled "Incremental Motion Pump Mechanisms Driven by Shape Memory Alloy Wire or the Like," and U.S. patent application Ser. No. 11/230,142 filed Sep. 19, 2005, and entitled "SMA Wire Driven Positive Displacement MicroPump With Pulsatile Output," both of which are incorporated herein by reference in their entirety.

As shown in FIG. 16b, a bender actuator 82 may be configured to include a connector end 84 that is provided with a lateral motion represented by arrow 86 relative to a major axis $A_2$ of the actuator body, when a power signal is applied to the actuator. Alternatively, as shown in FIG. 14c, a linear actuator 88 may be configured to include a connector end 90 that is provided with a longitudinal motion represented by arrow 92 relative to a major axis $A_3$ of the actuator body, when a power signal is applied to the actuator. A bender actuator as shown in FIG. 16b, for providing lateral motion, may be coupled to the drive pawl 68 at a connection location 96. The connection location 96 for a bender actuator may be on a surface of the drive pawl 68 that is substantially perpendicular to the drive surface 70. Alternatively, a linear actuator as shown in FIG. 16c, for providing longitudinal motion, may be coupled to the drive pawl 68 at a connection location 98. The connection location 98 for a linear actuator may be on a surface of the drive pawl 68 that is substantially parallel to the drive surface 70. In that manner, a bender or a linear actuator as shown in FIGS. 16b and 16c may be employed to selectively move the drive pawl 68 from the start position S to the end position E and, thus drive the escapement wheel 60 in a rotary manner. In yet further embodiments, the drive pawl 68 may be eliminated and the bender or linear actuator may be arranged to directly engage the catch surfaces of the teeth on the escapement wheel 60.

The escapement wheel 60 may be configured to rotate the rotary distance of one tooth for each movement of the drive pawl 68 from the start position S to the end position E. In further embodiments, the drive pawl 68 may be configured to cause the escapement wheel 60 to rotate a rotary distance of a pre-defined number of teeth greater than one tooth, for each movement of the drive pawl 68 from the start position S to the end position E. The escapement wheel 60 may be coupled to the lead shaft 42, to rotate the lead shaft 42 with rotation of the escapement wheel 60. In one embodiment, the lead shaft 42 may be connected in axial alignment directly to the escapement wheel 60, such that the rotary axis $A_1$ of the escapement wheel is in alignment with the longitudinal axis of the lead shaft 42. In other embodiments, the escapement wheel 60 may be coupled, in axial alignment, with any one of the drive gear 46, engagement gear 47 or linking gear 48 shown in FIG. 4 or FIG. 8, to transfer rotary motion of the escapement wheel 60 to the lead shaft 42. In yet further embodiments, other suitable gear and linkage arrangements may be employed for transferring rotary motion of the escapement wheel 60 to the lead shaft 42.

The use of bender or linear actuators with escapement wheel arrangements as described above may provide certain advantages over electric motor and linkage arrangements, in that the bender or linear actuators can provide a repeatable, controlled, step-like response to an electrical power signal. In the context of driving a delivery device for delivering a medication to a patient-user, the ability to accurately control the drive response can provide significant advantages, for example, in administering accurate quantities, small quantities at accurate levels and accurate recording of delivered quantities of the medication. In addition, bender or linear actuators with escapement wheel arrangements can be made relatively small and flat and can, therefore, improve the ability to form the delivery device 12 with a relatively small and flat shape. In addition, bender or linear actuators with escapement wheel arrangements can operate with relatively low power requirements, thus prolonging the operational life of the power source and allowing smaller power sources to be employed, thus, allowing further reductions in the size of the delivery device.

Other types of drive devices may be coupled to an escapement wheel 60, as shown in FIG. 16d, to provide a controlled, step-like response. For example, in the embodiment shown in FIG. 16d, a second wheel 99 has one tooth and is coupled to the lead shaft 42 as described above, while the toothed escapement wheel 60 is operatively coupled to the lead shaft 42, for example, through a suitable linkage structure as described herein. The second wheel 99 may be driven by any suitable rotary drive source, including, but not limited to a DC motor, flat or pancake DC motor, servo motor, stepper motor, electronically commutated motor, rotary piezo-electrically actuated motor, and the like. While the second wheel 99 in FIG. 16d is provided with a single tooth to effect a rotation of the escapement wheel 60 a rotary distance of a single tooth for each complete rotation of the second wheel 99, other embodiments may employ a second wheel 99 having two teeth (or another pre-defined number of teeth) for effecting a rotation of the escapement wheel 60 a rotary distance of two teeth (or the pre-defined number of teeth) for each complete rotation of the second wheel 99.

The above embodiments involve various manners of conveying a drive force to the lead shaft 42, to rotate the lead shaft 42 and drive a piston plunger 32 within the reservoir 26. Further embodiments may employ other mechanisms for driving a plunger within a reservoir, to selectively deliver infusion medium from the reservoir.

For example, FIGS. 17-21 show a further embodiment of a delivery device, which includes a disposable portion 120 and a durable portion 122. The disposable portion has a reservoir retaining portion 124 in which a reservoir 126 is located. The disposable portion 120, durable portion 122, reservoir retaining portion 124 and reservoir 126 may be similar to the disposable portion 20, durable portion 22, reservoir retaining portion 24 and reservoir 26 described above with respect to FIGS. 2-6. However, the reservoir 126 in FIGS. 17-21 employs a rotatable plunger shaft 127 located within the reservoir interior 128, instead of the arrangement shown in FIGS. 2-8 that employs a piston plunger shaft 40 that extends, lengthwise, a distance beyond the medium-containing portion of the interior 28 of the reservoir 26 by a distance at least as great as the distance that the piston head 34 moves over the full period of use of the reservoir. Accordingly, the overall length of the reservoir and internal shaft of FIGS. 17-21 may be smaller relative to the overall length of the reservoir and external shaft of FIGS. 2-8, for a given reservoir volume.

Figure 18:
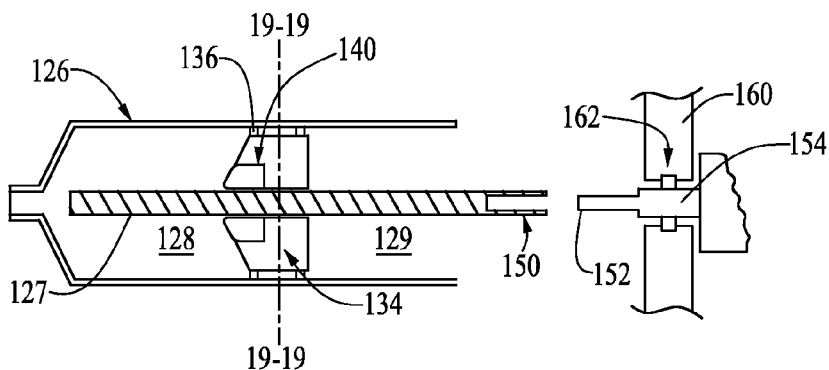
FIG. 18 shows a schematic, cross-sectional view of a reservoir and moveable plunger head of the delivery device of FIG. 17.
Figure 17:
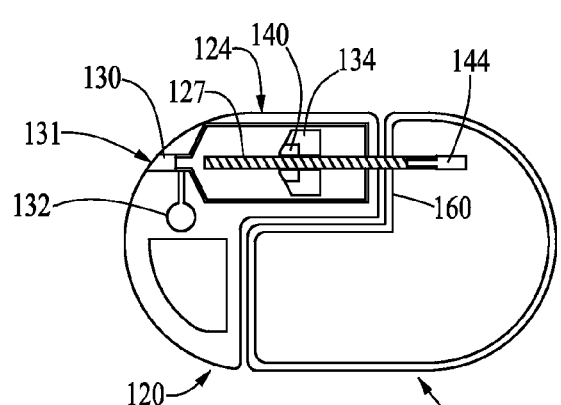
FIG. 17 shows a schematic view of a delivery device according to a further embodiment of the present invention.

The reservoir 126 in FIGS. 17 and 18 may include a septum 130, similar to the septum 30 described above with respect to FIG. 5. The septum 130 may include a surface 131 that is exposed through a wall of the reservoir retaining portion 124, for filling the reservoir 126 or withdrawing infusion medium from the reservoir 126, for example, by piercing the exposed surface of the septum with a syringe.

An injection site 132 may be located within the disposable portion 120, adjacent the reservoir 126 and connected in fluid flow communication to the interior of the reservoir 126. The injection site 132 may employ a mechanism for inserting a hollow needle or cannula into a patient-user, after the disposable portion 120 is secured to the patient-user and coupling the needle or cannula in fluid flow communication to the interior of the reservoir 126. Examples of mechanisms that may be used for inserting a hollow needle or cannula into a patient-user and coupling the needle and cannula in fluid flow communication with a reservoir are described in U.S. patent application Ser. No. 11/211,095, filed Aug. 23, 2005, and U.S. Patent Application No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006. Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

The rotatable shaft 127 is threaded along its length within the interior of the reservoir 126. A moveable plunger head 134 is located within the interior of the reservoir 126 and is threaded and engaged with the rotatable shaft 127. In particular, the plunger head 134 has a threaded channel that has threads of a pitch and diameter to engage and mate with the threads of the rotatable shaft 127. By rotating the shaft 127 without rotating the plunger head 134, the plunger head is moved along the length of the shaft 127, within the interior of the reservoir 126. In this manner, the shaft 127 may be rotated to drive the plunger head 134 and force the infusion medium from the reservoir 126 to a patient-user, through a hollow needle or cannula connected in fluid flow communication with the reservoir. While the threaded channel in the plunger head 134 may be located at the center of the diameter of the plunger head 134, other embodiments may employ a plunger head 134 with an off-center channel (a channel that is laterally spaced relative to the longitudinal axis A of the reservoir). An off-center location of the channel in the plunger head 134 allows the transfer of linear motion (with the rotational motion of the lead shaft 127) to the plunger head 134, while inhibiting rotation of the plunger head 134 relative to the lead shaft 127.

One or more seals 136 may be provided around the outer peripheral surface of the plunger head 134, to inhibit the passage of infusion medium across the plunger head 134, from the medium-retaining interior portion 128 of the reservoir to the external side 129 of the plunger head 134. One or more annular grooves may be provided in the outer peripheral surface of the plunger head 134 for retaining the seal(s) 136. The seal(s) 136 may include one or more o-ring seals or other suitable seal structure and may be made of any suitable seal material, including, but not limited to, rubber, silicone rubber, polyurethane or other plastic material, metal, composite material or the like. The seal(s) 136 may provide sufficient frictional force between the plunger head 134 and the interior surface of the reservoir 126 to inhibit rotation of the plunger head 134 with the rotation of the shaft 127. However, in further embodiments, additional structure may be provided to inhibit rotation of the plunger head with the rotation of the shaft 127, including, but not limited to, one or more projections or shaped portions 138 on the plunger head 134 that fit within corresponding one or more shaped grooves along the length of the interior wall of the reservoir 126, as shown in the cross-section view of FIG. 19 (taken along the cross-section 19-19 of FIG. 18). The shaped projection(s) 138 may have generally curved configurations, with slow curvatures (as compared to an abrupt step), to allow one or more seals 136 to be placed around the plunger head. In alternative embodiments, the interior wall of the reservoir 126 may include a projecting portion extending along the length of the reservoir, for engaging a corresponding groove in the plunger head 134, similar to, but reverse of the projection and groove arrangement shown in FIG. 19. In yet further alternative embodiments, the cross-sectional shape of the plunger head 134 and the reservoir 126 (in the cross-sectional direction shown in FIG. 19) may be non-circular, to inhibit rotation of the plunger head 134 with rotation of the shaft 127. Such non-circular cross-section shapes may include, but are not limited to, an oval or partially oval shape, a polygonal or partially polygonal shape, or the like.

Figure 20:
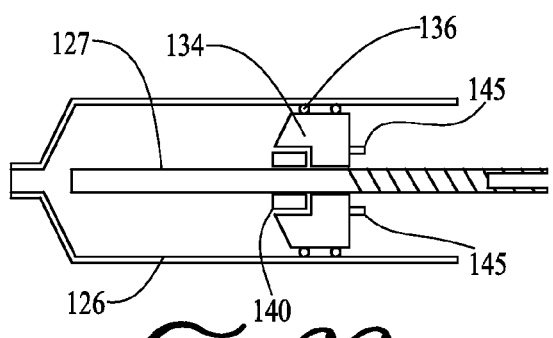

The plunger head 134 includes one or more seals 140 arranged to provide a fluid-tight seal between the plunger head 134 and the lead shaft 127, to inhibit the passage of infusion medium through the central channel of the plunger head 134, from the infusion medium-retaining interior portion 128 of the reservoir to the external side 129 of the plunger head 134, as the plunger head 134 is moved toward the septum end of the reservoir 126. The seal(s) 140 may include an annular structure disposed on one side (such as the infusion-medium-contacting side) of the plunger head 134 and made of any suitable seal material, including, but not limited to, rubber, silicone rubber, polyurethane or other plastic material, metal, composite material or the like. Alternatively, or in addition, the seal(s) 140 may be located within the central channel of the plunger head 134, between the plunger head 134 and the lead shaft 127. In the embodiment of FIG. 20, the lead shaft 127 is, at least initially, not threaded, while the plunger head 134 is provided with one or more cutting blades 145, to cut threads into the lead shaft 127 and ride along the cut threads, as the lead shaft is rotated. In the embodiment of FIG. 20, the lead shaft 127 may be made with a smooth surface and of any suitable material that would allow the thread forming blade(s) 145 to cut threads into the lead shaft 127 when the lead shaft 127 is rotated by the drive linkage 154. Rotation of the lead shaft 127 would cause the thread forming blades to cut threads into the lead shaft 127 and would cause the plunger 134 to move toward the infusion medium-retaining interior portion 128 of the reservoir 126.

Figure 21:
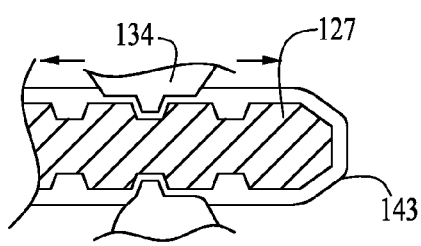
FIGS. 20 and 21 show schematic views of embodiments of seal arrangements for the plunger head within the reservoir of FIGS. 17 and 18.

Alternatively, or in addition, the lead shaft 127 may be coated or wrapped with one or more layers 143 of a seal material, as shown in FIG. 21. The seal material layer 143 may include, but is not limited to rubber, silicone rubber, polyurethane or other plastic material, or other material having suitable elasticity and flexibility to allow the threads of the plunger head 134 to operatively engage the coated or wrapped threads of the lead shaft 127. In yet further embodiments, the inner surface of the central channel in the plunger head may be provided with seals 140 or sealing material 143, in addition to or as an alternative to seals or sealing material on the shaft 127.

The shaft 127 has a connection end 150, for connection to a mating connection end 152 of a drive linkage 154. The drive linkage 154 may be a direct connection to the drive shaft of a motor 144, such that the connection end 152 of the drive linkage 154 rotates with the rotary drive motion of the drive shaft of the motor 144. In other embodiments, the drive linkage 154 may include one or more gears, belts, chains, drive shafts or other linkage structure (not shown) for transferring drive force from a motor 144 to rotational motion of the connection end 152 of the drive linkage. The motor 144 may be any suitable drive device for rotatably driving the connection end 152 of the drive linkage (either directly or through one or more gears, belts, chains, drive shafts or other linkage structure), including, but not limited to the example drive devices described above with respect to the motor 44 in FIG. 4 and escapement wheel arrangements in FIGS. 16*a*-16*d*.

The motor 144 and any gears, belts, chains, drive shafts or other linkage structure for coupling the motor 144 to the drive linkage 154 may be contained within the interior of the housing structure of the durable portion 122. The drive linkage or the drive shaft of the motor 144 may extend through an aperture in a wall 160 of the housing structure of the durable portion 122. A seal 162 may be provided within or adjacent the aperture in the wall 160, to inhibit the passage of one or more of moisture, air, biological materials or infusion media into the interior of the housing structure of the durable portion 122. The seal 162 may include, but is not limited to, one or more o-ring seals disposed around the aperture in the wall 160 or around the portion of the drive linkage or drive shaft that extends through the aperture in the wall 160. The seal 162 may be made of any suitable sealing material, including, but not limited to rubber, silicone rubber, polyurethane or other plastic material, metal, composite material or the like.

The connection end 152 of the drive linkage 154 and the connection end 150 of the lead shaft 127 are configured to connect to each other when the durable portion 122 is coupled to the disposable portion 120 and to disconnect from each other when the durable portion 122 is separated from the disposable portion 120. For example, the connection ends 150 and 152 of the lead shaft 127 and the drive linkage 154, respectively, may include mating features that are configured to easily engage with each other when the connection ends 150 and 152 are brought together and disengage from each other when the connection ends 150 and 152 are moved apart. In addition, the mating features allow the transfer of rotational motion from the drive linkage 154 to the lead shaft 127, when the connection ends 150 and 152 are engaged.

In one example embodiment as shown in FIG. 22, the mating features may include a slot 164 formed on the connection end 150 of the lead shaft 127 and a tab 166 extending from the connection end 152 of the drive linkage 154, where the tab 166 is shaped to fit within the slot 164 to connect the lead shaft 127 in rotational communication with the drive linkage 154. Alternatively, the slot 164 may be formed on the connection end 152 of the drive linkage 154 and the tab 166 may extend from the connection end 150 of the lead shaft 127. The shape of the tab 166 and the slot 164 in FIG. 20 have a generally rectangular cross-sectional dimension (in the cross-section plane perpendicular to the longitudinal dimension of the lead shaft 127). Other embodiments may employ a tab and slot arrangement with other non-circular cross-sectional shapes (in the cross-section plane perpendicular to the longitudinal dimension of the lead shaft 127) to allow communication of rotational motion from the drive linkage 154 to the lead shaft 127. In further alternative embodiments, the mating features may be other shapes that can be readily engaged together to communicate rotational motion from the drive linkage to the lead shaft 127 and readily separated to allow the durable portion 122 to be removed from the disposable portion 120 of the delivery device. Such other shapes include, but are not limited to, mating star-shaped structures, cross-shaped structures, non-circular mating shapes (e.g., oval, partially oval, polygonal or partially polygonal), a mating pattern of projections and recesses, or the like, on the connection ends 150 and 152.

In the delivery device embodiments described above, a plunger head 34 or 134 is driven within a reservoir 26 or 126 to drive the infusion medium from the reservoir. Further embodiments of mechanisms for driving a plunger head within a reservoir of a delivery device are described with reference to FIGS. 23-27.

In the embodiment of FIG. 23, a reservoir 226 employs a moveable plunger head 234. The reservoir 226 and the plunger head 234 may be similar to the reservoir 126 and plunger head 134 described above with respect to FIG. 18, except that the plunger head 234 need not include a threaded central channel. The plunger head 234 includes seals 236 similar to the seals 136 on the plunger head 134 described above with respect to FIG. 18. The plunger head 234 and reservoir 226 may include further structure to inhibit rotation of the plunger head within the reservoir 226, for example, as described above with respect to example structure for inhibiting rotation of the plunger head 134, including, but not limited to, structure described above with respect to FIG. 19. The reservoir 226 may include a septum 230, similar to the septa 30 and 130 described above. The septum 230 may be used for refilling the reservoir 226 and/or for receiving a hollow needle or cannula to provide a fluid flow path to a patient-user, as described above with respect to the septa 30 and 130.

A slide tube 240 is configured to engage the plunger head 234. The slide tube 240 includes a generally hollow, cylindrical tube made of a suitably rigid material, such as, but not limited to, metal, plastic, ceramic, composite material or the like. One end of the cylindrical slide tube 240 is provided with a mating feature 242 for mating with a corresponding mating feature 244 on the plunger head 234. In the embodiment of FIG. 23, the mating feature 242 includes a projection that extends from the end of the slide tube 240 in the axial direction of the cylindrical shape of the slide tube, while the mating feature 244 includes a recess in the exterior-facing side of the plunger head 234. The recess 244 has a shape adapted to receive the projection 242, when the end of the slide tube 240 is brought into engagement with the exterior-facing side of the plunger head 234. The recess 244 and projection 242 may have corresponding, mating shapes having non-circular cross-sectional dimensions (in the cross-section plane perpendicular to the axis $A_5$) that inhibit relative rotation between the slide tube 240 and the plunger head 234. In another embodiment (as shown in FIG. 24), the plunger head 234 may be connected to (or unitary with) a sleeve 240 that has a hollow interior. The sleeve 240 in FIG. 24 may have a slot-like opening along its longitudinal dimension through which a rotary drive screw 248 may be received. The slot-like opening in the sleeve 240 may be smaller than the diameter of the rotary drive screw 248 and the sleeve 240 may be made of a suitably elastically flexible material to allow the dive screw 248 to be snap fit into the hollow interior of the sleeve 240, through the slot-like opening in the sleeve 240.

The slide tube 240 (in either of the embodiments of FIGS. 23 and 24) has a generally hollow interior and an interior surface 246 that is threaded along at least a portion of its length. The rotary drive screw 248 includes a shaft that extends coaxially with the slide tube 240. The drive screw 248 shaft extends through one end (opposite to the end connected to the plunger head) of the slide tube 240. One end of the drive screw 248 shaft extends into the interior of the slide tube 240 and an opposite end of the drive screw 248 shaft extends outside of the slide tube 240. The drive screw 248 may be threaded along its length (as shown in FIG. 24) or may have a threaded head 249 coupled to the drive screw shaft (as shown in FIG. 23). The threads along the length of the drive screw 248 or the threaded head 249 has threads of a pitch and diameter for engaging and mating with the threads on the threaded interior surface 246 of the slide tube 240. In that arrangement, rotation of the drive screw 248 results in a linear movement of the slide tube 240 along the direction of the axis $A_5$ of the slide tube 240. By rotating the drive screw with a rotary drive device in the appropriate direction, the slide tube pushes the plunger head 234 toward the septum end of the reservoir 226, to force infusion medium through a hollow needle or cannula, to a patient-user.

The end of the drive screw 248 shaft that is external to the slide tube 240 is coupled to a drive device, through suitable drive linkage, to rotate the drive screw 248 in a controlled manner. In the embodiment shown in FIG. 23, the drive device includes a linear actuator 250, such as a piezoelectric actuator device that expands in a linear direction, upon the application of a suitable electrical drive signal. The actuator 250 is arranged to frictionally engage and rotate a rotary wheel 252 a small amount in the direction of arrow 256 with each linear expansion of the actuator 250. The actuator 250 may be selectively controlled to drive the rotary wheel 252 in the direction of arrow 256 for dispensing infusion medium from the reservoir 226, and in the direction opposite to the direction of arrow 256, to retract the plunger head 234 and allow replacement of the reservoir 226. A spring 254 or other suitable structure may be provided to force the actuator 250 against the rotary wheel 252 during expansion of the actuator. The rotational motion of the rotary wheel 252 is transferred to rotational motion of the drive screw 248, through suitable transfer gearing 258. According to the arrangement shown in FIG. 21, the linear actuator 250 may be selectively energized to rotate the wheel 252, which rotates the drive screw 248, which causes the slide tube 240 to move axially and push the plunger head 234 toward the septum end of the reservoir 226, in a controlled, step-like manner.

While FIG. 23 shows a linear drive device that includes a linear actuator for rotatably driving the drive screw 248, other embodiments may employ other drive devices operatively coupled to drive the drive screw 248. For example, FIG. 24 shows an embodiment in which the drive device includes a DC pancake motor 260 that is operatively coupled to the external end of the drive screw 248, through any suitable interface gear arrangement 262. In further embodiments, the drive screw 248 may be operatively coupled to any suitable drive device for rotatably driving the drive screw 248 in a controlled manner, including, but not limited to the example drive devices described above with respect to the motor 44 in FIG. 4 and escapement wheel arrangements in FIGS. 16a-16d.

As shown in FIG. 23, the slide tube 240 may be supported within a portion of a housing structure 266, such as the housing structure of a durable portion of a delivery device. The slide tube 240 extends through an opening in the housing structure 266 to engage the plunger head 234. One or more seals 268 may be disposed around the opening in the housing structure 266 and/or the slide tube 240, to protect the drive device from, for example, moisture, air, biological material or infusion media. The seal(s) 268 may be o-ring seals or other suitable seals made of any suitable seal material, including, but not limited to, the seal materials described above with respect to the seal(s) 45. In addition, an anti-rotation structure may be provided, to inhibit rotation of the slide tube 240 about the axis $A_5$, relative to the housing structure 266. In one embodiment, the anti-rotation structure may include a projection 241 extending from the slide tube 240, for engaging a stop surface 243 that is fixed relative to the housing structure 266. In other embodiments, the seal(s) 268 may provide sufficient frictional engagement with the slide tube and/or the housing structure 266, to inhibit rotation of the slide tube 240 about the axis $A_5$, relative to the housing structure 266.

Figure 25:
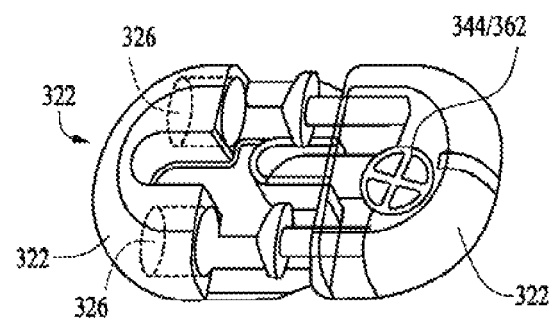
FIG. 25 shows a perspective view of a delivery device containing two reservoirs that may employ a drive device according to FIGS. 23, 24 or 26 or other suitable drive device.

The reservoir 226 may be located within a disposable housing portion, while the slide tube 240, drive screw 248 and drive device 250 or 260 may be located within a durable housing portion that can selectively couple to or separate from the disposable housing portion, as described above with respect to embodiments of FIGS. 1-22. In a further embodiment, as shown in FIG. 25, a delivery device includes a disposable housing portion 320 having a reservoir retaining portion 324 for containing multiple reservoirs 326 (two in FIG. 25). A piston plunger head 334 is located in each reservoir 326 and may be operated by a slide tube arrangement similar to that shown in either of FIG. 23 or 24 or other suitable piston moving structure. The delivery device in FIG. 25 includes a durable housing portion 322 for containing one or more drive devices 344 and linkage 362 (which may include, for example bevel gears pinion gears or other suitable gear arrangements) for coupling the drive device(s) to the reservoirs 326. For example, a drive device, slide tube and drive screw arrangement as described with respect to FIGS. 23 and 24 may be included in the durable housing portion 322.

Figure 26:
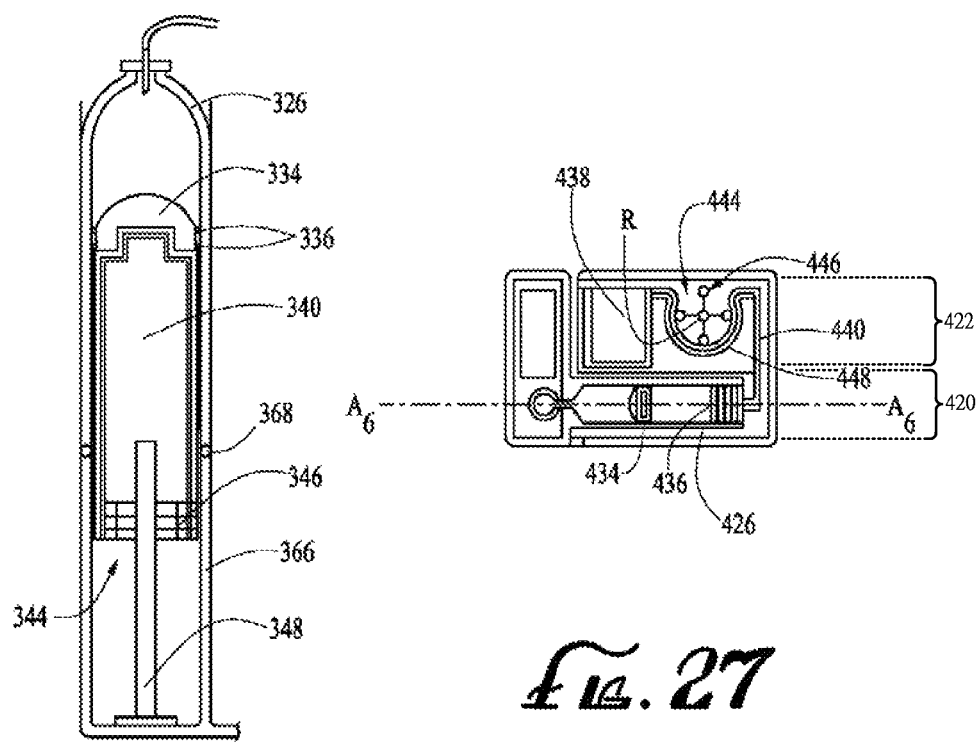
FIG. 26 shows a schematic cross-sectional view of a reservoir and drive device for a delivery device according to a further embodiment of the present invention.

The embodiment of FIG. 26 employs a reservoir 326, plunger head 334, seals 336 and seals 368, similar to the reservoir 226, plunger head 234, seals 236 and seals 268 described above with respect to FIG. 23. The embodiment of FIG. 26 also includes a slide tube 340, similar to the slide tub 240 of FIG. 23, except that the slide tube 340 need not include a threaded interior surface. Instead, the slide tube 340 in FIG. 26 is operatively coupled to a drive device 344 in the form of a linear motor comprising one or more (two in FIG. 26) piezoelectric stacks 346 compressed on a drive shaft 348. The drive shaft 348 may be fixed to a durable portion 366 of delivery device, similar to the durable portion 266 described above.

The linear motor drive device 344 may be selectively energized by selectively applying electrical control signals to the piezoelectric stacks to cause the slide tube 340 to move toward the septum end of the reservoir 326, to selectively force infusion medium out of the reservoir, as described above with respect to the reservoir 226 in FIG. 23. However, the linear motor drive device 344 of FIG. 26 may be considerably smaller and may consume less power than some of the drive devices and linkages described above for creating rotary motion to drive the slide tube 240 of FIG. 23.

Figure 27:
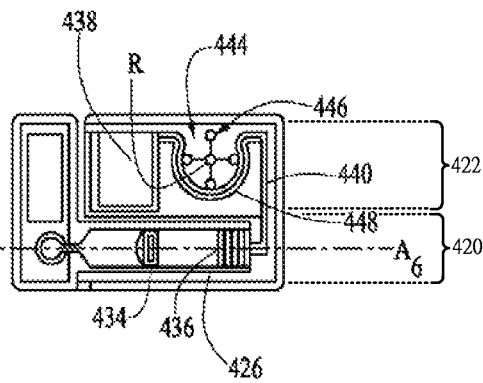
FIG. 27 shows a schematic view of a delivery device according to a further embodiment of the present invention.

A further embodiment of a delivery device shown in FIG. 27 includes a reservoir 426 and a moveable plunger head 434 within the interior of the reservoir 426. The reservoir 426 and plunger head 434 may be similar to the reservoir 326 and plunger head 334 of FIG. 26, except that the plunger head 434 need not have a mating feature for engaging a slide tube. Instead, the plunger head 434 is configured to abut an expandable bellows 436 and move along the direction of the longitudinal axis $A_6$ of the reservoir 426 with the expansion of the bellows 436.

The bellows 436 is any suitable expandable structure that includes an interior volume that is expandable and that is capable of containing a hydraulic fluid. The delivery device in FIG. 27 includes a second reservoir 438 for containing hydraulic fluid, a conduit or tube 440 connected to the hydraulic fluid reservoir 438 and the bellows 436, for providing a fluid-flow communication path between the hydraulic fluid reservoir 438 and the interior volume of the bellows 436. A pumping mechanism 444 is provided to selectively pump hydraulic fluid into the bellows 436.

In the embodiment shown in FIG. 27, the pumping mechanism 444 is a peristaltic pump device including a rotor 446 mounted for rotation about an axis R. The rotor 446 has a plurality of rollers or pads arranged to engage a portion of the conduit 440 and roll or slide along a length of the conduit 440. The conduit 440 may be elastically flexible, at least along the length engaged by the rotor 446 rollers or pads. The length of the conduit 440 engaged by the rotor 446 may be arranged along an arcuate surface 448, where the arc of the surface 448 corresponds to the diameter of the rotor 446. The arcuate surface 448 may be a surface of a wall or other structure formed within the durable housing portion 422.

By rolling across the conduit 440 on the arcuate surface 448, the rotor rollers or pads may engage and squeeze the conduit 440 during the period of motion of the rollers or pads along the length of the arcuate surface 448. The rolling or sliding motion of the rotor rollers or pads along the arcuate length of the flexible conduit 440 creates a sufficient pressure differential to drive hydraulic fluid from the hydraulic fluid reservoir 438 to the interior of the bellows 436, in a manner controlled by the controllable rotary motion of the rotor 444. Any suitable rotary drive device or arrangement, such as, but not limited to those described herein, may be employed to drive the rotor 444 in a controlled manner.

As hydraulic fluid is pumped into the bellows 436 by the pumping mechanism 442, the hydraulic fluid creates a fluid pressure within the bellows sufficient to cause the bellows to expand an amount dependent upon the amount of hydraulic fluid pumped into the bellows. As the bellows 436 expands, the end of the bellows that abuts the plunger head 434 is moved toward the septum end of the reservoir 426 and pushes the plunger head 434 toward the septum end of the reservoir 426. As the plunger head 434 is moved toward the septum end of the reservoir 426, the plunger head forces infusion medium within the reservoir 426 out through a suitable hollow needle or cannula, to a patient-user.

While the embodiment of FIG. 27 employs a peristaltic pump device 444 to drive hydraulic fluid from the hydraulic fluid reservoir 438 to the bellows 436 in a controlled manner, other embodiments may employ other suitable pump devices for performing that function, including, but not limited to, conventional piston pumps, impeller pumps, membrane pumps, or the like.

In the embodiment shown in FIG. 27 the reservoir 426 may be located in a disposable portion 420 of the delivery device, while the hydraulic fluid reservoir 438, hydraulic fluid pump device 444, pump drive motor (not shown) and bellows 436 may be located in a disposable portion 420 of the delivery device. The disposable portion 420 and durable portion 422 may be configured to be coupled together for operation, or separated for servicing, as described above with respect to disposable portion 20 and durable portion, 22 in FIGS. 2 and 3. The disposable portion 420 may be provided with a needle insertion mechanism, for inserting a hollow needle or cannula into a patient-user's skin and connecting the hollow needle or cannula in fluid flow communication with the interior of the reservoir 426, when the disposable portion 420 is secured to a patient-user's skin, as described above with respect to the disposable portion 20 of FIGS. 2 and 3. Examples of mechanisms that may be used for inserting a hollow needle or cannula into a patient-user and coupling the needle and cannula in fluid flow communication with a reservoir are described in U.S. patent application Ser. No. 11/211,095, filed Aug. 23, 2005, and U.S. Patent Application No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006. Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Figure 28:
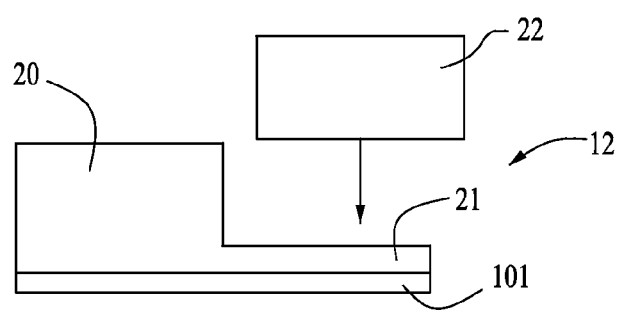
FIG. 28 shows a schematic side view of an arrangement of a durable housing portion and a disposable housing portion of a delivery system according to an embodiment of the invention consistent with the embodiment of FIG. 3.

In embodiments described above, the disposable housing portion (e.g., 20 in FIG. 3) is provided with a base portion 21 that may be secured to the patient-user's skin by, for example, but not limited to, an adhesive material provided on the bottom surface of the base portion 21. That arrangement is generally represented, in side view, in FIG. 126, wherein an adhesive material 101 is provided on the bottom surface (skin-facing surface) of the base 21 of the disposable housing portion 20. As shown in FIGS. 2, 3 and 28, the durable housing portion 22 may be configured to be arranged on the base 21 of the disposable housing portion 20 to engage and connect to the disposable housing portion 22. In such an arrangement, the base 21 may be disposed between the durable housing portion 22 and the patient-user's skin, during operation, such that only the base 21 of the disposable housing portion remains in contact with the patient-user's skin, during operation.

Figure 29:
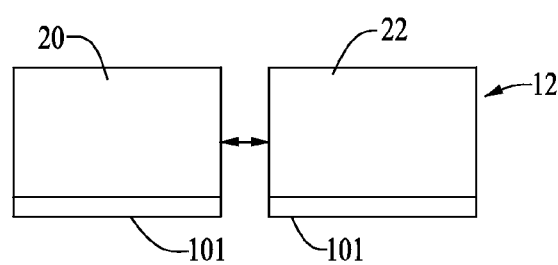
FIG. 29 shows a schematic side view of an arrangement of a durable housing portion and a disposable housing portion of a delivery system according to another embodiment of the invention.

However, in other embodiments, the durable housing portion 22 and the disposable housing portion 20 may be configured to engage each other in a side-by-side arrangement, for example, as represented in FIG. 29. In the side-by-side arrangement in FIG. 29, either one or both of the durable housing portion 22 and the disposable housing portion 20 may be provided with a base having an adhesive material 101 (and a peelable cover layer 23 as shown in FIG. 3).

Figure 30:
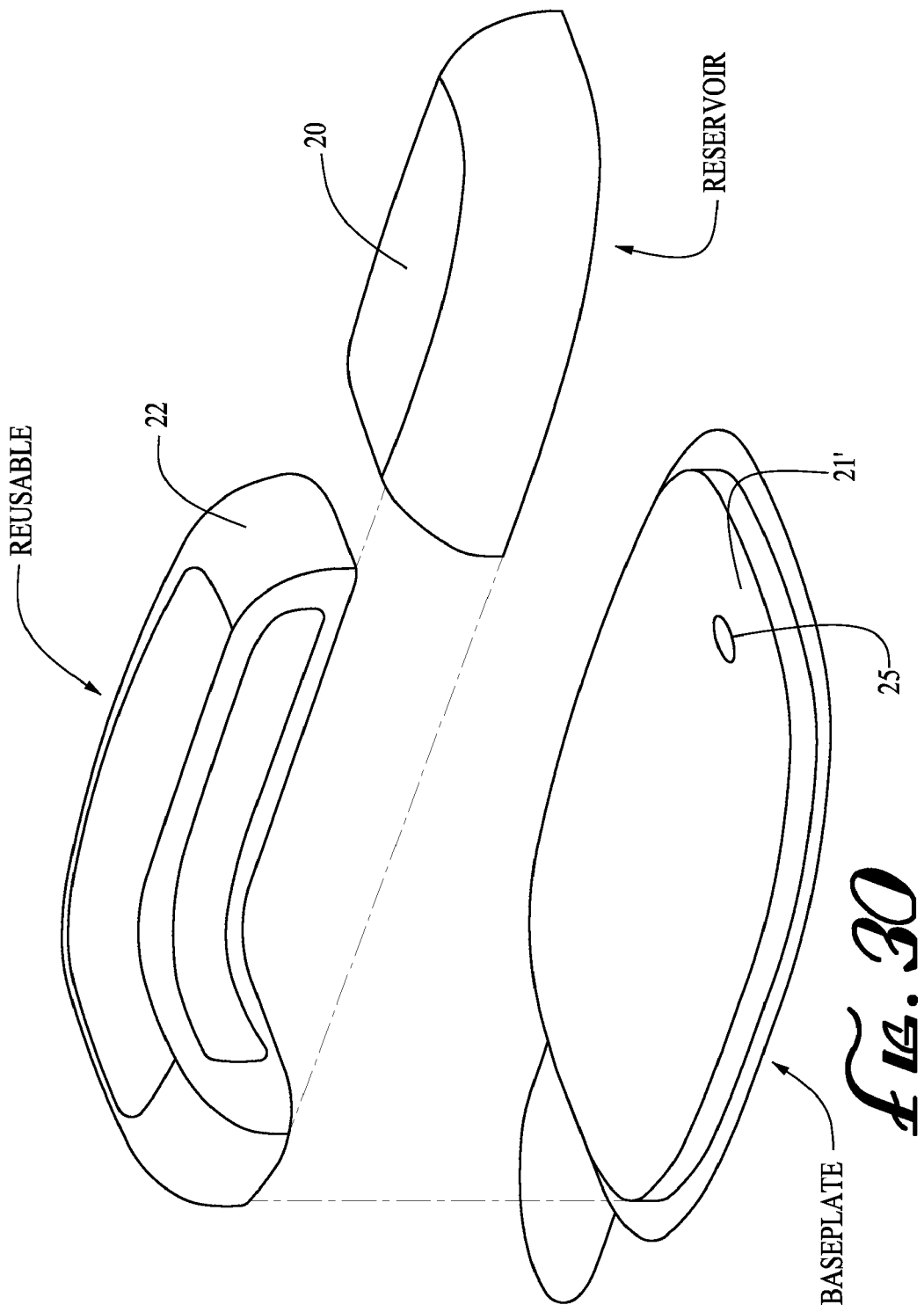
FIG. 30 shows a partially exploded view of a delivery device according to an embodiment of the invention.

In yet further embodiments, as represented by FIG. 30, one or both of the durable housing portion 22 and the disposable housing portion 20 may be attachable and detachable from a separate base member 21'. Suitable connecting structure, such as described above for connecting the durable housing portion and the disposable housing portion together, may be employed for connecting the durable housing portion and the disposable housing portion to the base member 21'. The separate base member 21' may include a generally flat, plate-like structure made of any suitably rigid material including, but not limited to, plastic, metal, ceramic, composite material or the like. The base member 21' has a surface (the upper-facing surface in FIG. 30) to which the disposable housing portion 20 and the durable housing portion 22 may be attached. The base member 21' has a second surface (the lower-facing surface in FIG. 30) to which an adhesive material and a peelable cover film may be applied, as described above, to allow the base member 21' to be secured to a patient-user's skin.

The base member 21' may include a needle inserter device 25, as described above. Examples of suitable needle inserter devices are described in U.S. patent application Ser. No. 11/211,095, filed Aug. 23, 2005, and U.S. Patent Application No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006, each of which is incorporated herein by reference in its entirety. In such embodiments, the base member 21' may be secured to a patient-user's skin. Then, the needle inserter 25 may be activated to insert a hollow needle or cannula into the patient-user's skin. Then, after the hollow needle or cannula is inserted, the durable housing portion 22 and the disposable housing portion 20 may be attached to the base member 21', to connect the reservoir within the disposable housing portion 20 in fluid flow communication with the hollow needle or cannula. In one embodiment, the durable housing portion 22 and the disposable housing portion 20 may be connected together (for example, in the manner described above) before attaching those housing portions to the base member 21'. In a further embodiment, one of the durable and disposable housing portion is attached to the base member 21' before the durable and disposable housing portions are connected together. In such further embodiment, the needle inserter device may be activated to insert a hollow needle or cannula into the patient-user's skin after the disposable housing portion is attached to the base member 21' (either before or after the durable and disposable housing portions are connected together).

Alternatively, reference number 25 may represent an opening in the base member 21' that aligns with a needle inserter device (or aligns with a further opening) located in the disposable housing portion 20, when the disposable housing portion 20 is attached to the base member 21'. In such embodiments, the base member 21' may be secured to the patient-user's skin. Then the disposable housing portion 20 is attached to the base member 21' (either before or after the durable and disposable housing portions are connected together). Once the disposable housing portion 20 is attached to the base member 21', the needle inserter device 25 may be activated to insert a hollow needle or cannula into a patient-user's skin (either before or after the durable and disposable housing portions are connected together). Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Figure 31:
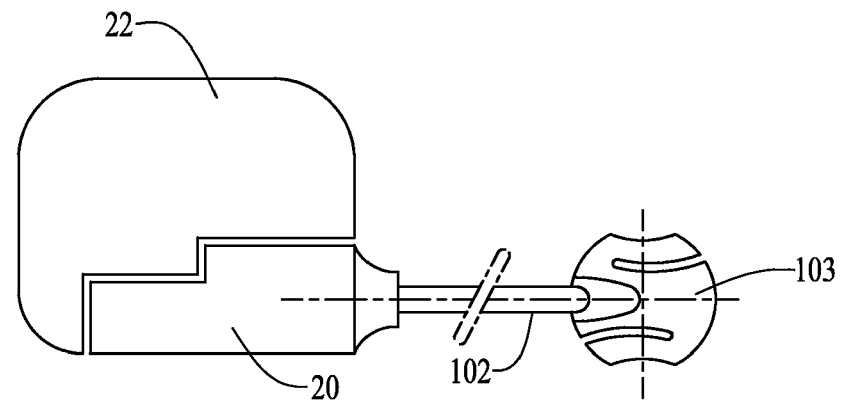
FIG. 31 shows a schematic top view of an arrangement of a durable housing portion and a disposable housing portion of a delivery system according to an embodiment of the invention.

Also, while embodiments described above may include an on-board needle or cannula injector device that may be activated through the operator or opening 25, other embodiments may employ an injection site module 103 that is external to the disposable housing portion 20, but connected to the disposable housing portion 20, through a suitable conduit 102, as shown in FIG. 31. The external injection site module 103 may include a needle or cannula injector device structure and an operator or opening (similar to the operator or opening 25 described above) through which the injector device may be activated. Alternatively or in addition, the external injection site module 103 may include an infusion set such as, but not limited to an infusion set as described or referenced in U.S. patent application Ser. No. 10/705,686, filed Nov. 10, 2003, titled "Subcutaneous Infusion Set" (Publication No. 2005/0101910) and/or U.S. patent application Ser. No. 11/004,594, filed Dec. 3, 2004, titled "Multi-Position Infusion Set Device And Process" (Publication No. 2006/0129090), each of which is assigned to the assignee of the present invention and each of which is incorporated herein by reference, in its entirety.

The conduit 102 that connects the module 103 with the disposable housing portion 20 may be any suitable tubing structure having a fluid flow passage, such as, but not limited to, a flexible tube made of plastic, silicone or the like. An adhesive material may be provided on the tubing structure (or between the tubing structure and the patient-user's skin) to secure the tubing to the patient-user's skin. By locating the injection site module 103 external to the disposable housing portion 20, the disposable housing portion 20 and the durable housing portion 22 may be clipped to a patient-user's clothing, belt, suspender or other article of apparel or may be held in a pocket of an article of apparel or carried in a purse or the like.

In one embodiment, the conduit 102 may be fixed at one end to the disposable housing portion 20, in fluid-flow communication with the reservoir within the disposable housing portion 20, and fixed at a second end to an external injection site module 103, for connection in fluid-flow communication with a hollow needle or cannula, as described above. In further embodiments, one or both of the ends of the conduit 102 may include suitable connection structures that allow the conduit ends to be selectively connected in fluid-flow communication with, and selectively disconnected from the disposable housing portion 20 and/or the injection site module 103. Such connectors may comprise a hollow needle and septum, a Luer connector, or other suitable fluid-communication connectors. In such embodiments, the disposable housing portion 20 and the durable housing portion 22 may be disconnected from the module 103, for example, by disconnecting one of the ends of the conduit 102 from the module 103 or the disposable housing portion 20, while leaving the module 103 in place (without requiring the patient-user to withdraw the needle or cannula and, later, insert a needle or cannula to resume operation). In this manner, a patient-user may readily disconnect and remove the disposable housing portion 20 and durable housing portion 22, for example, to allow the patient-user to shower, bathe, swim or conduct other activities, yet also allow the patient-user to readily re-connect the disposable housing portion 20 to the module 103, for example, upon completion of such activities. Examples of connectors can be found in U.S. patent application Ser. No. 10/328,393 filed Dec. 22, 2003, and entitled "Reservoir Connector," and U.S. Pat. No. 5,545,152 issued Aug. 13, 1996, and entitled "Quick-Connect Coupling For A Medication Infusion System," both of which are incorporated herein by reference in their entirety. In other alternatives, different connectors such as Luer locks, or the like may be used.

Figure 32:
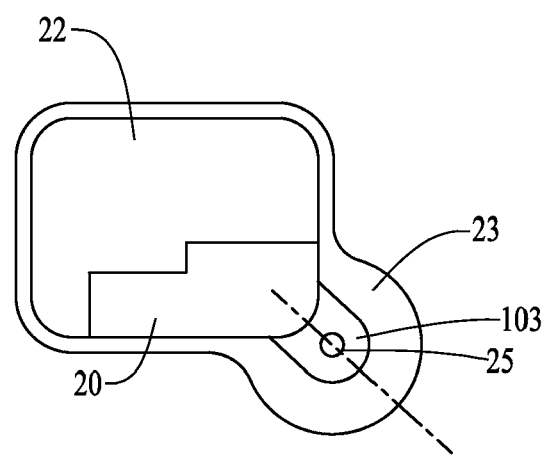
FIG. 32 shows a schematic top view of an arrangement of a durable housing portion and a disposable housing portion of a delivery system according to another embodiment of the invention.

In yet further embodiments, the conduit 102 may be eliminated and an injection site module 103 may be directly connected with the disposable housing portion 20, as shown in FIG. 32. In such an embodiment, one or more suitable fluid flow passages are provided through the disposable housing portion 20 and into the injection site module 103, for fluid-flow communication between the reservoir in the disposable housing portion 20 and a hollow needle or cannula, as described above. Also, in such embodiments, the injection site module 103 and the disposable housing portion 20 may include mating connection structures to allow the injection site module 103 and the disposable housing portion 20 to be selectively connected and disconnected from each other.

Figure 33:
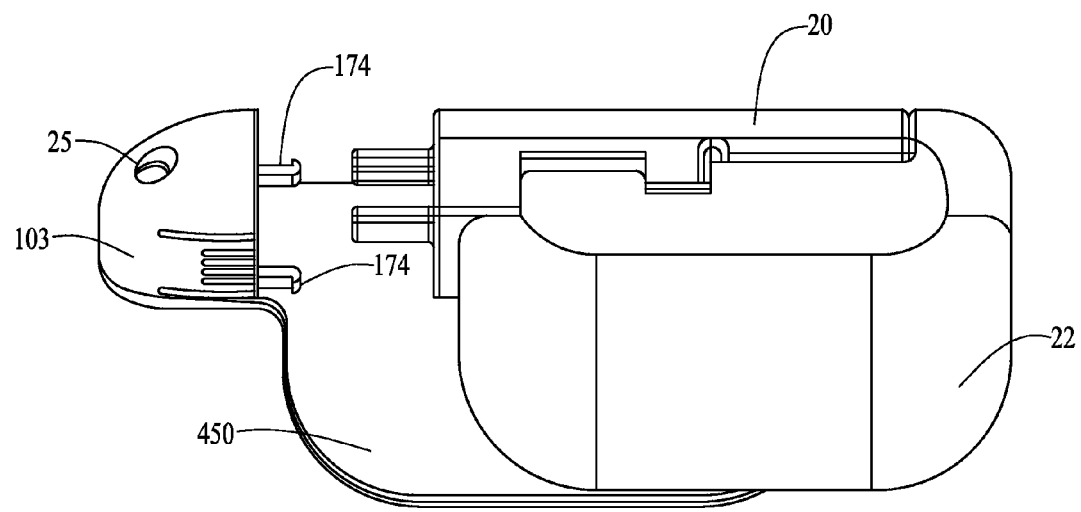
FIGS. 33-34 each show a perspective view of a connection arrangement for a disposable housing portion and an injection site module.
Figure 34:
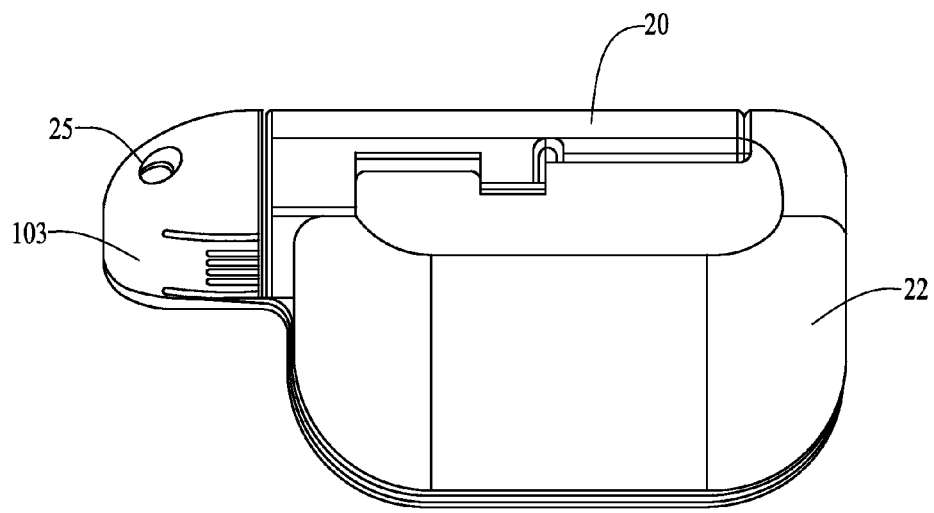
Figure 35:
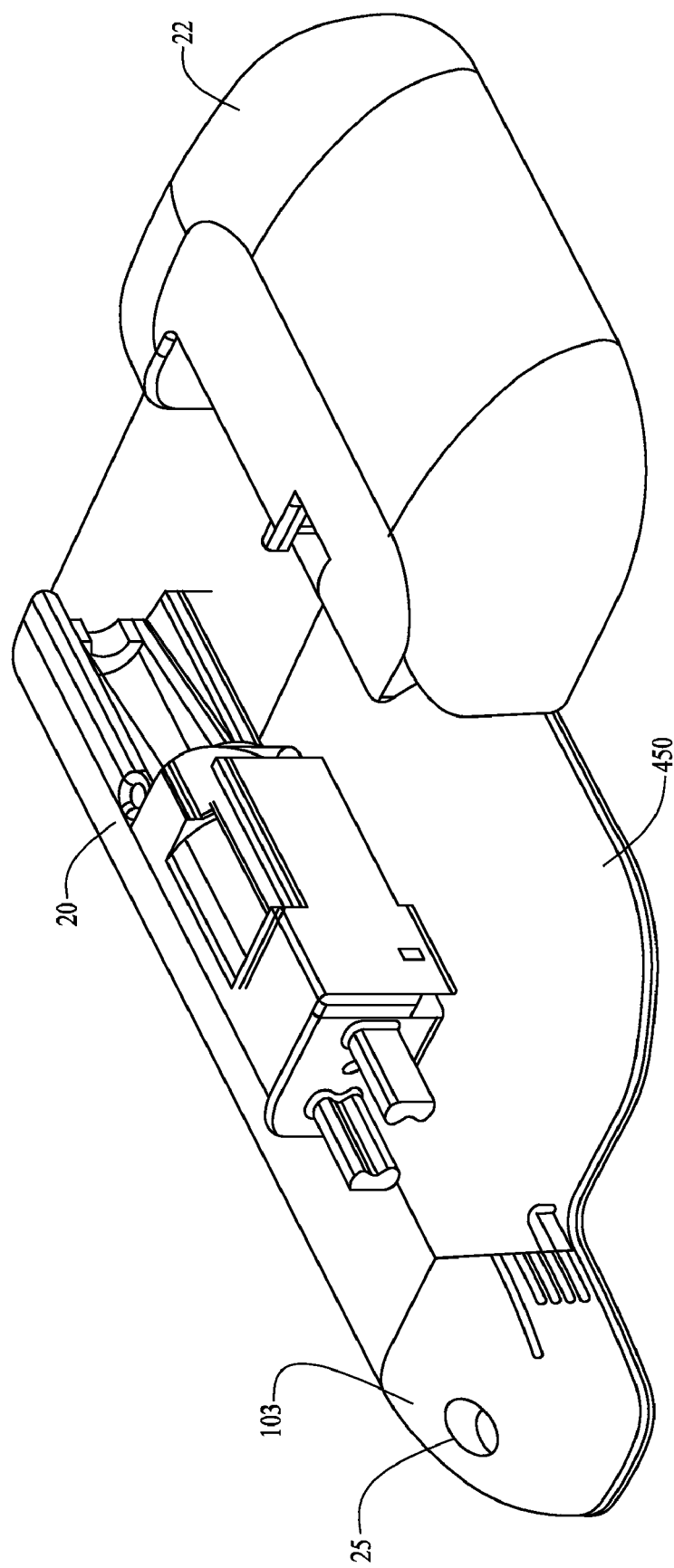
FIGS. 35 and 36 each show a perspective view of another connection arrangement for a disposable housing portion and an injection site module.

Various examples of mating arrangements, for directly connecting an injection site module 103 to a disposable housing portion are described with reference to FIGS. 33-40. FIGS. 33-35 show an example arrangement, in which an injection site module 103 includes at least one (two in FIG. 33) protruding engagement pawl 174 that are configured to be received in a corresponding number of receptacles on the disposable housing portion 20 (similar to the pawls 74 and receptacles 76 described in U.S. Patent Application No. 60/839,741, titled INFUSION PUMPS AND METHODS AND DELIVERY DEVICES AND METHODS WITH SAME, filed Aug. 23, 2006, which has been incorporated herein by reference. In other embodiments, the pawl(s) 174 may be located on the disposable housing portion 20, while the corresponding receptacles may be located on the module 103. In yet other embodiments, each of the disposable housing portion 20 and the module 103 may include one or more pawls and one or more receptacles.

The pawls 174 and receptacles may be configured to allow a patient-user to manually slide the pawls into the receptacles as the disposable housing portion 20 and the module 103 are brought together. When the pawls 174 are received in the corresponding receptacles, the module 103 is secured to the disposable housing portion 20. The pawls 174 may include a shaped portion or head to provide a snap-fit with the receptacles, when the pawls 174 are fully received within the receptacles. The pawls 174 may be configured with sufficient flexibility to allow the patient-user to separate the disposable housing portion 20 from the module 103, by applying a sufficient force to pull those two parts away from each other and unsnap the pawls 174 from the receptacles. In the embodiment of FIGS. 33-35, the module 103 may be attached to or may include a base portion 450 that may be secured to a patient-user's skin during operation, in lieu of the extended base 21 of the disposable housing portion 20 described above. The base portion 450 may include an adhesive material as described herein with respect to the base 21 of the disposable housing portion 20.

As shown in FIG. 35, the embodiment of FIGS. 33-35 may be formed in three general parts, including the disposable housing portion 20, the durable housing portion 22 and the module 103 on the base portion 450. The durable housing portion 22 and the disposable housing portion 20 may be secured together (as shown in FIG. 33), and the combined, connected disposable and durable housing portions may be secured to the module 103 and base portion 450. In one embodiment, the base portion 450 may be secured to a patient-user's skin, before the combined, connected disposable and durable housing portions are secured to the module 103 and base portion 450. In a further embodiment, the combined, connected disposable and durable housing portions are secured to the module 103 and base portion 450, before the base portion 450 is secured to the patient-user's skin.

Figure 36:
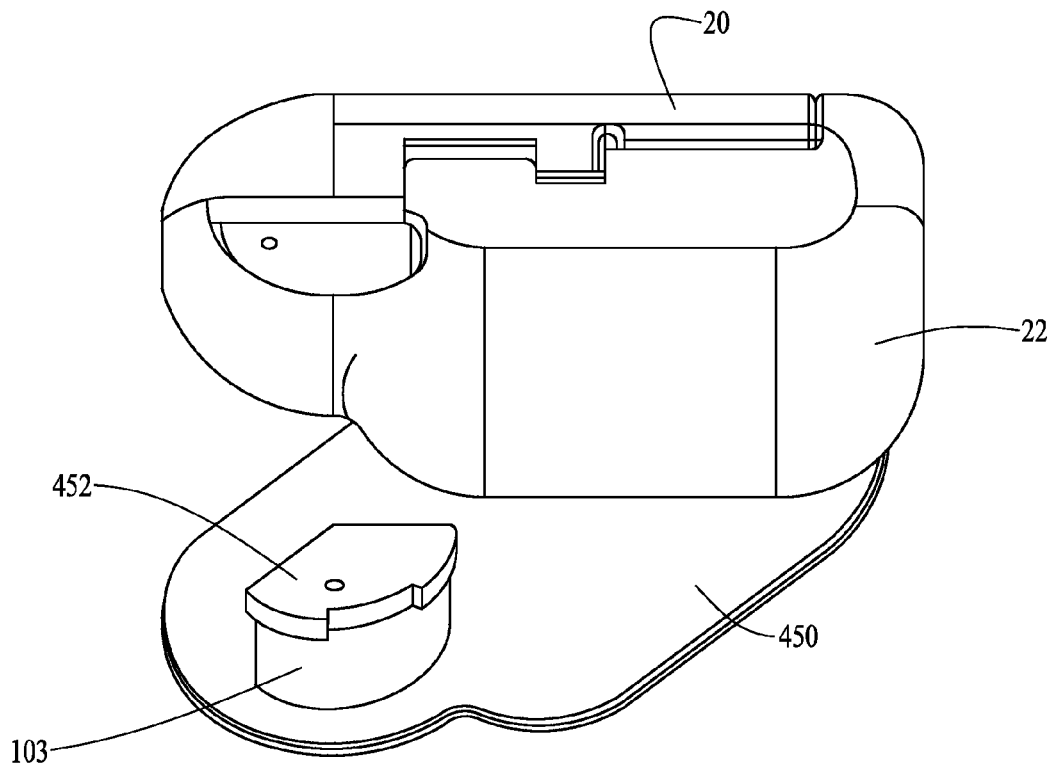
Figure 37:
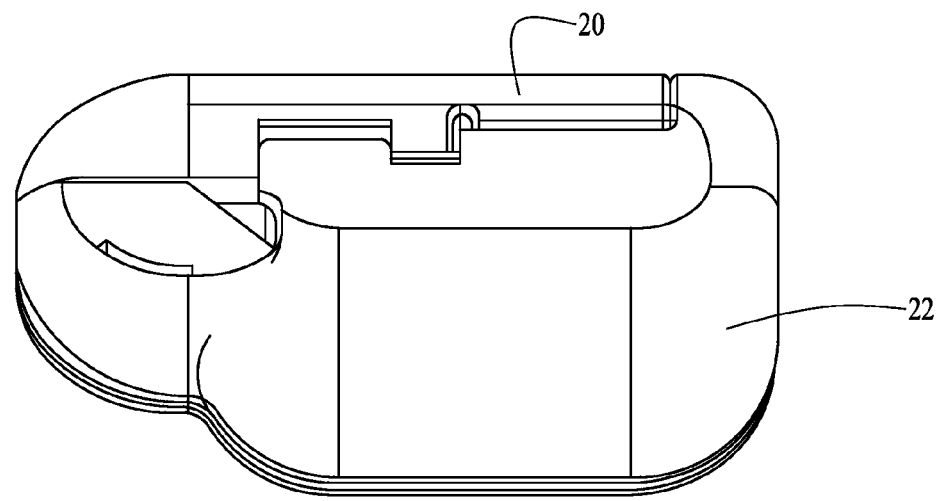

Another example of a connection structure is described with reference to FIGS. 36 and 37, wherein the module 103 includes a shaped head 452 configured to be received within a correspondingly shaped opening or receptacle in the disposable housing portion 20. The shaped head 452 may be configured with a shape that allows the head to be received in the receptacle when the disposable housing portion 20 is aligned relative to the module 103 in a first alignment position, as shown in FIG. 36, and further allows the disposable housing portion 20 to be rotated relative to the module 103 while the head 452 is received within the receptacle to a second alignment position as shown in FIG. 37. The receptacle in the disposable housing portion 20 may be shaped to allow the head 452 to be freely received or removed from the receptacle, when the disposable housing portion 20 is in the first alignment position (FIG. 36), yet abut the head 452 and inhibit separation of the head 452 from the receptacle (and, thus, inhibit separation of the disposable housing portion 20 from the module 103), when the disposable housing portion is in the second alignment position (FIG. 37).

Figure 38:
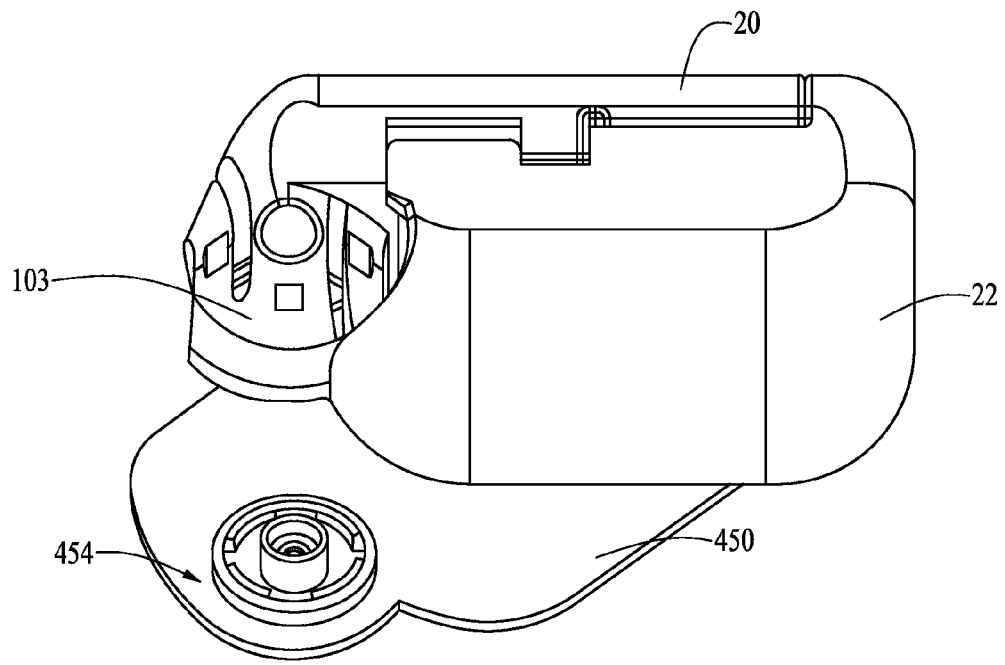
Figure 39:
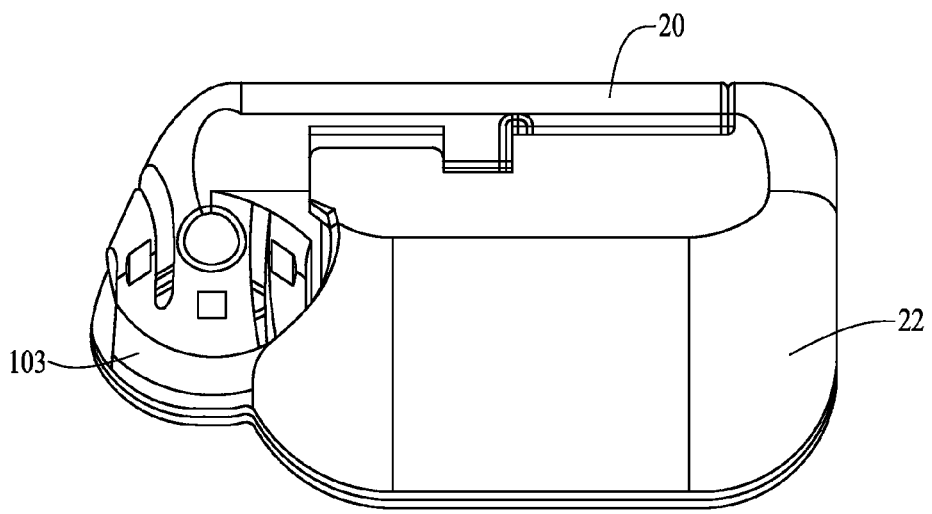

A further example of a connection structure is described with reference to FIGS. 38-40, wherein the device incorporates three parts, the durable housing portion 22, the disposable housing portion 20 and a base 456. A shaped receptacle 454 on the base portion 456 is configured to receive a correspondingly shaped connector member in the disposable housing portion 20. In FIGS. 38-40, the module 103 is formed, integral with the disposable housing portion 20. The shaped receptacle 454 may be configured with a shape that allows the connector member in module 103 to be engaged with the receptacle 454, when the disposable housing portion 20 is aligned relative to the base 456 and receptacle 454 in a first alignment position, as shown in FIG. 38, and further allows the disposable housing portion 20 to be rotated relative to the base 456 and receptacle 454, while the receptacle 454 is engaged within the connector member, to a second alignment position as shown in FIG. 39. The receptacle 454 and the connector member in the disposable housing portion 20 may be shaped to allow the connector member to be freely engage the receptacle 454, when the disposable housing portion 20 is in the first alignment position (FIG. 38), yet lock with the receptacle 454 and inhibit separation of the connector member from the receptacle (and, thus, inhibit separation of the disposable housing portion 20 from the module 103), when the disposable housing portion is in the second alignment position (FIG. 39). The receptacle 454 and connection member may include any suitable known rotary connection structures for connecting two structures together upon engagement and relative rotation of the two structures in one direction, yet allow the two structures to be disengaged and separated from an engaged arrangement, by relative rotation of the two structures in the second, opposite direction. A motion inhibiting structure, such as a locking tab, pawl or the like, may be provided to inhibit relative motion between the disposable housing portion 20 and the base 456, once those parts have been connected, as described above.

As shown in FIG. 40, the embodiment of FIGS. 38-40 may be formed in three general parts, including the disposable housing portion 20, the durable housing portion 22 and the module 103 on the base portion 456. The durable housing portion 22 and the disposable housing portion 20 may be secured together (as shown in FIG. 38), and the combined, connected disposable and durable housing portions may be secured to the base portion 456. In one embodiment, the base portion 456 may be secured to a patient-user's skin, before the combined, connected disposable and durable housing portions are secured to the base portion 456. In a further embodiment, the combined, connected disposable and durable housing portions are secured to the base portion 456, before the base portion 456 is secured to the patient-user's skin.

In yet further embodiments, the injection site module may be formed as a unitary structure with the disposable housing portion 20. Also, in any of the embodiments described above, one or more sensors may be located in the disposable housing portion 20, the injection site module 103 or the durable housing portion 22, for sensing a biological condition, including, but not limited to, blood glucose level, level of infusion medium in the patient-user's blood and/or other conditions. Such sensor(s) may include a hollow needle or cannula and/or a set of micro-needles, as described above, for piercing the patient-user's skin to convey fluid from the patient to the sensor.

Various aspects of the multiple embodiments described above may be employed independently or in combinations thereof. Significant advantages can be obtained from various embodiments and combinations described herein, wherein an at-site delivery system may be made of two parts, including a disposable portion and a non-disposable portion. The disposable portion may contain all materials that are in direct contact with the infusion medium, such as reservoir body, reservoir piston, septum systems and injection needle. The non-disposable portion could contain substantially the materials that are not in contact with the medication including the drive system, pressure or force sensing system, battery, electronics, display, and non-disposable housing. The pump could be designed such that the disposable portion (with an unused new, user-filled, prefilled, refurbished, remanufactured or re-filled reservoir 26) is inserted into the non-disposable portion. By simplifying the manner in which the disposable portion of the delivery device can be replaced and by simplifying the manner in which the delivery device can be re-activated after replacing a disposable portion, a greater number of patient-users will be able to use and benefit from such delivery devices.

While particular embodiments of the present invention have been shown and described, it will be obvious to those skilled in the art that the invention is not limited to the particular embodiments shown and described and that changes and modifications may be made without departing from the spirit and scope of the claimed invention. For example, while embodiments described above may include an adhesive material and a cover film 23 (FIGS. 2 and 3), further embodiments may include a plurality of adhesive material layers alternating with a corresponding plurality of cover film layers 23, to allow the delivery device to be secured, removed and re-secured to the patient-user's skin one or more times.

In such embodiments, a first cover film layer located at the end of the stack of alternating layers of adhesive material and cover film, may be removed to expose a first layer of adhesive material. With the first layer of adhesive material exposed, the delivery device (or component thereof) may be adhered to a patient-user's skin, as described above. After a suitable period of usage, the delivery device (or component having the adhesive) may be removed from the patient-user's skin, for example, for servicing, re-filling, replacement of one or more components, or the like. After removal of the delivery device (or component) from the patient-user's skin, a second cover film layer on the delivery device (or component) may be removed to expose a second layer of adhesive material. With the second layer of adhesive material exposed, the delivery device (or component) may be secured to the same patient-user or, in certain contexts, to a different patient-user, for further operation. The process may be repeated a number of times up to the number of adhesive material and cover film layer pairs are included in the plural alternating layers of adhesive material and cover film.

In addition, while embodiments described above include an injection site located on the disposable housing portion 20 or in an external injection site module 103, other embodiments may employ an injection site located in the durable housing portion 22 and connected, through suitable fluid-flow passages, to the reservoir in the disposable housing portion 20, when the durable housing portion and disposable housing portion are engaged. Also, while embodiments are described above in the context of delivery devices for delivering an infusion medium from a reservoir to a patient-user, other embodiments may be operated to withdraw a fluidic medium from a patient-user (or other source) and transfer the fluidic medium to the reservoir. Such other embodiments may be operated by operating the drive device to selectively move the piston plunger away from the septum-end of the reservoir (to increase the fluid-retaining volume of the reservoir) to create a negative pressure sufficient to draw fluid from the patient-user (or other source) to which the hollow needle or cannula is secured.

Also, various embodiments described above may employ a reservoir 26, 126, 226, 326, 426 that, in some examples, may comprise a cartridge or canister that is removable from (to be operatively disengaged from) and insertable into (to be operatively engaged with) the first or disposable housing portion 20. In this manner, a reservoir cartridge or canister (first container) may be removed and replaced with a new, refilled, pre-filled, user-filled, refurbished or remanufactured cartridge or canister (second container). In such embodiments, the reservoir cartridge may include an electronic storage device (such as an electronic memory chip or the like) for storing information, such as, but not limited to, identification of the contents of the reservoir, identification of the maker of the reservoir or its contents, information relating to the state of fill or depletion of the reservoir, or the like. Suitable electrical contact pads located in the disposable housing portion may electrically connect with contact pads on the reservoir, to electrically connect the electronic storage device on the reservoir canister with suitable electronics in the disposable housing portion or the durable housing portion 22, for reading information stored on the electronic storage device. Such information (or other information, warnings, etc., associated with the stored information) may be displayed on a display device on the durable housing portion 22, when the reservoir canister is inserted into the disposable housing portion 20, and the disposable housing portion 20 and the durable housing portion 22 are engaged.

In addition, in any of the above-described embodiments, one or both of the disposable housing portion 20 and the durable housing portion 22 (and/or a separate base portion 21' or 450 or a separate injection site module 103) may include a force sensor (not shown) or other suitable sensing device for sensing the proper placement or engagement of one or more of the disposable housing portion 20 and the durable housing portion 22 (and/or a separate base portion or a separate injection site module) on a patient-user's skin (or other proper location for operation with the patient). In such an embodiment, further electronics may control the operation of the drive device to inhibit operation of the drive device and/or the needle injector, unless the sensor senses the proper operable engagement of one or more of the disposable housing portion 20 and the durable housing portion 22 (and/or a separate base portion or a separate injection site module) with the patient-user's skin (or other proper location for operation).

Alternatively or in addition, one or both of the disposable housing portion 20 and the durable housing portion 22 may include a sensing device (not shown) for sensing the proper operable engagement of the disposable housing portion 20 and the durable housing portion 22 together (and/or with a separate base portion or a separate injection site module). In such an embodiment, further electronics may control the operation of the drive device to inhibit operation of the drive device and/or the needle injector, unless the sensor senses the proper operable engagement of the disposable housing portion 20 and the durable housing portion 22 together (and/or with a separate base portion or a separate injection site module).

In any of the above embodiments, a sensor may be provided in (or otherwise associated with) the reservoir to detect a low volume of infusion medium in the reservoir. For example, a sensor may be configured to detect a condition at which the volume of infusion medium in the reservoir reaches a threshold minimal level. A warning device may be operably connected to the sensor, to provide a warning signal, upon the detection of a low volume condition. The warning device may provide an audible warning sound, a visible warning signal and/or a tactile warning signal (such as, but not limited to a perceptible vibration) to the patient-user, upon the detection of the volume of infusion medium in the reservoir reaching a threshold minimal level. In one embodiment, the visible warning may be provided as a message on an electronic display (as described above) on the durable housing portion 22. Alternatively or in addition, a warning signal condition may be communicated to and displayed on a remote CCD 16 or computer 18 (FIG. 2), for example, through wireless communication electronics as described above.

In addition, while various embodiments described above may include one or more adhesive layers, each having a peelable cover layer, other embodiments may employ a single adhesive layer having (or plural adhesive layers, each having) a pattern of plural peelable cover layer portions, such that a patient-user may peel off one portion of the cover layer for adhering the delivery device to the patient-user as described above, while leaving the rest of the pattern of peelable cover layer portions on the adhesive. In such an embodiment, after completion of a first period of operation of the delivery device and removal of the delivery device from the patient-user, a second portion of the peelable cover layer may be removed from the adhesive layer and the delivery device may be adhered to a patient-user for a second period of operation.

Also, while various delivery device embodiments described above include base portions (for example, 21, 21' and 450) that are configured to be secured to a patient-user's skin (or other suitable surface of operation) and that extend along the full length and width of the delivery device structure, other embodiments may employ base portions (that secure to the patient-user's skin or other surface) that are configured to be less than the full length or width dimension of the delivery device structure, to minimize the surface area in contact with the patient-user (or other surface) and, thus, improve patient-user comfort during operation. Base portions having shapes and sizes different from those shown in the accompanying drawings may be employed for additional improvements with regard to patient-user comfort and minimizing surface area in contact with the patient-user. Furthermore, as noted above, the base portion may be composed of a flexible material that at least partially conforms to the curvature and movement of the patient-user's body.

In any of the above-described embodiments in which an adhesive material is used to secure one or more of the delivery device components to the patient-user's skin (or other suitable surface for operation), multiple types of adhesive materials (or multiple strengths of adhesives) may be employed, such that a stronger adhesive is provided in certain areas (such as around the needle injection site), while a weaker adhesive is provided in other areas.

What is claimed is:

1. A delivery device for delivering a fluidic medium from first and second containers to a user, each container having a container wall defining an interior volume for containing the fluidic medium and a generally rigid plunger moveable within the interior volume of the container along an axial direction of the container for conveying the fluidic medium from the interior volume of the container, the device comprising:
    a first housing portion adapted to be secured to a user, the first housing portion configured to be selectively engaged with and disengaged from the first container to allow disposal of the first container without disposing of the first housing portion and to allow selective engagement with and disengagement from the second container;
    a second housing portion configured to be selectively engaged with and disengaged from the first housing portion;
    an expandable structure supported by the first housing portion, the expandable structure having an interior volume and a surface for engaging the plunger and moving the plunger within the interior volume of the first container as the expandable structure is expanded;
    a reservoir supported by the second housing portion, the reservoir for containing a fluidic medium for expanding the expandable structure;
    a conduit for coupling the reservoir to the interior volume of the expandable structure; and
    a drive device supported by the second housing portion, the drive device for selectively conveying the fluidic medium of the reservoir through the conduit from the reservoir to the interior volume of the expandable structure to selectively expand the expandable structure to engage and move the plunger within the interior volume of the first container to convey the fluidic medium from the interior volume of the first reservoir housing;
    wherein, after the expandable structure has moved the plunger of the first container to convey at least some of the fluidic medium out of the interior volume of the first container, the first housing portion configured to be operatively disengaged from the first container and operatively engaged with the second container to allow the surface of the expandable structure to engage and move a plunger of the second container as the expandable structure is expanded to convey fluidic media from an interior volume of the second container.

2. A delivery device according to claim 1, wherein the drive device comprises a peristaltic drive device.

3. A delivery device according to claim 2,
    wherein the peristaltic drive device comprises a rotatable rotor having a plurality of contact rollers or pads arranged to contact a first length of the conduit as the rotor is rotated; and
    wherein a support surface is provided on the second housing portion for supporting at least the first length of the conduit.

4. A delivery device according to claim 3, wherein the support surface comprises a curved surface.

5. A delivery device according to claim 1, wherein the drive device comprises a fluid pump.

6. A delivery device according to claim 3, wherein the drive device further comprises a motor operatively coupled to rotate the rotor.

7. A delivery device according to claim 6, further comprising linkage structure coupled to the motor and to the rotor, the linkage structure for transferring drive force from the motor to the rotor.

8. A delivery device according to claim 1, wherein the drive device comprises:
    a rotatable rotor having a plurality of contact rollers or pads arranged to contact a first length of the conduit as the rotor is rotated; and
    a motor operatively coupled to rotate the rotor;
    wherein a support surface is provided on the second housing portion for supporting at least the first length of the conduit.

9. A delivery device according to claim 1,
wherein the drive device comprises a rotatable rotor having a plurality of contact rollers or pads arranged to contact a first length of the conduit as the rotor is rotated along a radius of curvature; and
wherein a curved surface is provided on the second housing portion for supporting at least the first length of the conduit, the curved surface having a radius of curvature approximating the radius of curvature of the rotor rollers or pads.

10. A delivery device according to claim 9, wherein the drive device further comprises a motor operatively coupled to rotate the rotor.

11. A delivery device according to claim 1, wherein the expandable structure comprises a bellows structure.

12. A delivery device according to claim 1, wherein the plunger is arranged separate from the container wall and supported for movement relative to the container wall.

13. A delivery device according to claim 12, the plunger configured to seal against the container wall.

14. A delivery device according to claim 13, the plunger having a sealing member that seals against the container wall.

15. A delivery device according to claim 12,
wherein the container wall comprises a first material; and
wherein the plunger comprises a second material different from the first material.

16. A delivery device according to claim 1,
the first housing portion comprising a disposable housing portion; and
the second housing portion comprising a durable housing portion configured to be selectively engaged with and disengaged from the disposable housing portion to allow disposal of the disposable housing portion without disposing of the durable housing portion.

17. A delivery device according to claim 1, wherein the surface of the expandable structure for engaging the plunger is arranged in contact with the plunger when moving the plunger.

18. A delivery device according to claim 1, wherein the plunger is not moved during the period of time in which the plunger remains in a first position.

19. A delivery device according to claim 1, the expandable structure configured to allow the plunger to remain in a first position indefinitely.

20. A delivery device according to claim 1,
the drive device for selectively conveying a first discrete volume of the fluidic medium through the conduit from the reservoir to the interior volume of the expandable structure to selectively expand the expandable structure to engage and move the plunger within the interior volume of first container to a first position to convey the first discrete volume of the fluidic medium from the interior volume of the first container; and
the drive device for selectively conveying a second discrete volume of the fluidic medium through the conduit from the reservoir to the interior volume of the expandable structure to selectively expand the expandable structure to engage and move the plunger within the interior volume of the first container to a second position to convey the second discrete volume of the fluidic medium from the interior volume of the first container following a period of time in which the plunger remains in the first position based on a reading from a sensor.

21. A delivery device according to claim 1, the expandable structure arranged at least partially within the interior volume of the first container when the first container is supported by the first housing portion.

22. A delivery device according to claim 1, wherein, when the second container is supported by the first housing portion, the drive device for selectively conveying the fluidic medium of the reservoir through the conduit from the reservoir to the interior volume of the expandable structure to selectively expand the expandable structure to engage and move the plunger within the interior volume of the second container to convey the fluidic medium from the interior volume of the second container.

23. A delivery device according to claim 16, wherein the disposable portion comprises the first container.

24. A delivery device according to claim 1,
the drive device for selectively conveying the fluidic medium of the reservoir through the conduit from the reservoir to the interior volume of the expandable structure to selectively expand the expandable structure to engage and move the plunger within the interior volume of the first container to a first position to convey a first discrete volume of the fluidic medium from the interior volume of the first container; and
the drive device for selectively conveying the fluidic medium of the reservoir through the conduit from the reservoir to the interior volume of the expandable structure to selectively expand the expandable structure to engage and move the plunger within the interior volume of the first container to a second position to convey a second discrete volume of the fluidic medium from the interior volume of the first container following a period of time in which the plunger remains in the first position.

25. A delivery device according to claim 1, the surface of the expandable structure is configured to engage the plunger of the second container and move the plunger within the interior volume of the second container when the first reservoir housing has been replaced with the second container.

26. A delivery device according to claim 25,
the drive device for selectively conveying the fluidic medium of the reservoir through the conduit from the reservoir to the interior volume of the expandable structure to selectively expand the expandable structure to engage and move the plunger within the interior volume of the first container to a first position to convey the first discrete volume of the fluidic medium from the interior volume of the first container; and
the drive device for selectively conveying the fluidic medium of the reservoir through the conduit from the reservoir to the interior volume of the expandable structure to selectively expand the expandable structure to engage and move the plunger within the interior volume of the first container to a second position to convey the second discrete volume of the fluidic medium from the interior volume of the first container following a period of time in which the plunger remains in the first position based on a reading from a sensor.

27. A delivery device according to claim 1, wherein, after the interior volume of the first container has been substantially emptied of the fluidic medium, the first housing portion configured to be operatively disengaged from the first reservoir housing and operatively engaged with the second container to allow the surface of the expandable structure to engage and move the plunger of the second container as the expandable structure is expanded to convey the fluidic media from the interior volume of the second container.

28. A delivery device according to claim 1, wherein the surface of the expandable structure for engaging the plunger is integral with the expandable structure.

29. A delivery device according to claim 1,
the expandable structure having an axial direction parallel with the axial direction of the first container, the expandable structure configured to expand along the axial direction of the expandable structure;
the expandable structure having a wall defining the interior volume of the expandable structure;
the wall extending along the entire length of the axial direction of the expandable structure; and
the wall comprising the surface of the expandable structure for engaging the plunger of one of the first and second containers.

30. A delivery device according to claim 1, the first housing portion having a recess for selective insertion of the first container into and removal of the first container from the recess.

31. A method for making a delivery device for delivering a fluidic medium from first and second containers, each container having a wall defining an interior volume for containing the fluidic medium and a generally rigid plunger moveable within the interior volume of the container along an axial direction of the container for conveying the fluidic medium from the interior volume of the container to a user, the method comprising:
providing a first housing portion adapted to be secured to a user;
configuring the first housing portion to be selectively engaged with and disengaged from the first container to allow disposal of the first container without disposing of the first housing portion and to allow selective engagement with and disengagement from second container;
providing a second housing portion configured to be selectively engaged with and disengaged from the first housing portion;
supporting an expandable structure on the first housing portion, the expandable structure having an interior volume;
arranging a surface of the expandable structure for engaging the plunger and moving the plunger within the interior volume of the first container as the expandable structure is expanded;
supporting a reservoir on the second housing portion, the reservoir for containing a fluidic medium for expanding the expandable structure;
coupling a conduit in fluid flow communication with the reservoir and the interior volume of the expandable structure; and
supporting a drive device on the second housing portion, the drive device for selectively conveying the fluidic medium of the reservoir through the conduit from the reservoir to the interior volume of the expandable structure to selectively expand the expandable structure to engage and move the plunger within the interior volume of the first container to convey the fluidic medium from the interior volume of the first container;
wherein, after the expandable structure has moved the plunger of the first container to convey at least some of the fluidic medium out of the interior volume of the first container, the first housing portion configured to be operatively disengaged from the first container and operatively engaged with the second container to allow the surface of the expandable structure to engage and move a plunger of the second container as the expandable structure is expanded to convey fluidic media from an interior volume of the second container.

32. A method according to claim 31, wherein supporting a drive device comprises supporting a peristaltic drive device to the conduit.

33. A method according to claim 31, wherein supporting a drive device comprises supporting a rotatable rotor for rotation and arranging the rotor having a plurality of contact rollers or pads to contact a first length of the conduit as the rotor is rotated.

34. A method according to claim 33, further comprising providing a support surface for supporting the first length of the conduit.

35. A method according to claim 34, wherein the support surface is curved.

36. A method according to claim 33, wherein supporting a drive device further comprises operatively coupling a motor to rotate the rotor.

37. A method according to claim 36, wherein supporting a motor comprises coupling a linkage structure to the motor and to the rotor for transferring drive force from the motor to the rotor.

38. A method according to claim 37, further comprising providing a support surface for supporting the first length of the conduit, wherein the support surface is curved.

39. A method according to claim 31, wherein supporting a drive device comprises:
supporting a rotatable rotor for rotation, the rotor having a plurality of contact rollers or pads arranged to contact a first length of the conduit as the rotor is rotated along a radius of curvature; and
supporting at least the first length of the conduit on a surface in the second housing portion.

40. A method according to claim 39, wherein supporting at least the first length of the conduit comprises arranging a curved surface to support the first length of the conduit, the curved surface having a radius of curvature approximating the radius of curvature of the rotor rollers or pads.

41. A method according to claim 40, wherein the expandable structure comprises a bellows structure.

42. A method according to claim 31, wherein the expandable structure comprises a bellows structure.

* * * * *